United States Patent [19]

Keller et al.

[11] Patent Number: 5,525,497
[45] Date of Patent: Jun. 11, 1996

[54] RECOMBINANT POLY(A) POLYMERASE

[76] Inventors: Walter Keller, Hebelstrasse 11, Basel, Switzerland, CH-4056; Joachim Lingner, Gundeldingerstrasse 35, Basel, Switzerland, CH4053; Georges Martin, Lothringerstrasse 125, Basel, Switzerland, CH4056; Elmar Wahle, Roetteler Ring 15a, Grenzach-Wyhlen, Germany, D-7889

[21] Appl. No.: 803,622

[22] Filed: Nov. 27, 1991

[51] Int. Cl.⁶ .............. C12N 9/12; C12N 15/54; C12N 15/70; C07K 1/18

[52] U.S. Cl. .......... 435/194; 536/23.2; 435/69.1; 435/320.1; 435/252.33; 530/415; 530/416

[58] Field of Search .......... 536/27, 23.2; 435/69.1, 435/320.1, 194, 252.33, 415, 416

[56] References Cited

U.S. PATENT DOCUMENTS

| | | | |
|---|---|---|---|
| 4,394,443 | 7/1983 | Weissman et al. | 435/6 |
| 4,727,028 | 2/1988 | Santerre et al. | 435/240.2 |
| 4,800,159 | 1/1989 | Mullis et al. | 435/172.3 |

OTHER PUBLICATIONS

Baranov et al. 1989 (Abstract Accession No. 90128291 of File 155 of Dialog) Gene 84(2):463–466.
Lee et al. 1988. Science 239:1288–1291.
Ullrich et al. 1984. The EMBO J. 3(2):361–364.
Woznez, 1990. Methods in Enzymology 182:738–749.
Sambrook et al. 1989. "Molecular Cloning", CSH Press, 17.1–17.41.
Munroe et al. 1990. Gene 91:151–158.
Watson, James D. 1987. *Molecular Biology of the Gene*, The Benjamin Cummings Publishing Co. Inc., Menlo Park, CA, p. 313.
Ryner, et al. Oct. 1989. Mol. and Cellular Biology 9(10):4229–4238.
Hoff et al. Mar. 10, 1975. J. Biol. Chem. 250(5):1838–1846.
Saluja et al. 1989. Plant Science 60:27–38.
Maguire et al. 1986. Biochemistry 25(7):1515–1519, (Abstract only).
Yuen et al. Jan. 1989. Bio Techniques, 7(1):74–82.
Sofer et al. Nov./Dec. 1983. Bio Techniques, pp. 198–203.
Bely et al. Apr. 1982. Federation of America Societies for Experiments Biology, New Orleans, Louisiana, p. 1450, Abstract No. 6896.
Raabe et al., 353 *Nature* 229, 1991.
Wahle, 266 *J. Biol. Chem.* 3131, 1991.
Lingner et al., 266 *J. Biol. Chem.* 8741, 1991.
Studier, 219 *J. Mol. Biol.* 37, 1991.
Nielsen et al., 13 *Nuc. Acid. Res.* 6867, 1985.
Clos et al., 63 *Cell* 1085, 1990.
Schiltz et al., 199 *Eur. J. Biochem.* 587, 1991.
MacDonald et al., 152 *Methods Enzymol.* 219, 1987.
Koch et al., 53 *Eur. J. Cell Biol.* 1, 1990.
Wahle, 66 *Cell* 759, 1991.
Munroe and Jacobson, 91 *Gene* 151, 1990.
Keller and Crouch, 69 *Proc. Natl. Acad. Sci.* 3360, 1972.
Beltz and Ashton, 41 *Fed. Proc.* 1450, Abstract 6896, 1982.
Gething et al., 287 *Nature* 301, 1980.
Wickens, 15 *TIBS* 320, 1990.
Gershon et al., 66 *Cell* 1269, 1991.
Gallie et al., 228 *Mol. Gen. Genet* 258, 1991.
Bernstein et al., 14 *TIBS* 373, 1989.
Sachs, 2 *Cell Biol.* 1092, 1990.

*Primary Examiner*—Keith C. Furman
*Attorney, Agent, or Firm*—Lyon & Lyon

[57] ABSTRACT

Purified nucleic acid encoding a yeast, human, or bovine poly(A) polymerase, where the bovine nucleic acid consists essentially of that nucleic acid sequence shown as nucleotide SEQ. ID. NO.: 1; the resulting recombinant poly(A) polymerase expressed from these nucleic acids, corresponding methods of their production, and methods of use of the poly(A) polymerase.

11 Claims, 37 Drawing Sheets

| PEPTIDE: | SEQUENCE |
|---|---|
| | 1 → |
| | ← 2 |
| N-TERMINUS | PFPVTTQGSQQTQPXQKXYG |
| | ← 4 |
| 101 | TDEILHLVPNIDNFRLTLRAIKLXAK |
| 96 | THNIYSNILGFLGGVSXAMLVAR |
| 66 | QRLEWVGLVESK |

FIG. 1a.

```
                    10                  30                  50
          GCGGTTGCGGGGGGGAAGTGACTGGGCGGTGCGGCGCAGGAGACGATGCCGTTTCCAGTT    20
                    70                  90                 110          MetProPheProVal
  1    ACAACACAGGATCACACAGCAAACACAGCGCCACAGAAGCACTACTTCTCCC
                    130                 150                 170
 21    ThrThrGlnGlySerGlnGlnThrGlnProGlnLysHisTyrGlyIleThrSerPro    40
                    190                 210                 230
       ATCAGCTTAGCAGCCCCCAAGGAGACTGCTCCTCACACAGAAGCTGTGGAGACT
 41    IleSerLeuAlaAlaProLysGluThrAspCysLeuLeuThrGlnLysLeuValGluThr    60
                    250                 270                 290
       CTGAAGCCCTTCGGGGTTTTTGAAGAGGAACTGCAGCGCCAGGATTTTTATTTG
 61    LeuLysProPheGlyValPheGluGluGluGluLeuGlnArgArgIlePheIleLeu    80
                    310                 330                 350
       GGAAAATTAAATAACCTGGTAAAAGAGTGGATACGAGAAATCAGTGAAAGCAAGAATCTT
 81    GlyLysLeuAsnAsnLeuValLysGluTrpIleArgGluIleSerGluSerLysAsnLeu   100
                    370                 390                 410
       CCACAATCTGTAATTGAAAATGTTGGTGGGAAATTTTACATTTGGATCTTATAGATTA
101    ProGlnSerValIleGluAsnValGlyGlyLysIlePheThrPheGlySerTyrArgLeu   120
       GGAGTACATACAAAAGGTCTGATATTGATGCATTGTTGTTGCACCAAGACATGTTGAT
121    GlyValHisThrLysGlyAlaAspIleAspCysValAlaLeuCysValAlaProArgHisValAsp   140
```

FIG. 1a-1.

```
                                430              450              470
                                 .                .                .
141  CGAAGTGATTTTTCACCTCATTCTATGATAAGTTGAAATTACAGGAAGAAGTAAAAGAT
     ArgSerAspPhePheThrSerPheTyrAspLysLeuLysLeuGlnGluGluValLysAsp  160
                      490              510              530
                       .                .                .
161  TTAAGAGCTGTTGAAGAGGCATTTGTACCAGTTATCAAACTGTGTTTTGATGGATACAG
     LeuArgAlaValGluGluAlaPheValProValIleLysLeuCysPheAspGlyIleGlu  180
                      550              570              590
                       .                .                .
181  ATTGATATTTTGTTTGCAAGATTAGCACTGCAGAGACTTATTCCAGAAGACTTGGACTTAAGA
     IleAspIleLeuPheAlaArgLeuAlaLeuGlnThrIleProGluAspLeuAspLeuArg  200
                      610              630              650
                       .                .                .
201  GATGACAGTCTGCTTAAAAATTTAGATATAAGAAGTCTTAACGGTTGCAGG
     AspAspSerLeuLeuLysAsnLeuAspIleArgSerLeuAsnGlyCysArg  220
                      670              690              710
                       .                .                .
221  GTAACCGATGAAATTTTACATCTAGTACCAAACATTGACAACTTCAGTTAACCCTGAGA
     ValThrAspGluIleLeuHisLeuValProAsnIleAspAsnPheArgLeuThrLeuArg  240
                      730              750              770
                       .                .                .
241  GCTATCAAACTGTGGGCCAAACGCCACAACATCTATTCCAATATATTAGGTTTCCTCGGT
     AlaIleLysLeuTrpAlaLysArgHisAsnIleTyrSerAsnIleLeuGlyPheLeuGly  260
                      790              810              830
                       .                .                .
261  GGTGTTCCTGGGCTATGCTAGTAGCAAGAACTTGCCAGCTTTATCCAAATGCAATAGCA
     GlyValSerTrpAlaMetLeuValAlaArgThrCysGlnLeuTyrProAsnAlaIleAla  280
```

FIG. 1b.

```
            850                 870                 890
              .                   .                   .
     TCAACTCTTGTACATAAATTTTCTGGTATTTTCTAAATGGGAATGGCAAATCCAGTC  300
281  SerThrLeuValHisLysPhePheLeuValPheSerLysTrpGluTrpProAsnProVal
                    910                 930                 950
                      .                   .                   .
     CTATTGAAACAGCCTGAAGAATGCAATCTTAATTGCCTGTATGGACCCAAGGGTAAAC  320
301  LeuLeuLysGlnProGluCysAsnLeuAsnLeuProValTrpAspProArgValAsn
                    970                 990                1010
                      .                   .                   .
     CCCAGTGATAGGTACCATCTTATGCCTATAATTACACCAGCATACCCACAACAGAACTCC  340
321  ProSerAspArgTyrHisLeuMetProIleIleThrProAlaTyrProGlnGlnAsnSer
                   1030                1050                1070
                      .                   .                   .
     ACGTACAATGTGTCCGTTTCAACACGGATGGTCATGGTTGAGGAGTTTAAACAAGGTCTT  360
341  ThrTyrAsnValSerValSerThrArgMetValMetValGluGluPheLysGlnGlyLeu
                   1090                1110                1130
                      .                   .                   .
     GCTATCACAGATGAAATTTGCTGAGTAAGGCAGAGTGGTCCAAACTTTTTGAAGCTCCA  380
361  AlaIleThrAspGluIleCysStopLysAlaGluTrpSerLysPheGluAlaPro
                   1150                1170                1190
                      .                   .                   .
     AACTTCTTTCAAAAGTACCAGCATGATATTGTACTTCTAGCAAGTGCACCAACTGAAAAA  400
381  AsnPhePheGlnLysTyrGlnHisAspIleValLeuLeuAlaSerAlaProThrGluLys
                   1210                1230                1250
                      .                   .                   .
     CAACGCCTAGAATGGGCTGGCTTGGTGAATCAAAAATCCGAATCCTGGTTGGAAGTTTG  420
401  GlnArgLeuGluTrpValGlyLeuValGluSerLysIleArgIleLeuValGlySerLeu
```

FIG. 1b-1.

```
                        1270                    1290                     1310
                           .                       .                        .
    GAGAAGAATGAGTTTATGACACTGGCTCATGTGAATCCCCAGTCATTCCAGCACCCAAA
421 GluLysAsnGluPheMetThrLeuAlaHisValAsnProGlnSerPheProAlaProLys 440
                         1330                    1350                     1370
                           .                       .                        .
    GAAATCCCGACAAGGAAGAATTTCGCACTATGTGGGTGATTGGGTTAGTGTTAACAAA
441 GluAsnProAspLysGluGluPheArgThrMetTrpValIleGlyLeuValPheAsnLys 460
                         1390                    1410                     1430
                           .                       .                        .
    ACAGAAAACTCTGAAAATCTCAGTGTTGATCTCACCTATGATATTCAGTCTTTCACAGAT
461 ThrGluAsnSerGluAsnLeuSerValAspLeuThrTyrAspIleGlnSerPheThrAsp 480
                         1450                    1470                     1490
                           .                       .                        .
    ACAGTTTATAGGCAAGCAATAAACAGCAAGATGTTTGAGGTGGACATGAAAATTGCTGCG
481 ThrValTyrArgGlnAlaIleAsnSerLysMetPheGluValAspMetLysIleAlaAla 500
                         1510                    1530                     1550
                           .                       .                        .
    ATGCATGTAAAAAGAAAGCAACTCCATCAACTACTGCCTAGTCATGTGCTTCAGAAAAAG
501 MetHisValLysArgLysGlnLeuHisGlnLeuLeuProSerHisValLeuGlnLysLys 520
                         1570                    1590                     1610
                           .                       .                        .
    AAAAAGCATTCAACAGAAGGCGTCAAGTTGACACCTCTGAATGATAGCAGCCTCGACTTG
521 LysLysHisSerThrGluGlyValLysLeuThrProLeuAsnAspSerSerLeuAspLeu 540
                         1630                    1650                     1670
                           .                       .                        .
    TCTATGGACAGTGACAACAGCATGTCTGCCTTCACCTACTAGTGCTATGAAGACCAGT
541 SerMetAspSerAspAsnSerMetSerValProSerProThrSerAlaMetLysThrSer 560
```

FIG. 2a.

```
          10                  30                  50
CATATGAGCTCTCAAAAGTTTTTGGTATTACTGGACCTGTTTCCACCGTGGGCCACA
          MetSerSerGlnLysValPheGlyIleThrGlyProValSerThrValGlyAlaThr
               70                  90                 110
GCAGCAGAAAATAAATTAAATGATAGTTTAATCCAAGAACTGAAAAAGAAGGATCGTTC
AlaAlaGluAsnLysLeuAsnAspSerLeuIleGlnGluLeuLysLysGluGlySerPhe
               130                 150                 170
GAAACAGAGCAAGAAACTGCCAATAGGGTACAAGTGTTGAAAATATTGCAGGAATTGGCA
GluThrGluGlnGluThrAlaAsnArgValGlnValLeuLysIleLeuGlnLeuLeuAla
               190                 210                 230
CAAAGATTTGTTTATGAAGTATCGAAGAAAAAATGTCAGACGCGGATGCCAAGGAT
GlnArgPheValTyrGluValSerLysLysLysAsnMetSerAspGlyMetAlaArgAsp
               250                 270                 290
GCTGGTGGGAAGATTTTTACGTAGTGTCTTATAGACTAGGAGTCCATGGGCCTGGTAGT
AlaGlyGlyLysIlePheThrTyrGlySerTyrArgLeuGlyValHisGlyProGlySer
               310                 330                 350
GATATCGATACTTTGGTAGTGTTCCAAAACATGTAACTCGGGAAGATTTTTTACGGTA
AspIleAspThrLeuValValValProLysHisValThrArgGluAspPhePheThrVal
               370                 390                 410
TTTGATTCACTACTGAGAGAGGAAGAACTGGATGAAATCGCACCTGTACCTGATGCG
PheAspSerLeuLeuArgGluArgGluArgLysGluLeuAspGluIleAlaProValProAspAla
               430                 450                 470
TTTGTCCCGATTATCAAGATAAAGTTCAGTGGTATTTCTATCGATTTAATCTGTGCACGT
PheValProIleIleLysIleLysPheSerGlyIleSerIleAspLeuIleCysAlaArg
               490                 510                 530
CTAGACCAACCTCAAGTGCCTTTATCCTTGACTTTATCAGATAAAAATCTACTGCGAAAT
LeuAspGlnProGlnValProLeuSerLeuThrLeuSerAspLysAsnLeuLeuArgAsn
               550
```

FIG. 2a-1.

```
                        550                              570                              590
CTAGACGAGAAGGAGACTTGAGAGCTTTGAATGGTACCAGGGTAACAGATGAGATATTAGAA
LeuAspGluLysAspLeuArgAlaLeuAsnGlyThrArgValThrAspGluIleLeuGlu
                       610                              630                              650
CTGGTACCAAAGCCGAATGTTTCAGAATCGCTTTAAGAGCTATTAAGCTATGGGCCCAA
LeuValProLysProAsnValPheArgIleAlaLeuArgAlaIleLysLeuTrpAlaGln
                       670                              690                              710
AGAAGGGCTGTTTATGCTAATATTTTGGTTTTCCTGGTGGTGGCTTGGGCCATGCTA
ArgArgAlaValTyrAlaAsnIlePheGlyPheProGlyGlyValAlaTrpAlaMetLeu
                       730                              750                              770
GTGGCTAGAATTTGTCAACTATACCCTAACGCCCTGTAGCGCAGTTATATTGAACAGATTT
ValAlaArgIleCysGlnLeuTyrProAsnAlaCysSerAlaValIleLeuAsnArgPhe
                       790                              810                              830
TTCATCATTTGTCGAATGGAATTGGCCACAACCTGTATCTTGAAACCAATTGAGGAT
PheIleIleLeuSerGluTrpAsnTrpProGlnProValIleLeuLysProIleGluAsp
                       850                              870                              890
GGCCCGTTACAAGTTCGTGTATGGAATCCAAAGATATATGCCCAAGACAGGTCTCACAGA
GlyProLeuGlnValArgValTrpAsnProLysIleTyrAlaGlnAspArgSerHisArg
                       910                              930                              950
ATGCCCGTCATTACACCAGCTTACCATCCATCAATGTGCTACCATAACATCACGGAATCT
MetProValIleThrProAlaTyrProSerMetCysAlaThrHisAsnIleThrGluSer
                       970                              990                             1010
ACTAAAAAAGTCATTTTACAGGAATTCGTAAGAGGCGTTCAAATTACGAATGATATTTTT
ThrLysLysValIleLeuGlnGluPheValArgGlyValGlnIleThrAsnAspIlePhe
                      1030                             1050                             1070
TCCAATAAGAAGTCCTGGGCCAATTTATTCGAAAAAACGATTTTTCTTCGATACAAG
SerAsnLysSerTrpAlaAsnLeuPheGluLysAsnAspPhePheArgTyrLys
                      1090                             1110                             1130
```

FIG. 2a-2.

```
TTCTATTAGAAATTACTGCATATACAAGGGGCAGTGACGAGCAGCATTAAAATGGAGT
PheTyrLeuGluIleThrAlaTyrThrArgGlySerAspGluGlnHisLeuLysTrpSer
     1150                              1170                      1190

GGTCTTGTTGAAAGTAAGGCTTCTAGTTATGAAACTGGAGTGTTAGCTGGAATA
GlyLeuValGluSerLysValArgLeuLeuValMetLysLeuValLeuAlaGlyIle
     1210                       1230                     1250

AAAATTGCACATCCTTTCACCAAACCCTTTGAAAGTAGTTATTGTGTCCAACCGAGGAT
LysIleAlaHisProPheThrLysProPheGluSerSerTyrCysCysProThrGluAsp
     1270                       1290                       1310

GACTATGAAATGATTCAAGACAAATACGGTAGTCATAAAACTGAGACAGCACTGAACGCC
AspTyrGluMetIleGlnAspLysTyrGlySerHisLysThrGluThrAlaLeuAsnAla
     1330                       1350                       1370

CTTAAACTGGTAACAGATGAAAATAAAGAGGAAGAAGTATTAAAGATGCACCAAAGCA
LeuLysLeuValThrAspGluAsnLysGluGluGluValIleLysAspAlaProLysAla
     1390                       1410                       1430

TATTTAAGCACCATGTACTACATAGGCCCTTGACTTTAATATTGAAAACAAAAGGAAAAAGTT
TyrLeuSerThrMetTyrIleGlyLeuAspPheAsnIleGluAsnLysLysGluLysVal
     1450                       1470                       1490

GACATTCACATTCCCTGCACTGAATTGTGTGAATTTATGTCGAAGTTTCAATGAGGATTAT
AspIleHisIleProCysThrGluPheValAsnLeuCysArgSerPheAsnGluAspTyr
     1510                       1530                       1550

GGTGACCACAAAGTATTCAATCTAGCCCCTCCGCTTCGTAAAGGTTACGATTGCCAGAT
GlyAspHisLysValPheAsnLeuAlaLeuArgPheValLysGlyTyrAspLeuProAsp
     1570                       1590                       1610

GAAGTTTCGATGAAAATGAAAAGAGACCATCAAAGAAGAGTAAAGAAGAATTAGAT
GluValPheAspGluAsnGluLysArgProSerLysLysSerLysLysAsnLeuAsp
     1630                       1650                       1670

GCTAGACATGAAACCGTGAAGATCTAAATCAGATGCTCTTCAGGTGACAACATCAAT
AlaArgHisGluThrValLysArgSerLysSerAspAlaAlaSerGlyAspAsnIleAsn
```

```
                                                    1710                          1730
GGCACAACCGCAGCTGTTGACGTAAACTAAGACATTCCTATTTATAGTTGAATAGTTTAT
GlyThrThrAlaAlaValAspValAsn
         1750                          1770                          1790
TAATATAGGTTAATCAGTCATAAACAAACTTGTACCCTTTTTTTTGAATCAAAGTACCTT
         1810
TTTTACGGCCCCGGGGGATCTC
```

```
CTCGAGCATTTTCGACTATTAGAGGATTCAAGTATCTATGAATTCTCTGAAGCTATCA
         10              30              50
TACTATCCTCTGGACGATATTAGAACGATTTTTCAAGTGAAACGTTTTAGCAAAAGTTTA
         70              90             110
AAGACACTAAACTAGCTAAATAATTTCACTGTGAGCAAGTCTTTAAACGGTCTTTTTGA
        130             150             170
ATCAAAAGAGGCCTAGAATTAACGCAAAATATTTAACGCATAAAGTTTTTTTAGACAAATAA
        190             210             230
                                                              M
TGAGCTCTCAAAAGGTTTTTGGTATTACTGGACCTGTTTCCACCGTGGGGCCACAGCAG
        250             270             290
etSerSerGlnLysValPheGlyIleThrGlyProValSerThrValGlyAlaThrAlaA
        310             330             350
CAGAAAATAAATTAAATGATAGTTTAATCCAAGAACTGAAAAAGGAAGGATCGTTCGAAA
        370             390             410
laGluAsnLysLeuIleGlnLeuIleGlnLeuLysLysGluLysLysGluLysSerPheGluT
CAGAGCAAGAAACTGCCAATAGGGTACAAGTGTTGAAAATATTGCAGGAATTGGCACAAA
        430             450             470
hrGluGlnGluThrAlaAsnArgValGlnValLeuLysIleLeuGlnLeuLeuAlaGlnA
GATTGTTTATGAAGTATCGAAGAAGAAAAATATGTCAGACGGATGGCAAGGATGCTG
        490             510             530
rgPheValTyrGluValSerLysLysLysAsnMetSerAspGlyMetAlaArgAspAlaG
GTGGGAAGATTTTACGTATGGTCTTATAGAGTCCATGGGCCTGGTAGTGATA
        550             570             590
lyGlyLysIlePheThrTyrGlySerTyrArgLeuGlyValHisGlyProGlySerAspI
TCGATACTTGGTAGTGTTCCAAAACATGTAACTCGGGAAGATTTTTTACGGTATTTG
        610             630             650
leAspThrLeuValValValProLysHisValThrArgGluAspPheThrValPheA
ATTCACTACTGAGAGAGAGGAAGGAACTGGATGAAATCGCACCTGTACCTGATGCGTTTG
```

FIG. 2b-1.

```
spSerLeuLeuArgGluArgLysGluLeuAspGluIleAlaProValProAspAlaPheV
TCCCGATTATCAAGATAAAGTTCAGTGGTATTTCTATCGATTAATCTGTCACGTCTAG
       690                    710
alProIleIleLysPheSerGlyIleSerIleAspLeuIleCysAlaArgLeuA
       730                    750                    770
ACCAACCTCAAGTGCCTTTATCCTTGACTTTATCAGATAAAAATCTACTGCGAAATCTAG
spGlnProGlnValProLeuSerLeuThrLeuSerAspLysAsnLeuLeuArgAsnLeuA
       790                    810                    830
ACGAGAAGGACTTGAGAGCTTTGAATGGTAACCAGGTAACAGATGAGATATTAGAACTGG
spGluLysAspLeuArgAlaLeuAsnGlyThrArgValThrAspGluIleLeuGluLeuV
       850                    870                    890
TACCAAAGCCGAATGTTTCAGAATGCTTTAAGAGCTATTAAGCTTAAGCTTAAGCTGCCCAAAGAA
alProLysProAsnValPheArgIleAlaLeuArgAlaIleLeuLysLeuTrpAlaGlnArgA
       910                    930                    950
GGGCTGTTTATGCTAATATTTTTGGTTTTCCTGGTGGTTGGCCATGCTAGTGG
rgAlaValTyrAlaAsnIlePheGlyPheProGlyGlyValAlaTrpAlaMetLeuValA
       970                    990                    1010
CTAGAATTGTCAACTATACCCTAACGCCTGTAGCGCAGTTATATTGAACAGATTTTCA
laArgIleCysGlnLeuTyrProAsnAlaCysSerAlaValIleLeuAsnArgPheI
       1030                   1050                   1070
TCATTTTGTCGGAATGAATTGGCCACAACCTGTTATCTTGAAACCAATTGAGGATGGCC
leIleLeuSerGluTrpAsnTrpProGlnProValIleLeuLysProIleGluAspGlyP
       1090                   1110                   1130
CGTTACAAGTTCGTGTGTATGGAATCCAAAGATATATGCCAAGACAGGTCTCACAGAATGC
roLeuGlnValArgValTrpAsnProLysIleTyrAlaGlnAspArgSerHisArgMetP
       1150                   1170                   1190
CCGTCATTACACCAGCTTACCCATCAATGTGTCTACCCATAACATCACGGAATCTACTA
roValIleThrProAlaTyrProSerMetCysAlaThrHisAsnIleThrGluSerThrL
```

FIG. 2b-2.

```
                          1210                          1230                          1250
AAAAGTCATTTACAGGAATTCGTAAGAGGCGTTCAAATTACGAATGATATTTTCCA
ysLysValIleLeuGlnGluPheValArgGlyValGlnIleThrAsnAspIlePheSerA
                          1270                          1290                          1310
ATAAGAAGTCCTGGGCCAATTTATTCGAAAAAAACGATTTTTCTTTCGATACAAGTCT
snLysLysSerTrpAlaAsnLeuPheGluLysAsnAspPhePheArgTyrLysPheT
                          1330                          1350                          1370
ATTTAGAAATTACTGCATATACAAGGGCAGTGACGAGCAGCATTTAAAATGGAGTGGTC
yrLeuGluIleThrAlaTyrThrArgGlySerAspGluGlnHisLeuLysTrpSerGlyL
                          1390                          1410                          1430
TTGTTGAAAGTAAGGTAAGGCTTCTAGTTATGAAACTGGAGGTGTTAGCTGGAATAAAAA
euValGluSerLysValArgLeuLeuValMetLysLeuValLeuAlaGlyIleLysI
                          1450                          1470                          1490
TTGCACATCCTTTCACCAAACCCTTTGAAAGTAGTTATTGTGTCCAACCGAGGATGACT
leAlaHisProPheThrLysProPheGluSerSerTyrCysCysProThrGluAspAspT
                          1510                          1530                          1550
ATGAAATGATTCAAGACAAATACGGTAGTCATAAAACTGAGACAGCACTGAACGCCCTTA
yrGluMetIleGlnAspLysTyrGlySerHisLysThrGluThrAlaLeuAsnAlaLeuL
                          1570                          1590                          1610
AACTGGTAACAGATGAAAATAAAGAGGAAGAAAGTATTAAAGATGCACCAAAGGCATATT
ysLeuValThrAspGluAsnLysGluGluSerIleLysAspAlaProLysAlaTyrL
                          1630                          1650                          1670
TAAGCACCATGTACATAGGCCTTGACTTTAATATTGAAACAAAAGAAAAAAGTTGACA
euSerThrMetTyrIleGlyLeuAspPheAsnIleGluAsnLysLysGluLysValAspI
                          1690                          1710                          1730
TTCACATTCCCTGCACTGAATTTGTGAAGTTTCAATGAGGATTATGGTG
leHisIleProCysThrGluPheValAsnLeuCysArgSerPheAsnGluAspTyrGlyA
```

```
                    1750                         1770                      1790
ACCACAAAGTATTCAATTCTAGCCCTCCGCTTCGTAAAGGGTTACGATTTGCCAGATGAAG
spHisLysValPheAsnLeuAlaLeuArgPheValLysGlyTyrAspLeuProAspGluV
            1810                         1830                      1850
TTTCGATGAAAATGAAAAGAGACCATCAAAGAAGAGTAAAAGAAGAATTTAGATGCTA
alPheAspGluAsnGluLysArgProSerLysLysSerLysArgLysAsnLeuAspAlaA
            1870                         1890                      1910
GACATGAAACCGTGAAGAGATCTAAATCAGATGCTGCTTCAGGTGACAACATCAATGGCA
rgHisGluThrValLysArgSerLysSerAspAlaAlaSerGlyAspAsnIleAsnGlyT
            1930                         1950                      1970
CAACCGCAGCTGTTGACGTAAACTAAGACATTCCTATTTATAGTTGAATAGTTTATTAAT
hrThrAlaAlaValAspValAsn
            1990                         2010                      2030
ATAGGTTAATCAGTCATAAACAAACTTGTACCCTTTTTTTGAATCAAAGTACCTTTTTT
                    2050                         2070                      2090
ACGAAGCAGTAAAACGTTTACGAGATTCTCTACATATGCTCTTTCGCGTGTAGCGACA
                    2110                         2130                      2150
TTTTACCATTAGGTGAGAATTTGTGTTACAAGCTGGATGTCAGGATGATACCTTTGAAG
                    2170                         2190                      2210
GCATAGTTAAATTGGCTGGGAAAGGAACGGAACCTTTTCCTTTCCGAGTTTCGGCCAGAT
                    2230                         2250                      2270
ATTTAGGCTTTTTTTTTTTCTGACGGAATAGGGGACCCAGGATTGACAAATATAACAAAAC

AAGCTT
```

*FIG. 2b-3.*

| | | | | | |
|---|---|---|---|---|---|
| 1 | MSSQKVFGIT | GPVSTVGATA | AENKLNDSLI | QELKKEGSFE | TEQETANRVQ |
| 51 | VLKILQELAQ | RFVYEVSKKK | NMSDGMARDA | GGKIFTYGSY | RLGVHGPGSD |
| 101 | IDTLVVVPKH | VTREDFFTVF | DSLLRERKEL | DEIAPVPDAF | VPIIKIKFSG |
| 151 | ISIDLICARL | DQPQVPLSLT | LSDKNLLRNL | DEKDLRALNG | TRVTDEILEL |
| 201 | VPKPNVFRIA | LRAIKLWAQR | RAVYANIFGF | PGGVAWAMLV | ARICQLYPNA |
| 251 | CSAVILNRFF | IILSEWNWPQ | PVILKPIEDG | PLQVRVWNPK | IYAQDRSHRM |
| 301 | PVITPAYPSM | CATHNITEST | KKVILQEFVR | GVQITNDIFS | NKKSWANLFE |
| 351 | KNDFFFRYKF | YLEITAYTRG | SDEQHLKWSG | LVESKVRLLV | MKLEVLAGIK |
| 401 | IAHPFTKPFE | SSYCCPTEDD | YEMIQDKYGS | HKTETALNAL | KLVTDENKEE |
| 451 | ESIKDAPKAY | LSTMYIGLDF | NIENKKEKVD | IHIPCTEFVN | LCRSFNEDYG |
| 501 | DHKVFNLALR | FVKGYDLPDE | VFDENEKRPS | KKSKRKNLDA | RHETVKRSKS |
| 551 | DAASGDNING | TTAAVDVN | | | |

AspIleHisIleProCysThrGluPheValAsnLeuCysArgSerPheAsnGluAspTyr

GlyAspHisLysValPheAsnLeuAlaLeuArgPheValLysGlyTyrAspLeuProAsp

GluValPheAspGluAsnGluLysArgProSerLysLysSerLysArgLysAsnLeuAsp

AlaArgHisGluThrValLysArgSerLysSerAspAlaAlaSerGlyAspAsnIleAsn

GlyThrThrAlaAlaValAspValAsn

```
         V   F   G   I   T   G   P   V   S   T   V   G   A   T
      5' GTGTTTGGGATAAC..........ACGGTGGGGCCGACG 3'
            A   C   A     T              A   A   A   A
            T   T   T     C              T   T   T   C
            C   C   C                    C   C   C
      CC--┐                                         ┌--CC
        ECoRI└----------------→            ←--------┘SalI
                                                  SalI

⇨

EcoRI                                              SalI
   5' CCGAATTCGTGTTTGGGATAACTGGACCCTGTTTCCACGGTGGGGCCGACGGTCGACGG 3'
                A   C   A     T              A   A   A   A
                T   T   T     C              T   T   T   C
                C   C   C                    C   C   C
```

FIG. 4.

| PEPTIDE: | SEQUENCE |
|---|---|
| N-TERMINUS | PFPVTTQGSQQTQPXQKXYG |
| 101 | TDEILHLVPNIDNFRLTLRAIKLXAK |
| 96 | THNIYSNILGFLGGVSXAMLVAR |
| 66 | QRLEWVGLVESK |

FIG. 15a.

```
NNCTGGATTCCGTCCACTGAGGCGGGAGGGGGGGCCTGCCTCAGCCCTGGGCGGGCACGGCGGGTTGCGGGGGGAAGTGACTG
                                                                        90
NNGACCTAAGGCAGGTGACTCCGCCCCTCCCTCCCCCCCGAGTCGGGACCCGCTGCCGCCGCCAACGCCCCCCTTCACTGAC

TrpIleProSerThrGluAlaGlyGlyArgGlyAlaSerAlaLeuGlyGlyThrAlaAlaValAlaAlaGlyGlyLys  Leu
   GlyPheArgProLeuArgArgArgGlyGlyGlyGlyGlyGlnProTrpAlaAlaArgArgLeuArgArgGlyArgSerTrp
LeuAspSerValHis   GlyGlyArgGluGlyAlaCysLeuSerProGlyArgHisGlyGlyCysGlyGlyGluValThrGly

ProAsnArgGlySerProProProArgGly   GlyGlnAlaAlaArgArgArgAsnArgProProLeuSerGln
  SerGluThrTrpGlnProProLeuSerProProAlaGlnArgLeuGlyProArgCysProProProGlnProProSerThrValPro
  GlnIleGlyAspValSerAlaProProGlyAlaGluAlaArgProProValAlaAlaThrAlaProProPheHisSerPro

GGCGGTGCGGCGCCGAGACGATGCCGTTTCCAGTTACAACAGGATCACACAGGTGTTGTTTGTGTTGGCGGTGTCTTCGTGATACCGTAATGA
                                                                       180
CCGGCCACGCGCCCTCTGCTACGGCAAGGTCAATGTTGTCTCCTAGTGTTGTTTGTGTTGGCGGTGTCTTCGTGATACCGTAATGA

Translation Start
                             →

GlyGlyAlaAlaProGluThrMetProPheProValThrThrGlnGlySerGlnGlnThrGlnProProGlnLysHisTyrGlyIleThr
AlaValArgArgArgArgCysArgPheGlnLeuGlnHisArgAspHisAsnLysHisAsnArgHisArgSerThrMetAlaLeuLeu
ArgCysGlyAlaGlyAspAlaValSerSerTyrAsnThrGlyIleThrThrAsnThrThrAlaThrGluAlaLeuTrpHisTyrPhe

AlaThrArgArgLeuArgHisArgLysTrpLeuArgLysCysSerLeuSer    LeuLeuCysLeuLeuArgTrpLeuLeuValIleAlaAsnSer
ArgHisProAlaProSerSerAlaThrGluLeu    LeuValProIleValPheValValAlaValSerAlaSerHisCys    Lys
  ProAlaAlaGlySerValIleGlyAsnGlyThrValValCysProAspCysCysValCysGlyGlyCysPheCys    ProMetValGlu

TCTCCTATCAGCTTAGACAGCCCCCAAGGAGAGACTGCTACTTACACAGAAACTAATTGAGACATTGAAACCCTTTGGGGTTTTTGAA
                                                                       270
AGAGGATAGTCGAATCGTCGGGGGTTCCTCTGACTGACGCATGAATGTGTCTTTGATTAACTCTGTAACTTGGGAAACCCCAAAACTT

SerProIleSerLeuAlaAlaProLysGluThrAspCysValLeuThrGlnLysLeuIleGluThrLeuLysProPheGlyValPheGlu
LeuLeuSerAla    GlnProProArgArgLeuThrAlaTyrLeuHisArgAsn    LeuArgHis    AsnProLeuGlyPheLeuLys
  SerTyrGlnLeuSerSerProGlnGlyAsp    LeuArgThrTyrThrGluThrAsn    AspIleGluThrLeuTrpGlyPhe    Arg

ArgArgAspAla    CysGlyGlyLeuSerValAlaTyrLysCysLeuPhe    AsnLeuCysGlnPheGlyLysProAsnLysPhe
Glu    SerLeuLeuGlyTrpProSerGlnSerArgVal    ValSerValLeuGlnSerMetSerValArgGlnProLysGlnLeu
  GlyIleLeuLysAlaAlaGlyLeuSerValSerGlnThrSerGlnValCysPheSerIleSerValCysPheGlyLysProThrLysSerSer
```

FIG. 15b.

```
GAGGAAGAGAACTGCAGCGCAGGATTTTATTTGGGAAAAACTAAATAACCTGGTAAAAGAGTGGATACGACAAATCAGTGAAAGCAAG
                                                                               360
CTCCTTCTCTTGACGTCGCGTCCTAAAAATAAAACCCTTTGATTATTGGACCATTTCTCACCTATGCTGTTAGTCACTTTCGTTC
GluGluGluLeuGlnArgArgIlePheIleLeuGlyLysLeuAsnAsnLeuValLysGluTrpIleArgGluIleSerGlyLys
ArgLysArgAsnCysSerAlaGlyPheLeuPheThrGlyGluAsn  IleThrTrp   LysSerGlyTyrGluLysSerValLysAlaArg
GlyArgGlyThrAlaAlaGlnAspPheTyrPheGlyLysThrLys    ProGlyLysArgValAspThrArgAsnGln   LysGlnGlu

LeuPheLeuPheGlnLeuAlaProAsnLysAsnGlnSerPhe    IleValGlnTyrPheLeuProTyrSerPheAspThrPheAlaLeu
ProLeuProValAlaAlaAlaCysSerLys    LysProPheValLeuTyrGlyProLeuLeuThrSerValLeuPhe    HisPheCysSer
SerSerSerSerCysArgLeuIleLysIleLysProPheSerPheLeuArgSerHisIleArgSerIleLeuSerLeuLeuPhe

AATCTTCCACAATCTGTAATTGGAGGAAAAATTTTACATTGGATCTTACAGATTAGGAGTGCATACAAAAGGTGCTGAT
                                                                               450
TTAGAAGGTGTTAGACATTAACTTTACAACCTCCTTTTAAAAATGTAAACCTAGAATGTCTAATCCTCACGTATGTTTCCAGACTA

AsnLeuProGlnSerValIleGluAsnValGlyGlyLysIlePheThrPheGlySerTyrArgLeuGlyValHisThrLysGlyValAlaAsp
IlePheHisAsnLeu    LeuLysMetLeuGlyLysPheLeuHisLeuAspLeuThrAsp    GluCysIleGlnLysValLeuIle
SerSerThrIleCysAsn    LysCysTrpArgLysAsnPheTyrIleLeuGlnIleArgSerAlaTyrLysArgCys    Tyr

IleLysTrpLeuArgTyrAsnPheIleAsnSerSerPheAsnLysCysLysSerArgValSer    SerHisMetCysPheThrSerIle
AspGluValIleGlnLeuGlnPheHisGlnLeuPheLys    MetGlnIleLysCysIleLeuLeuAlaTyrLeuLeuHisGlnTyr
ArgGlyCysAspThrIleSerProPheThrProProPheIleLysValAsnProAsp    LeuAsnProThrCysValPheProAlaSerIle

ATTGATGCGTTGTGTGTTGCACCAACACATGTTGATCGAAGTGACTTTTTCACCTCATTCTATGATAAGTTGAAATTACAGAAGAAGTA
                                                                               540
TAACTACGCAACACAACGTGGTTGTGTACAACTAGCTTCACTGAAAAAGTGGAGTAAGATACTATTCAACTTTAATGTCCTTCTTCAT

IleAspAlaLeuCysValAlaProThrHisValAspArgSerAspPhePheThrSerPheTyrAspLysLeuLysLeuGlnGluVal
LeuMetArgCysValLeuHisGlnHisMetLeuIleGluValThrPheSerProHisSerMetIleSer    AsnTyrArgLysLys
    CysValValCysCysThrAspThrCys    SerLys   LeuPheHisLeuIleLeu     ValThrIleThrGlyArgSerLys

AsnIleArgGlnThrAsnCysTrpCysMetAsnIleSerThrValLysGluGly    GluIleIleLeuGlnPhe   LeuPhePheTyr
GlnHisThrThrHisGlnValLeuValHisGlnAspPheHisSerLys    ArgMetArgHisTyrThrSerIleValProLeuLeuLeu
SerAlaAsnHisThrAlaGlyValCysThrSerArgLeuSerLysLysValGluAsn    SerLeuAsnPheAsnCysSerSerThrPhe
```

FIG. 15C.

```
AAAGATTTAAGAGCTGTTGAAGAGGCATTCGTACCAGTTATTAAACTCTGTTTGATGGGATAGAGATTGATATTTGTTGCAAGATTA
                                         ◊                             ◊                   630
TTTCTAAATTCTCGACAACTTCTCCGTAAGCATGGTCAATAATTTGAGACAAAACTACCCTATCTCTAACTATAAAACAAACGTTCTAAT

LysAspLeuArgAlaValGluGluAlaPheValProValIleLysLysCysPheAspGlyIleIleAspIleLeuPheAlaArgLeu
LysIle    GluLeuLeuLysArgHisSerTyrGlnLeuLeuAsnSerValLeuMetGly      ArgLeuIlePheCysLeuGlnAsp
  ArgPheLysSerCys   ArgGlyIleArgThrSerTyr    ThrLeuPhe    TrpAspArgAsp    TyrPheValCysLysIleSer

PheIle    SerSerAsnPheLeuCysGluTyrTrpAsnAsnPheGluTyrLysIleProTyrLeuAsnIleAsnGlnLysCysSer
  LeuAsnLeuLeuGlnGlnLeuProMetArgValLeu    ValArgAsnGlnHisSerLeuSerGlnTyrLysThrGlnLeuIleLeu
    SerLysLeuAlaThrSerSerAlaAsnThrGlyThrIleLeuSerGlnLysSerProIleSerIleSerIleLysAsnAlaLeuAsnAla

GCACTGCAGACAATTCCTGAAGATTGGATCTACGAGATGATGACAGTCTGCTAAAAAATTTAGATATAAGAGTTATAAGAAGTCTTAACGGT
                                    ◊                            ◊                        720
CGTGACGTCTGTTAAGGACTTCTAAACCTAGATGCTCTACTACTGTCTCAGACGATTTTAAATCTATATATTCTACATATTCTTCAGAATTGCCA

AlaLeuGlnThrIleProGluAspLeuAspSerLeuLeuLysAsnLeuAsnIleArgCysIleArgSerLeuAsnGly
  HisCysArgGlnPheLeuLysIleTrpIleTyrGluMetThrValCys    LysIle    Ile    AspVal    GluValLeuThrVal
    ThrAlaAspAsnSer    ArgPheGlySerThrArg    GlnSerAlaLysPheArgTyrLysMetTyrLysLysSer    ArgLeu

CysGlnLeuCysAsnArgPheIleGlnIle     SerIleValThrGln    PheIle    IleTyrSerThrTyrSerThrLysValThr
  ValAlaSerLeuGlyGluGlnLeuAsnProAspValLeuHisCysAspAlaLeuPheAsnLeuTyrLeuIleTyrLeuPheAsp    ArgAsn
    SerCysValIleGlySerSerLysSerArgArgSerArgSerPheLysSerIleLeuHisIleLeuArgLeuArgLeuProGln

TGCAGGGTAACCGATGAAATTTACATCTAGTACCAAACATTGACACTCAGGTTAACTCTGAGAGCTATCAAACTATGGGCCAAACGC
                                     ◊                            ◊                       810
ACGTCCCATTGGCTACTTTAAAATGTAGATCATGGTTTGTAACTGTTGAAGTCCAATTGAGACTCTCGATAGTTGATACCGGTTTGCG

CysArgValThrAspGluIleLeuHisLeuValProAsnIleAspAsnPheArgLeuThrLeuArgAlaIleLysLeuTrpAlaLysArg
  AlaGly    ProMetLysPheTyrIle    TyrGlnThrLeuThrThrSerGly    Leu    GluLeuSerAsnTyrGlyProAsnAla
    GlnGlyAsnArg    AsnPheThrSerSerThrLysHis    GlnLeuGlnValThrAsnSerGluSerTyrGlnThrMetGlyGlnThrPro

AlaProTyrGlyIlePheAsn    Met    TyrTrpValAsnValValGluPro    SerGlnSerSerAspPhe    ProGlyPheAla
  CysProLeuArgHisPheLysValAspLeuValLeuCysGlnCysSer    ThrLeuGluSerLeu    ValIleProTrpValGly
    LeuThrValSerSerIleLysCysArgThrGlyPheMetSerLeuLysLysAlaIleLeuAsnValArgLeuAlaIleLeuSerHisAlaLeuArgTrp
```

```
CATACTGTTTAGTGAACTCCTTAGTTTTTTTGGTTGAGGTAATGAATGAACCCCCTTGATTTTCTCCCGATCTAACTGAACTC
                                                                                1440
GTATGACAAATCACTTGAGGAATCAAAAAAACCAACTCCATTACACTTGGGGGAAACTAAAAAGACGGGCTAGATTGACTTGAG

HisThrValLeuValAsnSerLeuValPhePheGly    GlyAsnGluCysGluProProLeuIlePheLeuProAspLeuThrGluLeu
IleLeuPhe    ThrPro  PhePheLeuValTGluValMetAsnValAsnProLeu   PhePheCysProIle   LeuAsnSer
TyrCysPheSerGluLeuSerPhePheTrpLeuArg       Met    ThrPhoPheAspPheSerAlaArgSerAsn    ThrPro

MetSerAsn   HisValGly   AsnLysLysThrPheThrIlePheThrPheGlyArgIleAsnLysGlyIle   SerPheGlu
TyrGlnLysLeuSerSerArgLeuLysLysGlnAsnLeuTyrHisIleHisValGlyLysSerLysGluAlaArgAspLeuGlnValGly
ValThrLysThrPheGluLysThrLysLysProGlnProLeuSerHisSerGlyGlyLysIleLysArgGlySerArgValSerSerArg

CTGCTACATTTGTAGCAACATAAGTTCTGAGGCATACATCAGTCATGACAAAAACAGTACATCTGTATACAGTGGCAAGTGGATGCACC
                                                                                1530
GACCATGTAAACATCGTTGTATTCAAGACATCCGTATGTCAGTCAGTAGTAGACATATGTCACCGTTCACCTACGTGG

LeuLeuHisLeu   GlnHisLysPheCysArgHisThrSerValMetThrLysThrValHisLeuTyrThrValAlaSerGlyCysThr
CysTyrIleCysSerSerAsnIleSerSerValGlyIleHisGlnSer   GlnLysGlnTyrIleCysIleGlnTrpGlnValAspAlaPro
AlaThrPheValAlaThr    ValLeu    AlaTyrIleSerHisAspLysAsnSerThrSerValTyrSerGlyLysTrpMetHisPro

Gln    MetGlnLeuLeuMetLeuGluThrProMetCys    AspHisCysPheCysTyrMetGlnIleCysHisCysThrSerAlaGly
AlaValAsnThrAlaValTyrThrArgTyrAlaTyrMetLeu    SerLeuPheLeuValAspThrTyrLeuProLeuHisIleCysGly
SerCysLysTyrCysCysLeuAsnGlnLeuCysValAspThrMetValPheValThrCysArgTyrValThrAlaLeuProHisValArg

CTGAAAAATCTGTAGTAATAATTCTCTGCTAAGAAACAGTATTTTATCTAATTCTGGAAACTCATTAATTGCTAGGAATCTTAAAAC
                                                                                1620
GACTTTTTAGACATCAATTATTAAGAGACGATTCTTGTCATAAAAATAGATTAAGACCTTTGAGTAATTAACGATCCTTAGAAATTTTG

LeuLysAsnLeu   LeuIleIleCys   GluThrValPheLeuSerAsnSerGlyAsnSerLeuIleAlaArgAsnLeu   Asn
      LysIleCysSer    PheSerAlaLysLysGlnTyrPheTyrLeuIleLeuGluThrHis    LeuLeuGlyIleLysThr
GluLysSerValValTAsnAsnSerLeuLeuArgAsnSerIlePheIle    PheTrpLysLeuIleAsnCys    GluSerLeuLysGln

GlnPheIleGlnLeu    TyrAsnGluAlaLeuPheCysTyrLys    ArgIleArgSerVal       AsnSerProIleLysLeuVal
SerPheAspThrPheLeuGluArgSerLeuPheLeuIleLysIle    AsnGlnPheSerMetLeuGln    SerAspLysPheCys
PhePheArgTyrAsnIleIleArgGln    SerValThrAsnLysAspPheGluProPheGluAsnIleAlaLeuPhe    PheLeu
```

FIG. 15g.

```
AAGACAAAGCTAATAATAAATCTCAATATATAGCCAATTAAATGTTTCAATAGTTACAGCACATTATTGGCCTGCCATTTCCCCAATG
                                                                                    1710
TTTCTGTTTGATTATTTACAGTTATATATCGGTTAATTTACAAAGTTATCAATGTCGTGTAATAACCGGACGGTAAAAGGGGGTTAC

LysAspLysAlaAsnLysMetSerIleTyrSerGlnLeuAsnValPheSerIleValThrAlaHisTyrTrpProAlaIlePheProGlnCys
LysThrLysLeuIleLysCysGlnTyrIleAlaAsn  MetPheSerIleValThrAlaHisTyrTrpProAlaIlePheProGlnCys
ArgGlnSer    AsnValAsnIle   ProIleLysCysPheGln   LeuGlnHisIleIleGlyLeuProPheSerProAsnVal

PheValPheSerIlePheHis   TyrIleAlaLeu    IleAsnGluIleThrValAlaCys    GlnGlyAlaMetLysGlyTrpHis
LeuCysLeu   TyrPheThrLeuIleTyrGlyIleLeuHisLys   TyrAsnCysCysMetTheProArgGlyAsnGluGlyLeuThr
SerLeuAlaLeuLeuIleAspIleTyrLeuTrpAsnPheThrLysLeuLeu   LeuValAsnAsnAlaGlnTrpLysGlyIleAsn

TTATAGCCCCTTCAAATATTTCTACAGCTAGCTTTCATCAATCTAAGTGGGTGTTAATCATGTTAATTCATGTTAAATATAATGGTTT
                                                                                    1800
AATATCGGGGAAGTTTATAAAGATGTCGATGGAAAGTACTTAGATTCACCCACAATTAGTACAATTAAGTACCAAATTTATATTACCAAA

Leu  ProLeuGlnIlePheLeuGlnLeuAlaPheMetAsnLeuSerGlyCys   SerCys   PheMetVal   Ile   TrpPhe
      TyrSerProPheLysTyrPheTyrSer   LeuSer   Ile   ValGlyValAsnHisValAsnSerTrpPheLysTyrAsnGlyLeu
      IleAlaProSerAsnIleSerThrAlaSerPheHisGlySerLysTrpValLeuIleMetLeuIleHisGlyLeuAsnIleMetVal

LeuGlyLysLeuTyrLys    Leu   SerGluHisIle   ThrProThrLeu   ThrLeuGluHisAsnLeuTyrLeuProLys
        IleAlaGlyGluPheIleGluValAlaLeuLys   SerAspLeuHisThrAsnIleMetAsnIle   ProLysPheIleIleThr
        TyrGlyArg   IleAsnArgCysSerAlaLysMetPheArgLeuProHis   AspHis   AsnMetThr   IleTyrHisAsnLeu

AATACCTTAGTACAGGTTAAAAGCTTCATTAGTGTTAGTTTGATGAAAAATGTAAGTTATAATCTTATTTAAAAAACAGACAAACC
                                                                                    1890
TTATGGAATCATGTCCAATTTCGAAGTAATAACACTACTTTTACATTCAATATTAGAATAAATTTTTGTCTGTTTGG

AsnThrLeuValGlnValLysSerPheIleAsnCysValSerPheAspGluLysCysLysLeu   SerTyrLeuLysAsnArgGlnThr
IlePro   TyrArgLeuLysAlaSerLeuIleValLeuMetLysAsnValSerTyrAsnLeuIle   LysThrAspLysPro
TyrLeuSerThrGly   LysLeuHis   LeuCys   Phe   LysMet   ValIleLeuPheLysLysGlnThrAsnHis

IleGly   TyrLeuAsnPheAlaGluAsnIleThrAsnThrLysIlePhePheThrLys   LeuArgIle   PheValSerLeuGly
TyrArgLeuValPro   PheSer   AsnHis   AsnGlnHisPheIleTyrThrIleLysAsnLeuPheCysValPheTrp
ValLysThrCysThrLeuLeuLysMetLeuGlnThrLeuLysSerPheHisLeuAsnTyrAsp   LysPhePheLeuCysValVal
```

FIG. 15h.

```
ACAGACTTGCACTTTATTTGCCCTGGGCTGAAATGTGCCAAAGTCCCACTTAAAATTTTTGTTAATGCTTGAAGCTTTTCTGACCAT
                                                                                  1980
TGTCTGAAGTGAAAATAAACGGGACCGACTTTCAGGGTGAATTTAAAAAACAATTACGAACTTCGAAAAGACTGGTA
```

ThrAspLeuHisPheTyrLeuProTrpAlaGluAsnValProLysPheValAsnAla   SerPheSerAspHis
GlnThrCysThrPheIleCysProGlyLeuLysMetCysGlnSerProThr   AsnPheLeuLeuMetLeuGluAlaPheLeuThrIle
ArgLeuAlaLeuLeuPheAlaLeuGly   LysCysAlaLysValProLeuLysIlePheCys   CysLeuLysLeuPhe   ProPhe

CysValGlnValLysIleGlnGlyProSerPheIleHisTrpLeuGlyVal   PheLysLysAsnIleSerSerAlaLysArgValMet
LeuSerAlaSerLysAsnAlaArgProGlnPheHisAlaLeuThrGlySerLeuIleLysGln   HisLysPheSerLysGlnGlyAsn
SerLysCysLys   LysGlyGlnAlaSerPheThrGlyPheAspTrpLysPheAsnLysThrLeuAlaGlnLeuLysGluSerTrpLys

TTGATCTTGTGTGTTGGAATGGTGTTTTGTAATAATCTAAGCAAGATTGCTTTATGCTCTTCCCCAATTAAAAACAAGAATTATGACCTTCAA
                                                                                  2070
AACTAGAACACAACCTAACACAAAACATTATTAGATTCGTTCTAACGAAATACGAGAAGGGTTAATTTTGTTCTTAATACTGGAAGTT

LeuIleLeuCysTrpIleValPheCysAsnAsnLeuSerLysIleAlaLeuCysSerProIleLysAsnLysAsnTyrAspLeuGln
   SerCysValGlyLeuCysPheValIleIle   AlaArgLeuLeuTyrAlaLeuProGlnLeuLysThrArgIleMetThrPheLys
   AspLeuValLeuAspCysPheMetLeuPheProAsn   LysGlnGluLeu   ProSerLys

GlnAspThrProAsnHisLysThrIleIle   AlaLeuAsnSer   AlaArgGlyTrpAsnPheValLeuIleIleValLysLeu
SerArgThrAsnSerGlnThrLysTyrTyrAspLeuCysSerGlnLysIleSerLysGlyLeu   PheCysSerAsnHisGlyGluPhe
   IleLysHisGlnIleThrAsnGlnLeuArgLeuLeuIleAlaLysHisGluGlyIleLeuPheLeuPhe   SerArg   Phe

```
AAAAAAAAAAAAAAAAAAAAAAAAAAAAAAAAAAAAAAAAAAAA
                                                                                  2160
TTTTTTTTTTTTTTTTTTTTTTTTTTTTTTTTTTTTTTT
```

LysLysLysLysLysLysLysLysLysLysLysLysLysLysLys
LysLysLysLysLysLysLysLysLysLysLysLysLysLysLysLysLys
LysLysLysLysLysLysLysLysLysLysLysLysLysLysLysLysLys

PhePhePhePhePhePhePhePhePhePhePhePhePhePhePhe
PhePhePhePhePhePhePhePhePhePhePhePhePhePhePhe
PhePhePhePhePhePhePhePhePhePhePhePhePhePhePhe

FIG. 16a.

TRANSLATION START

ATGCCGTTTCCAGTTACAACACAGGGATCACAACAAACCGCCACACAGAAGCACTAT

M  P  F  P  V  T  T  Q  G  S  Q  Q  T  Q  P  P  Q  K  H  Y

GGCATTACTTCTCCTATCAGCTTAGCAGCCCCCAAGGAGACTGACTGCGTACTTACACAG

G  I  T  S  P  I  S  L  A  A  P  K  E  T  D  C  V  L  T  Q

AAACTAATTGAGACATTGAAACCCTTTGGGGTTTTTGAAGAGGAAGAGGAACTGCAGCGC

K  L  I  E  T  L  K  P  F  G  V  F  E  E  E  E  E  L  Q  R

AGGATTTTTATTTTGGGAAAACTAAATAACCTGGTAAAAGAGTGGATACGAGAAATCAGT

R  I  F  I  L  G  K  L  N  N  L  V  K  E  W  I  R  E  I  S

GAAAGCAAGAATCTTCCACAATCTGTAATTGAAAATGTTGGAGGAAAAATTTTTACATTT

E  S  K  N  L  P  Q  S  V  I  E  N  V  G  G  K  I  F  T  F

```
GGATCTTACAGATTAGGAGTGCATACAAAGGTGCTGATATTGATGCCTTGTGTGTTGCA
 G  S  Y  R  L  G  V  H  T  K  G  A  D  I  D  A  L  C  V  A

CCAACACATGTTGATCGAAGTGACTTTTTCACCTCATTCTATGATAAGTTGAAATTACAG
 P  T  H  V  D  R  S  D  F  F  T  S  F  Y  D  K  L  K  L  Q

GAAGAAGTAAAAGATTTAAGAGCTGTTGAAGAGGCATTCGTACCAGTTATTAAACTCTGT
 E  E  V  K  D  L  R  A  V  E  E  A  F  V  P  V  I  K  L  C

TTTGATGGGATAGAGATTGATATTTTGTTTGCAAGATTAGCACTGCAGACAATTCCTGAA
 F  D  G  I  E  I  D  I  L  F  A  R  L  A  L  Q  T  I  P  E

GATTTGGATCTACGAGATGACAGTCTGCTAAAAAATTTAGATATAAGATGTATAAGAAGT
```

```
CTTAACGGTTGCAGGGTAACCGATGAAATTTTACATCTAGTACCAAACATTGACAACTTC
 L  N  G  V  A  G  N  R  D  E  I  L  H  L  V  P  N  I  D  N  F

AGGTTAACTCTGAGAGCTATCAAACTATGGGCCAAACGCCACAACATCTATTCCAATATA
 R  L  T  L  R  A  I  K  L  W  A  K  R  H  N  I  Y  S  N  I

TTAGGTTTCCTCGGTGGTGTTTCCTGGGCTATGCTAGTAGCAAGAACTTGCCAGCTTTAT
 L  G  F  L  G  G  V  S  W  A  M  L  V  A  R  T  C  Q  L  Y

CCAAATGCAATAGCATCAACTCTTGTACATAAATTTTTCTTGGTATTTTCTAAATGGAA
 P  N  A  I  A  S  T  L  V  H  K  F  F  L  V  F  S  K  W  E

TGGCCAAATCCAGTGCTATTGAAACAGCCTGAAGAATGCAATCTTAATTTGCCTGTATGG
 W  P  N  P  V  L  L  K  Q  P  E  E  C  N  L  N  L  P  V  W
```

(Note: amino acid translation above reflects best reading; first line begins with "D L D L R D D S L L K N L D I R C I R S")

GACCCAAGGGTAAACCCCAGTGATAGGTACCATCTTATGCCTATAATTACACCAGCATAC
D   P   R   V   N   P   S   D   R   Y   H   L   M   P   I   T   P   A   Y

CCACAACAGAACTCCACGTGTACCGTTTCAACACGGATGGTCATGGTTGAGGAG
P   Q   Q   N   S   T   Y   N   V   S   V   S   T   R   M   V   M   V   E   E

TTTAAACAAGGTCTTGCTATCACAGATGAAATTTGCTGAGTAAGGCAGAGTGGTCCAAA
F   K   Q   G   L   A   I   T   D   E   I   L   L   S   K   A   E   W   S   K

CTTTTTGAAGCTCCAAACTTCTTCAAAAGTACAAGTATGTATTTTAAGGCATGTCGGAC
L   F   E   A   P   N   F   F   Q   K   Y   K   Y   V   F   *
                                                        TRANSLATION STOP

ATGTTGCTCTCTTAAGTAATGGTTTAATGGTAGCACACATCATGACATTTCTTCTTGCTGGA

CTAATGTTATTGGAAGAATTTCTTCCCTGTCACAAGGACATACTGTTTTAGTGAACTCC

TTAGTTTTTTTTGGTTGAGGTAATGAATGTGAACCCCCTTTGATTTTTTCTGCCCGATCTA

ACTGAACTCCTGCTACATTTGTAGCAACATAAGTTCTGTAGGCATACATCAGTCATGACA

AAAACAGTACATCTGTAT
　　　　　　　Acc I

RECOMBINANT POLY(A) POLYMERASE

BACKGROUND OF THE INVENTION

This invention relates to cloning and expression of genes encoding a poly(A) polymerase, particularly a eucaryotic poly(A) polymerase.

Raabe et al., 353 Nature 229, 1991 describe the cloning and in vitro expression of bovine poly(A) polymerase. The gene encoding the polymerase was isolated and its nucleotide sequence determined. This nucleic acid was then expressed by translation in a reticulocyte lysate and shown to produce a poly(A) polymerase of apparent size 85k.

SUMMARY OF THE INVENTION

Applicant provides nucleic acid encoding eucaryotic poly(A) polymerases, including a yeast poly(A) polymerase, a human poly(A) polymerase and a bovine poly(A) polymerase. Applicant also demonstrates the expression in vivo of eucaryotic poly(A) polymerases, and provides various methods for use of such recombinant polymerases.

Thus, in a first aspect, the invention features purified nucleic acid encoding a yeast, a human, or a bovine poly(A) polymerase, where the bovine nucleic acid consists essentially of that nucleic acid sequence shown as SEQ. ID. NO.: 1 infra, also shown in FIG. 1. This bovine cDNA sequence differs at its 3'-end region from that described by Raabe et al., supra Equivalent such nucleic acids (and their encoded amino acid sequences) are also included in this invention. Such equivalents include nucleic acid which differs at one or more bases and yet still encodes the desired active poly(A) polymerase. Examples of such equivalents are provided below.

By "purified" is meant that the nucleic acid sequence is isolated from the environment in which it naturally occurs, that is, it is separated from one or more nucleotide sequences located nearby that encoding the poly(A) polymerase. Generally, such purified nucleic acid will be provided as a homogeneous preparation, for example, it may be provided in a vector and maintained in an aqueous solution or as a lyophilized preparation. In preferred embodiments, the nucleic acid is cDNA or its equivalent, and has a sequence selected from those listed as SEQ. ID. NOS.: 1 or 2 (also shown in FIGS. 1 and 2).

In a related aspect, the invention features purified nucleic acid encoding the amino acid sequence shown as SEQ. ID. NO.: 3 (also shown in FIG. 3). Most preferably, the preferred nucleic acid encodes enzymatically active poly(A) polymerase having poly(A) polymerase activity as defined by Wahle, 266 J. Biol. Chem. 3131, 1991. When the nucleic acid is provided within a vector, it preferably is transcriptionally linked to a promoter sequence located adjacent the purified nucleic acid adapted to control expression of the nucleic acid. Expression from that promoter causes production of enzymatically active poly(A) polymerase.

In a related aspect, the invention features recombinant poly(A) polymerase produced from recombinant nucleic acid. Preferably the recombinant poly(A) polymerase is purified. Applicant is the first to enable production of any such poly(A) polymerase, including eucaryotic enzymes, in particular in useful levels having greater than $10^4$, preferably $10^5$ or $10^6$ U/mg (Lingner et al., 266 J. Biol. Chem 8741, 1991).

By "recombinant" is meant that the poly(A) polymerase is not produced by naturally-occurring nucleic acid but rather by nucleic acid that has been manipulated by one or more procedures to position that nucleic acid either within a vector or at a location in a genome in which it does not naturally occur. The recombinant poly(A) polymerase differs from that which naturally occurs since it exists in an environment in which it does not naturally occur, and may be chemically distinct from previously purified poly(A) polymerase e.g., that described by Wahle, 266 J. Biol. Chem. 3131, 1991. Preferably, the recombinant poly(A) polymerase is purified after its production, and thus separated from essentially all contaminants, e.g., RNAse, with which it naturally occurs in nature. Most preferably, the poly(A) polymerase is produced in a cell in which it does not naturally occur, and purified from that cell. Such a purified enzyme necessarily differs from that purified from nature since it is associated with different low levels of contaminating chemicals which are not removed by the purification procedures. Such preparations of poly(A) polymerase are novel and not described in the art.

In preferred embodiments recombinant poly(A) polymerase is eucaryotic, for example, yeast, bovine or human, and is purified to the extent that it produces a single homogeneous band in a standard polyacrylamide gel when observed after Coomassie blue or even silver staining.

In a related aspect, the invention features a method for production of recombinant poly(A) polymerase by providing recombinant nucleic acid encoding that polymerase, having a promoter sequence upstream from the nucleic acid. The nucleic acid is present within the genome of a living cell or within an autonomously replicating vector in a living cell. The poly(A) polymerase is produced from the promoter and thereby expression of the poly(A) polymerase within the cell established.

By "living cell" is meant to include a cell which can replicate and divide either within a living organism or within an in vitro (e.g., cell culture) system. (It does not include extracts from living cells e.g., oocyte extracts.) Such cells will include bacterial cultures, for example, of *Escherichia coli*, or yeast and various mammalian cell cultures.

In preferred embodiments, the poly(A) polymerase is eucaryotic, e.g., yeast, bovine or human, and the cell in which the poly(A) polymerase is expressed is bacterial, for example, *E. coli*. Preferably, the vector is selected from a plasmid, cosmid, phage, or phasmid, and the nucleic acid being expressed lacks any 5'-untranslated sequences which are naturally associated with a nucleic acid encoding the poly(A) polymerase. Applicant believes that these sequences may be detrimental to expression of the poly(A) polymerase. Most preferably, the nucleic acid consists essentially of that shown as SEQ. ID. NOS.: 1 or 2.

In further preferred embodiments, the method includes purifying the poly(A) polymerase expressed from the nucleic acid by passing that poly(A) polymerase over a [DEAE] diethylaminoethyl column, or its equivalent, to separate non-eucaryotic poly(A) polymerase from the desired eucaryotic poly(A) polymerase; and further may include purifying that polymerase over a hydroxyapatite column, and or a [mono-S] cationic exchange resin column or equivalent columns.

In other aspects, the invention features methods for use of the recombinant poly(A) polymerase or even its native equivalent, for example, (a) providing a poly(A) tail on a ribozyme by contacting a poly(A) polymerase with the ribozyme in the presence of adenosine triphosphate (ATP)

under poly(A) polymerizing conditions; (b) labelling the 3'-end of an RNA molecule by contacting the recombinant poly(A) polymerase with an RNA molecule in the presence of a labelled adenosine derivative under poly(A) polymerizing conditions. Examples of useful adenosine derivatives are those which allow only a single molecule to be incorporated by the poly(A) polymerase, for example, cordicepin-triphosphate or dideoxyadenosine triphosphate; (c) blocking the 3'-end of an RNA molecule with a 3' or 2'3' deoxy ATP (such a blocked RNA is less susceptible to degradation in vivo and is thus stabilized); (d) a method for cDNA synthesis by providing a poly(A) tail on an RNA molecule (to be reverse transcribed) by contacting that RNA molecule with recombinant poly(A) polymerase in the presence of ATP triphosphate under poly(A) polymerizing conditions to form poly(A)-tailed RNA which can be used to form cDNA; (e) a method for translating RNA in a reticulocyte lysate by providing a poly(A)-tail on that RNA and then translating the poly(A)-tailed RNA in the lysate; (f) synthesis of labelled poly(A) by contacting labelled ATP with recombinant poly(A) polymerase in the presence of unlabelled RNA or oligoA or poly(A) as a primer under poly(A) polymerizing conditions to form the labelled poly(A); (g) PCR applications; and (h) polyadenylating any RNA molecule by contacting that RNA molecule with the poly(A) polymerase in the presence of ATP under poly(A) polymerizing conditions.

As can be determined from the above summary, applicant is the first to provide a yeast and human poly(A) polymerase, and is the first to provide a method by which eucaryotic poly(A) polymerases can be expressed in an in vivo system to provide recombinant poly(A) polymerase of sufficient quality and quantity to be useful in a variety of methods. The purity and activity, especially of the yeast poly(A) polymerase, makes it especially useful in these methods, and advantageous over prior methods which made use of non-recombinant poly(A) polymerase.

Other features and advantages of the invention will be apparent from the following description of the preferred embodiments thereof, and from the claims.

DESCRIPTION OF THE PREFERRED EMBODIMENTS

The drawings will first briefly be described. [Some of the following Figures are reproduced from publications to appear in Nature, Dec. 12, 1991 and EMBO Vol. 10(13) 1991 journals.]

Drawings FIG. 1 shows the nucleotide base sequence of cDNA encoding a bovine poly(A) polymerase and the corresponding amino acid sequence of a bovine poly(A) polymerase;

FIGS. 2A, 2A', 2A", 2A''', 2B, 2B', 2B" and 2B''' show the nucleotide base sequence of DNA encoding a poly(A) polymerase of Saccharomyces cerevisiae (yeast), specifically the insert sequence in pJPAP1 and genomic DNA respectively;

FIGS. 3A and 3B show the amino acid sequence (as one and three letter codes respectively) of the poly(A) polymerase of Saccharomyces cerevisiae;

FIG. 4 shows the primer design for PCR amplification of the poly(A) polymerase of yeast;

Figure 5A:
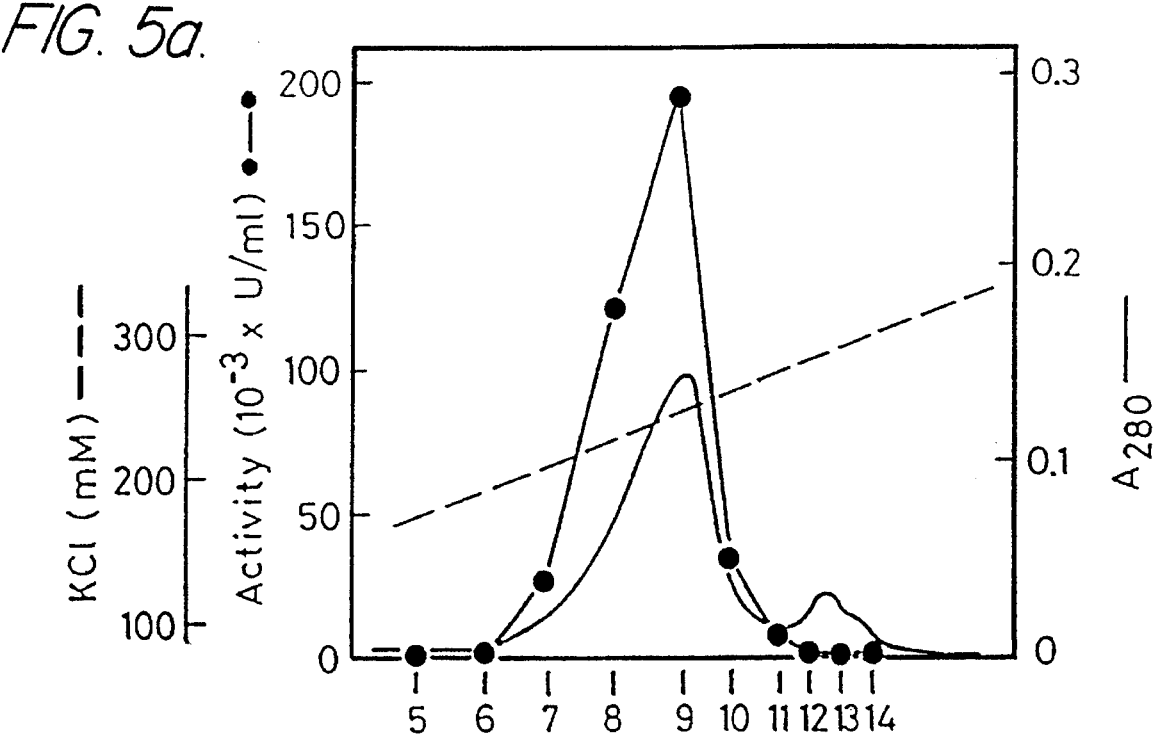
Figure 5B:
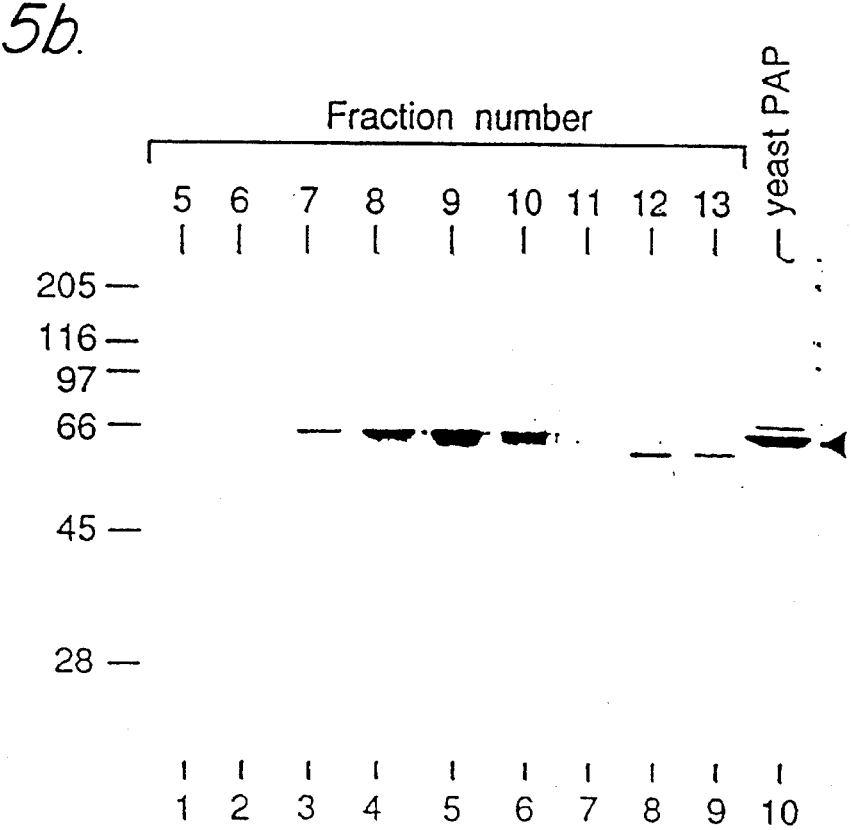
Figure 6A:
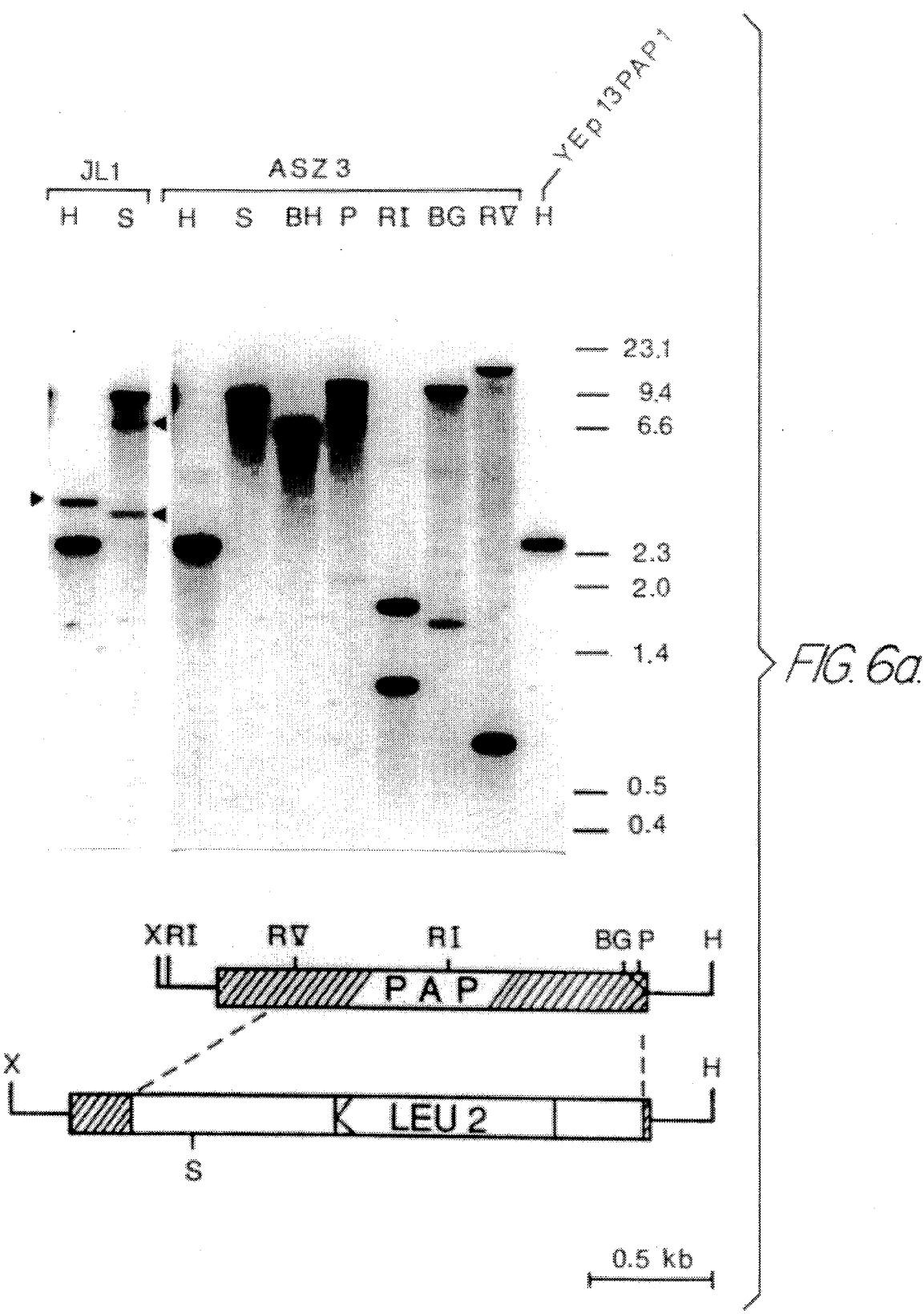

FIG. 5A is a graphical representation of the protein elution profile (solid line) of a poly(A) polymerase on a mono-S chromatography column, with salt gradient indicated by the dashed line, and activity of the enzyme by the solid circles (see, Lingner et al. 266 J. Biol. Chem. 8741, 1991);

FIG. 5B is a photograph of an electrophoretic separation of the mono-S fractions in a 10% polyacrylamide SDS gel with fraction numbers indicated above each lane (lanes 1–9), and lane 10 including the native poly(A) polymerase purified from yeast, with molecular mass of protein markers in kiloDaltons given at the left;

FIG. 6A (upper panel) is a photograph of a Southern blot analysis of chromosomal DNA of wild type yeast ASZ3 (a/α, ade2-1/ade2-1, his 3-11, 15/his 3-11, 15, leu 2 -3, 112/leu2-3,112, trp 1-1/trp1-1, uva 3/uva, 3 can 1-100/can 1-100); and JL1 (PAP1/PAP1::LCO2; for the construction of JL1, ASZ3 was transformed with pPAP LEU (linearized with XhoI and HindIII) by electroporation. pPAP LEU was constructed by deleting most of PAP1 with HindII and SnaBI and replacing this region with the 2.1 kb HpaI fragment of YEp13 which contains the entire LEU2 gene); and plasmid DNA of the isolated clone YEp13PAP1; DNA was digested with restriction enzymes, as indicated above each lane, and probed with the 2286 base pair XhoI-HindIII fragment covering the PAP1 coding region (shown in the lower panel). Restriction site abbreviations are B (BamHI), Sa (Sau3AI) H (HindIII), RV (EcoRI), BG (BglII), P (PvuII). The length of DNA markers is indicated in kb at the right. Arrowheads point to new restriction fragments resulting from the insertion of the LEU2 marker. The lower part of the lower panel indicates a fragment that was used for disruption of one PAP1 allele. The PAP1 region that was replaced by LEU2 is indicated by the broken lines.

Figures 6B, 7:
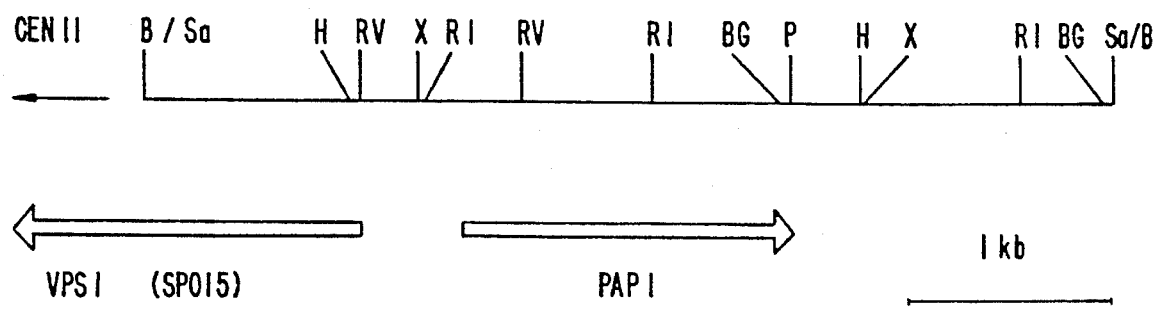

FIG. 6B is a restriction map of the isolated clone YEp13PAP1 containing the PAP1 gene. The arrows below the map indicate the direction of transcription and the extension of PAP1 and VPS1. The relative position of centromere 11 is indicated by the arrow;

FIG. 7 shows peptide sequences of purified native bovine poly(A) polymerase. Sequences of the N-terminus and three internal peptides (arbitrary numbering) are presented in the single letter code in their order of appearance in the predicted protein sequence (see FIG. 1). X represents an unidentified amino acid. The primers used for PCR amplification of cDNA fragments are indicated as arrows pointing in the 5' to 3' direction.

Figure 8:
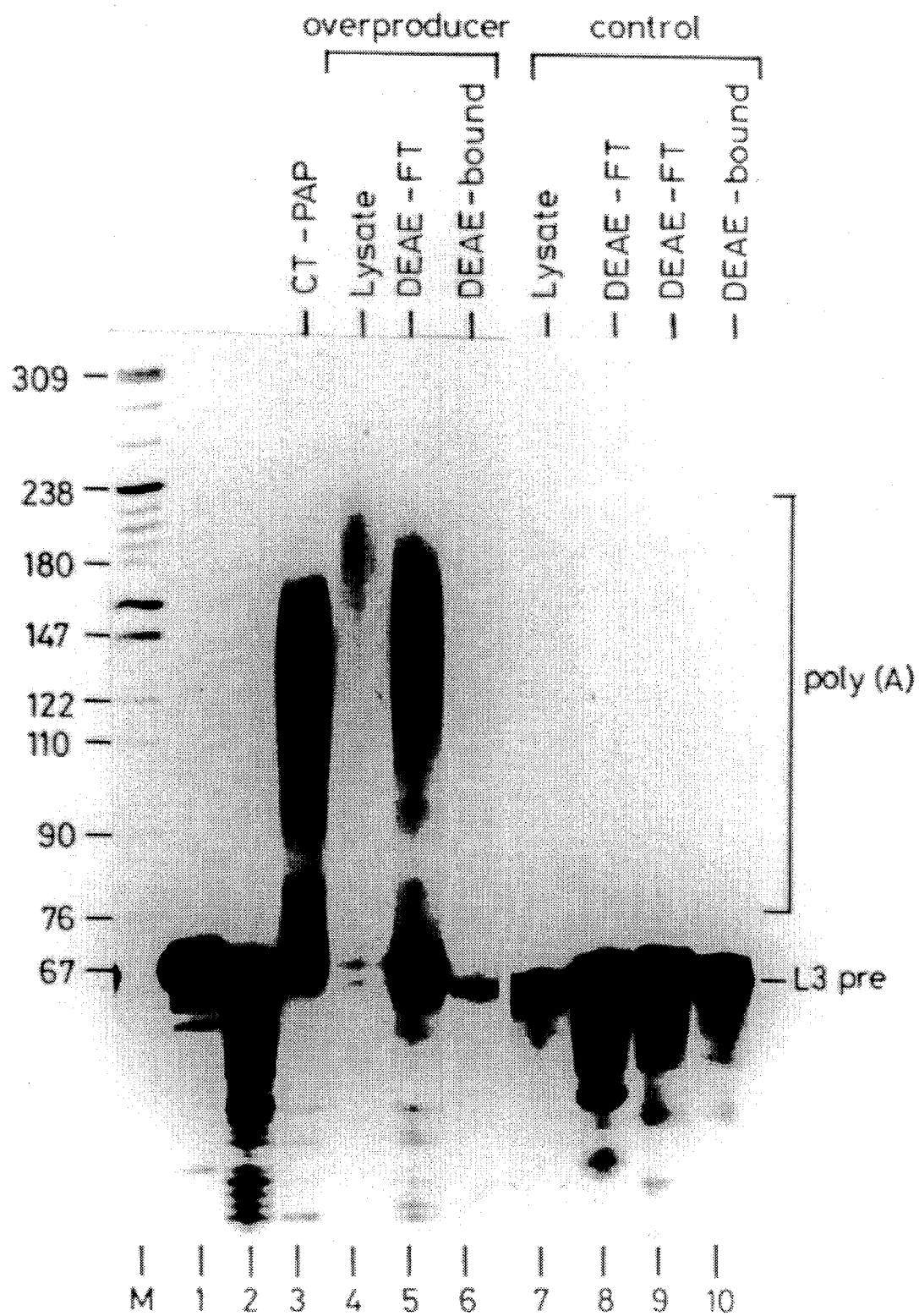
Figure 9:
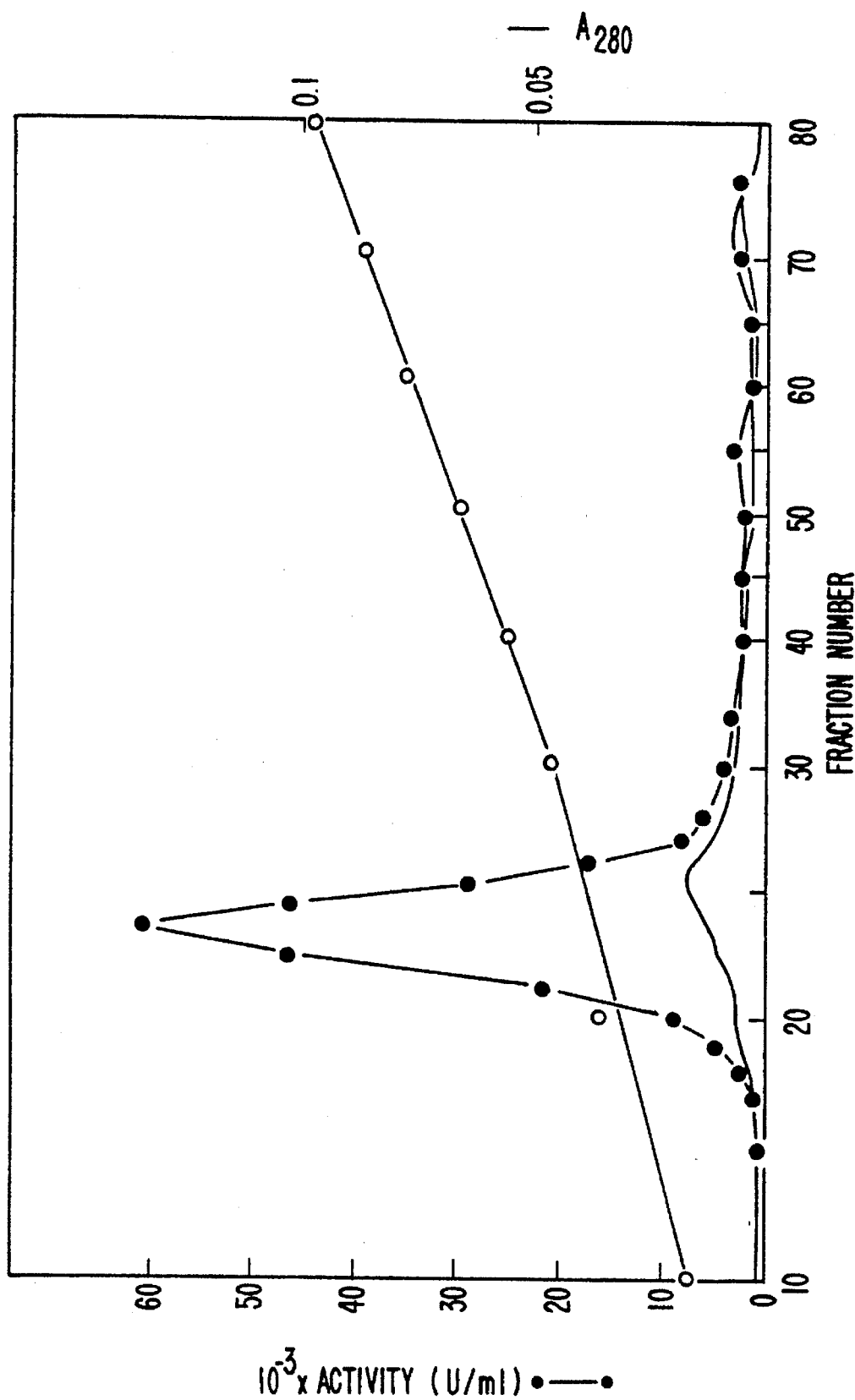
Figure 10:
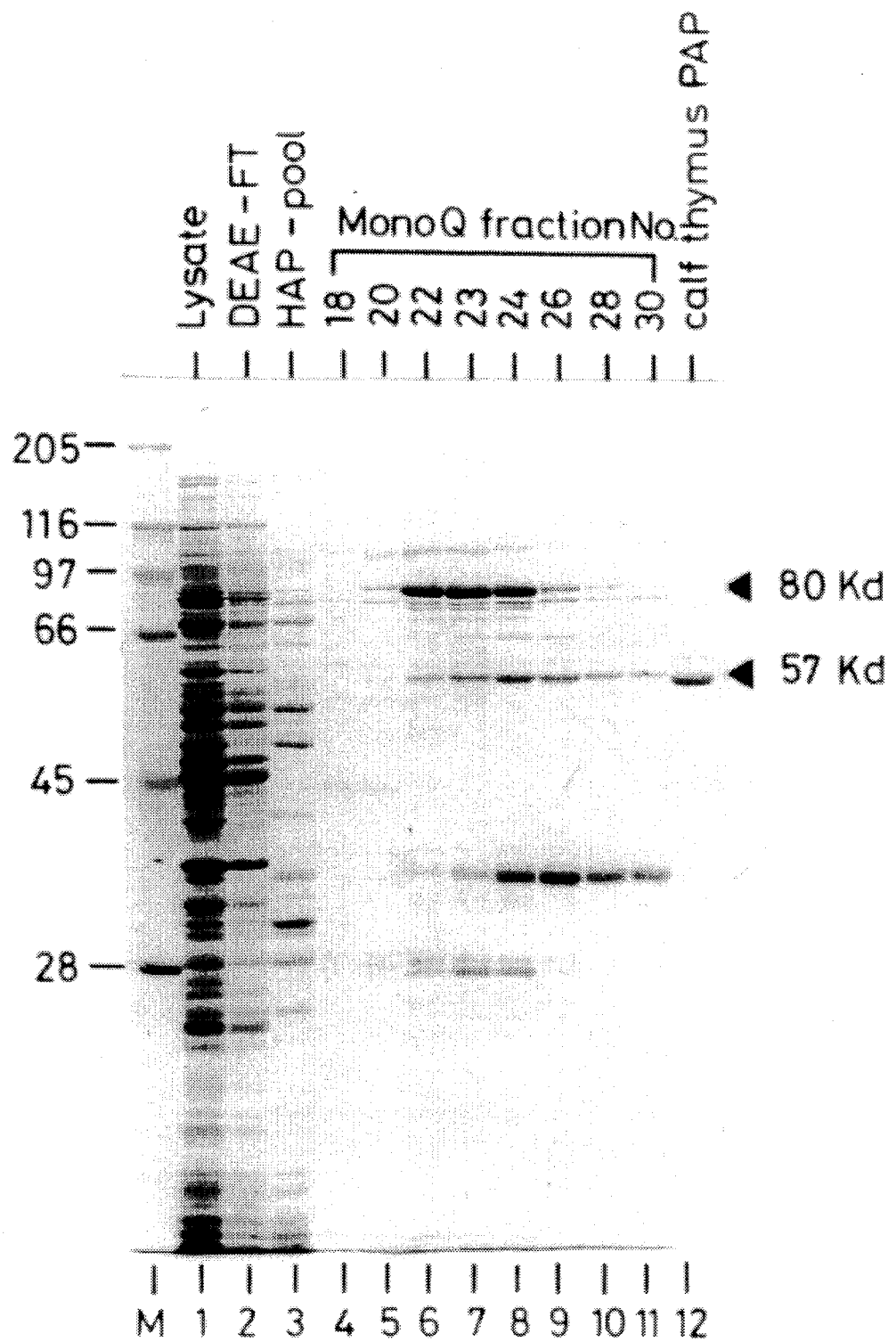
Figure 11:
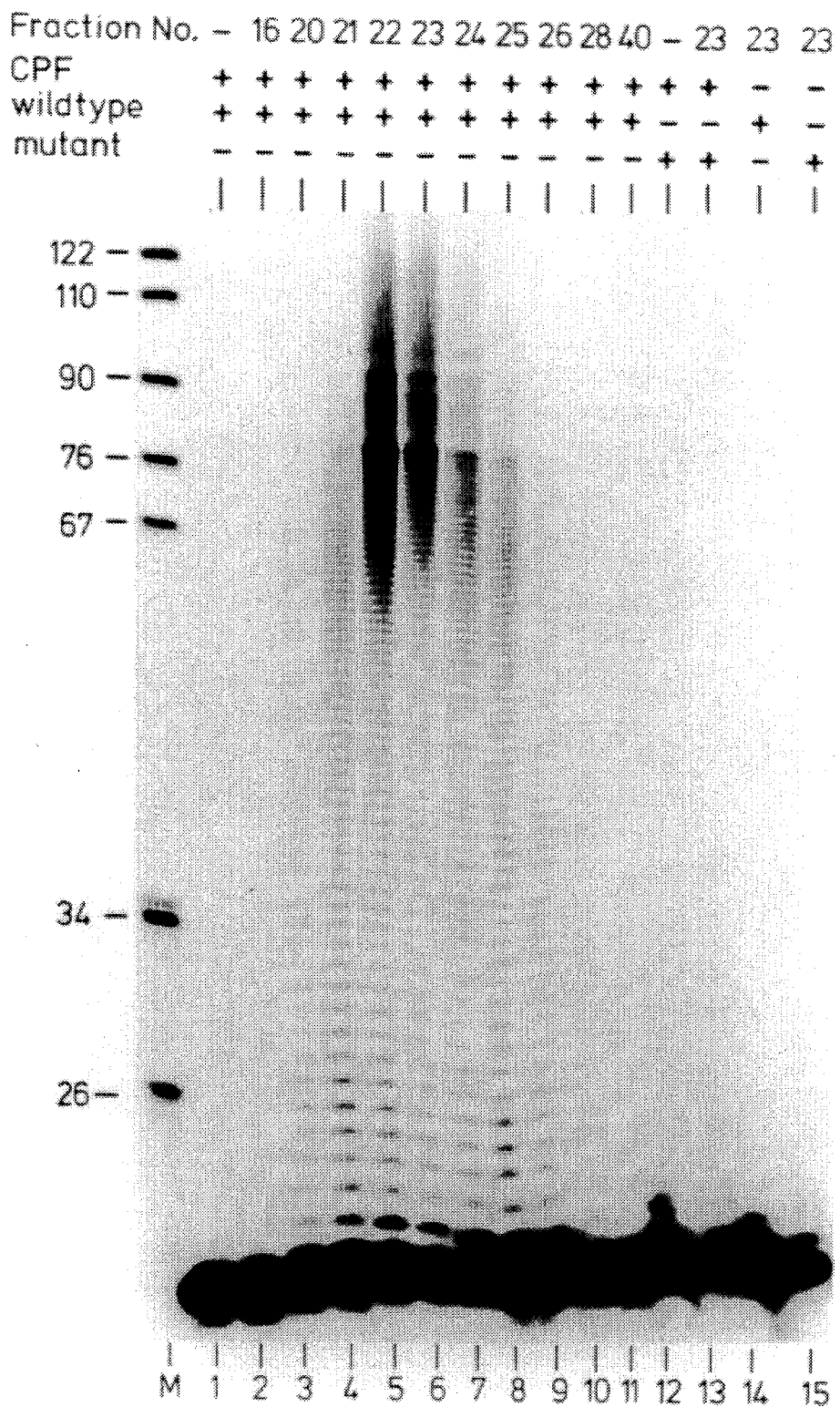
Figures 12A, 12B:
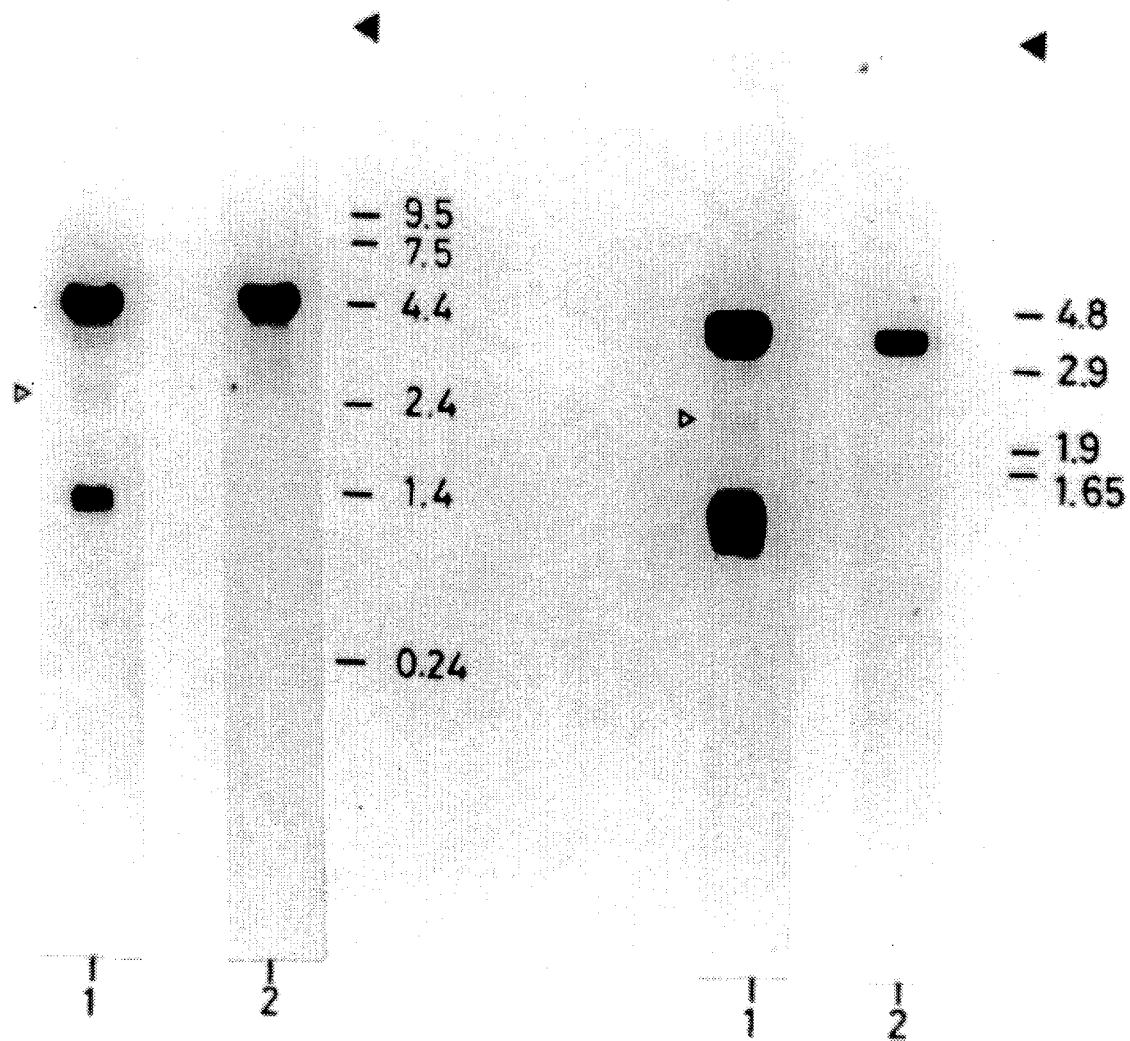
Figure 13:
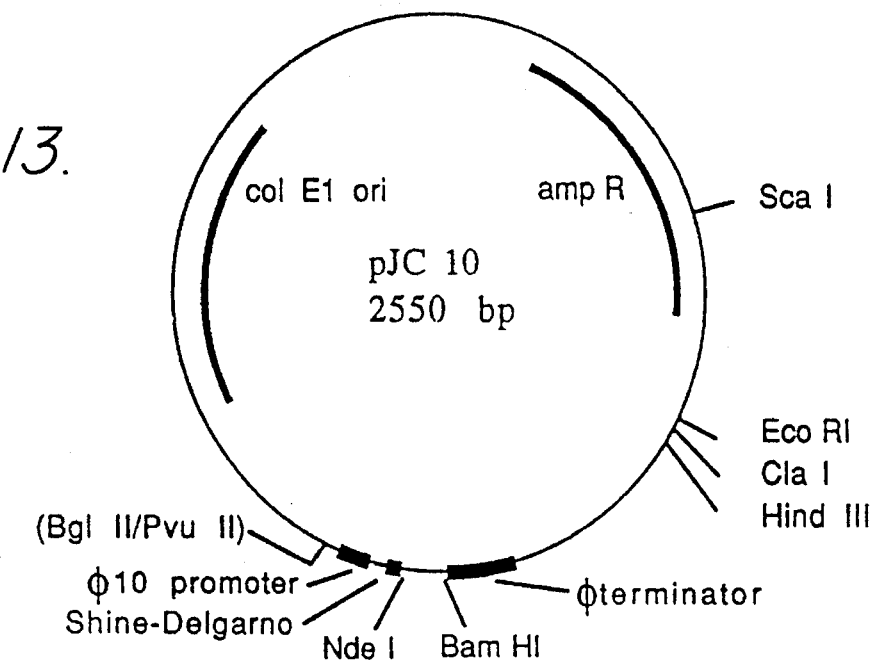
Figure 14:
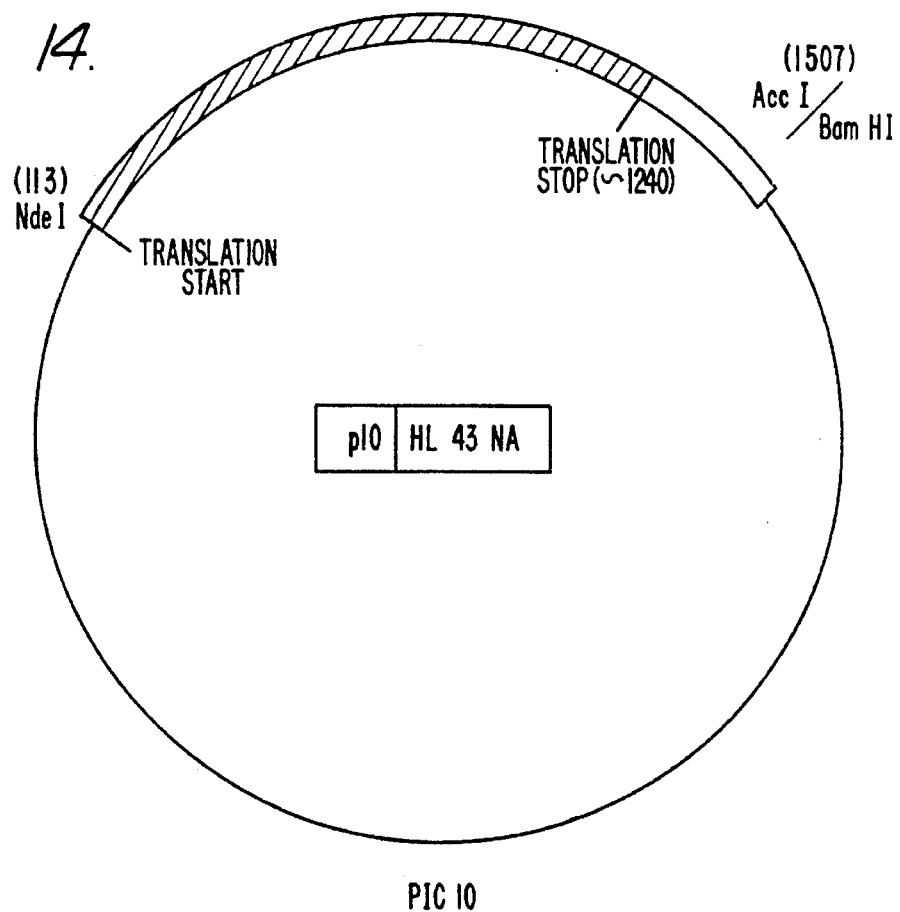

FIG. 8 is a photograph of a gel showing specific polyadenylation by E. coli-produced recombinant bovine poly(A) polymerase. Specific polyadenylation reactions were carried out with L3pre substrate RNA (see Wahle, supra). Lane 1, incubation with purified native calf thymus poly(A) polymerase (5 U) in the absence of CPF (see Wahle, supra); lane 2, incubation with CPF alone; lane 3, incubation with purified CPF plus purified recombinant bovine poly(A) polymerase. All reactions displayed in lanes 4–10 contained purified CPF plus various E. coli fractions. Lanes 4–6, fractions derived from overproducing strain (pT7-PAP82); lane 4, 300 ng of crude lysate (3.5 U poly(A) polymerase as defined by Wahle, supra); lane 5, 70 ng of DEAE flowthrough peak fraction (1.5 U); lane 6, 150 ng of DEAE-bound peak fraction (2 U). Lanes 7–10, fractions derived from control strain (pJC10); lane 7, 275 ng of crude lysate (1.5 U); lane 8, 35 ng of DEAE flowthrough peak fraction (0.25 U); lane 9, 670 ng of the same DEAE flowthrough peak fraction (5 U); lane 10, 150 ng of DEAE bound peak fraction (1.3 U). The RNA was run on a denaturing 12% polyacrylamide gel. Positions of substrate and polyadenylated products are indicated on the right. Poor recovery of RNA in lane 4 was very probably due to the presence of ribonucleases in the crude extract. M represents DNA size markers;

FIGS. 9, 10 and 11 are a graphical representation and copies of gels showing partial purification of E. coli-produced recombinant bovine poly(A) polymerase. Specifically, FIG. 9 shows the profile of a MonoQ column showing $A_{280}$, salt gradient and nonspecific poly(A) polymerase activity. The scale in which the peak fractions are presented differs from the scale in the rest of the column profile. FIG. 10 shows an SDS-PAGE of aliquots throughout the purification. Lane M, molecular weight markers; lane 1, 2.5 µl of lysate (375 U); lane 2, 2.5 µl of DEAE flowthrough (175 U); lane 3, 150 µl of the hydroxyapatite pool (750 U); lanes 4–11, 200 µl each of MonoQ fractions 18–30; lane 12, 1.2 µg of purified native calf thymus poly(A) polymerase. Electrophoresis was carried on a 10% polyacrylamide gel. Proteins were detected by staining with Coomassie Brilliant Blue. Numbers on the left indicate the molecular weights of marker proteins in kDa. Arrowheads point to the 80 kDa and 37 kDa polypeptides which copurified with poly(A) polymerase activity. FIG. 11 shows specific polyadenylation activity in the MonoQ column. Aliquots of column fractions (1 µl of 1:15 dilutions) were assayed with synthetic RNA 18mers, wild type or mutant as indicated. Assays were supplemented with purified CPF as indicated in the top panel. M shows DNA size markers. Samples were separated on a denaturing 12% acrylamide gel;

FIG. 12 is a copy of Northern blot analysis of mRNA encoding various poly(A) polymerases. Northern blotting was carried out with poly(A)$^+$ RNA from calf thymus or HeLa cells as indicated. The amounts of RNA loaded per lane were 4.5 µg for HeLa RNA, and 25 µg for calf thymus RNA. Exposure times were 2 weeks for HeLa RNA, and 2 days for calf thymus RNA. Probes were a fragment extending from a HindIII site in the polylinker of the vector to the KpnI site at position 975 (lanes 1), and a PvuII-EcoRI fragment (positions 1729–2235; lanes 2). Size markers were either those obtained from Gibco/BRL (calf thymus), or ribosomal RNAs from E. coli and calf thymus (HeLa). The empty arrowheads point to the weak 2.4 kb bands; full arrowheads indicate the loading wells;

FIG. 13 is a diagrammatic representation of plasmid pJC10 used for expression of yeast PAP1, described by Clos et al., 63 Cell 1085, 1990. It contains the ScaI-BglII fragment of pET3C (Rosenberg et al. 56 Gene 125, 1987) and the ScaI-PvuII fragment of pBluescript II KS+ (Stratagene, La Jolla, Calif.). The E. coli host used for expression was BL21 (DE3) pLysS (Studier, 219 J. Mol. Biol. 37, 1991);

FIG. 14 is a diagrammatic representation of plasmid p10/HL43NA for expression of recombinant human 43 Kd protein homologous to bovine poly(A) polymerase. It includes pJC10 ligated at its NdeI and BamHI sites to an NdeI-AceI fragment of human nucleic acid subcloned from a lambda gt11 cDNA library of Nielsen et al., 13 Nuc. Acid. Res. 6867, 1985;

Figure 15E:
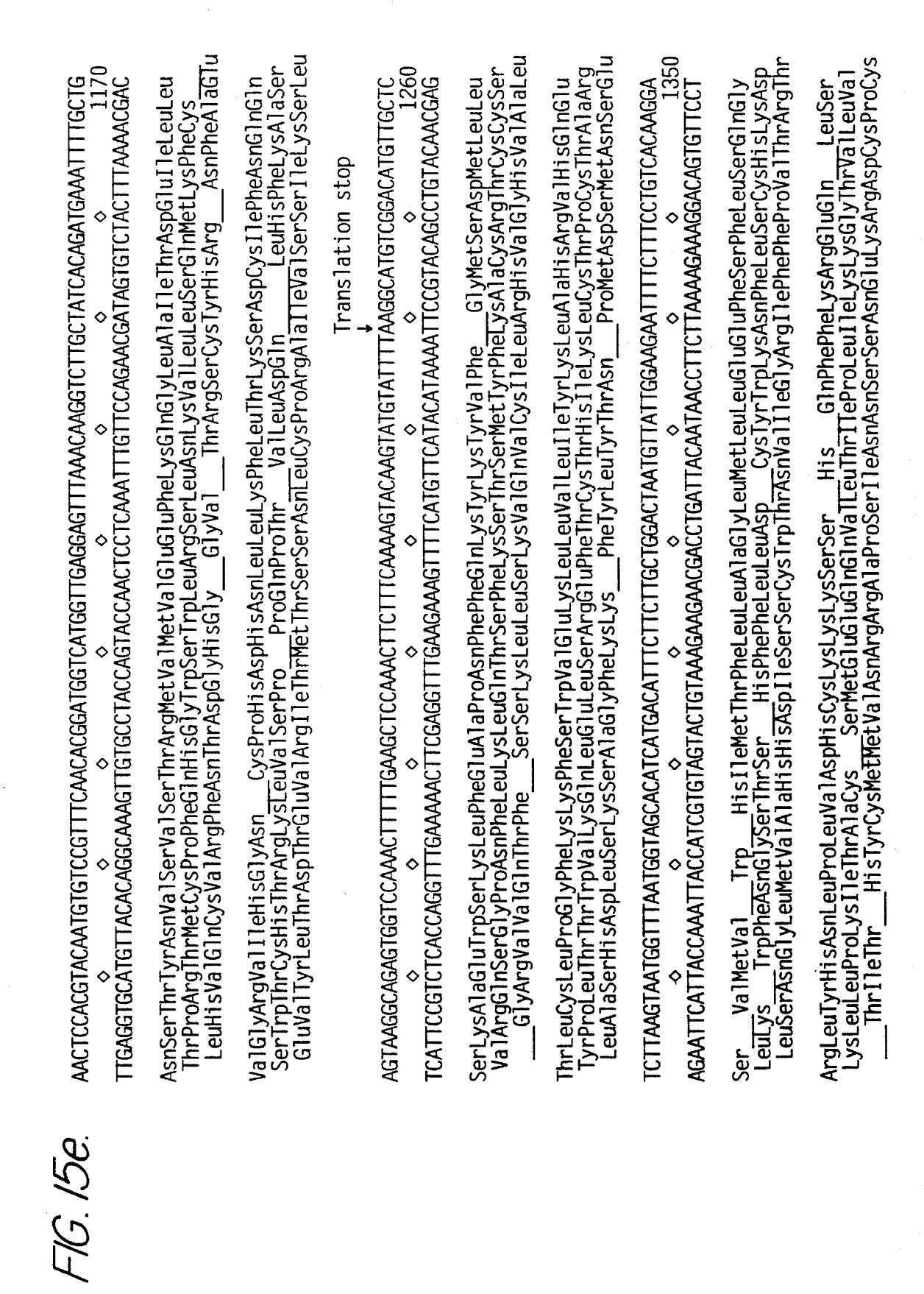

FIG. 15 is the nucleotide base sequence of part of the gene encoding human poly(A) polymerase, as well as the standard three letter code for amino acid sequence in all three reading frames. This nucleic acid causes expression of a 43 Kd protein in E. coli; and FIG. 16 is the nucleotide base sequence of the proposed coding region shown in FIG. 15, with amino acid sequence shown by one letter code.

Poly(A) polymerase

Poly(A) polymerases of this invention are generally described above. They are generally eukaryotic enzymes produced by recombinant DNA methodology, examples of which are provided below. These examples are not limiting in the invention and those of ordinary skill in the art will recognize that equivalent poly(A) polymerases can be isolated from other organisms using similar techniques. In addition, once the poly(A) polymerase from any organism has been isolated and the DNA sequence determined, that DNA sequence may be modified with little or no affect on the resulting amino acid sequence to produce equivalent nucleic acid. Such modifications in the DNA molecule are within the scope of this invention. In addition, those DNA modifications which cause production of an amino acid sequence in which conservative amino acid substitution is observed, and which have little or no affect on the resulting activity of the poly(A) polymerase activity (as defined below), are within the invention. Similarly, other amino acid substitutions which have little or no affect, are also within the invention. Thus, altered proteins having poly(A) polymerase activity, and DNA sequences encoding such altered amino acid sequences are within the scope of this invention.

EXAMPLE 1

Yeast Poly(a) polymerase

Purified native yeast poly(A) polymerase (PAP) was digested with trypsin and amino acid sequences were obtained from five HPLC-purified peptides. Referring to FIG. 4, the first 14 amino acids from one peptide were used for the design of two DNA oligonucleotides and a PAP-specific DNA fragment was amplified by PCR and two genomic clones isolated from a yeast plasmid library as described below. The sequence of the gene encoding yeast poly(A) polymerase is shown in FIG. 2.

Referring again to FIG. 4, the peptide sequence (top of figure) is given in single letter code. The sense orientation of possible corresponding DNA sequences is shown. The primers (completely degenerate) are indicated by arrows pointing 5' to 3'. Restriction sites and two dC's were present at the 5' end of each primer. The PCR reaction contained in a total volume of 50 µl: 10 mM Tris-HCl, pH 8.3, 50 mM KCl, 2.5 mM MgCl$_2$, 0.01 percent Triton X-100, 0.2 mM of each dNTP, 2.8 µM of each primer, 1 µg yeast chromosomal DNA and 2.5 units of AMPLITAQ (Perkin Elmer Cetus) that was added after the initial denaturation step. After denaturation at 96° C. for 5 min, the reaction was carried out for 30 cycles at 94° C. for 15 sec, 48° C. for 15 sec and 72° C. for 1 min. The fragment obtained was purified and labeled with $^{32}$P. A plasmid library (Nasmyth and Tatcheil, 19 Cell 753, 1980) containing yeast genomic fragments in YEp13 was screened by standard methods.

The coding region for PAP was located by Southern blotting with a 2286 bp XhoI-HindIII fragment (containing the whole PAP1 gene) common to two clones. This fragment contained an open reading frame encoding 568 amino acids, including all sequences obtained from the tryptic peptides (FIG. 3). Its predicted molecular weight of 64,551 is in good agreement with the estimate of 63,000 for purified native PAP.

Referring to FIGS. 6A and B, Southern blot hybridization of yeast genomic DNA cut with different enzymes showed that PAP1 is a single copy gene in the haploid genome.

The yeast chromosome contains the same HindIII fragment that is present in the isolated clone. A strain heterozygous for a deletion in the PAP1 gene was constructed: 84 percent of the PAP1 coding region was replaced by a LEU2 gene insertion on a plasmid (FIG. 6A, lower panel). A linearized fragment containing this LEU2 marker and the PAP1 flanking region was used to transform a diploid leucine auxotrophic yeast strain. Leu+ transformants were selected and analyzed by Southern blotting (FIG. 6A). All seven transformants analyzed contained one disrupted PAP1 allele and one wild type allele. The isolates were sporulated and tetrads were dissected. All viable spores were leucine auxotrophs and in no case did more than two of the four separated spores form colonies. The deletion could be rescued when PAP1 was supplied on a centromeric plasmid (data not shown). Thus, PAP1 is indispensable for cell growth.

A 2286 bp XhoI-HindIII fragment containing the entire gene was subcloned into pBluescript SK-(Stratagene) to give the plasmid pXPS. pXPSExo1.3, is a clone that contains in addition to the PAP1 coding region 239 bp of upstream sequence and 100 bp of nontranslated downstream sequence in the pBluescript vector SK-(Stratagene). It is a derivative of pXPS that was made by deleting some of the nontranslated 3'-region with Exonuclease III according to Henikoff (Gene 28, 351–359, 1984).

Expression of recombinant PAP

The gene (PAP1) was expressed in *E. coli* under the control of the phage T7 promoter in a plasmid, pJC10, shown in FIG. 13. pJPAP1 was constructed using the polymerase chain reaction and two oligonucleotides as primers. One primer (GGGGATCCATATGAGCTCTCAAAAG-GTTTTTG) was complementary to the translation initiation site of PAP1 and carried in addition an NdeI site (italic). The other primer was the commercial SK primer (Stratagene, La Jolla, Calif.). With these two oligonucleotides and 20 ng of linearized pXPSExo1.3 as template, the entire coding region was amplified. The PCR-product was gel purified, cut with NdeI and BamHI and subcloned into the respective restriction sites of the T7 transcription/translation vector pJC10 (Close et al., Cell 63, 1085, 1990). This construct allowed the expression of recombinant yeast poly(A) polymerase from the natural initiation codon.

Referring to FIG. 5, the specific activity of recombinant PAP in a crude extract of the recombinant *E. coli* strain was 120-fold higher than that of a control extract. Specifically, a T7 overexpression system was used for recombinant expression of yeast poly(A) polymerase in *E. coli*. Plasmid pJPAP1 was used to transform BL21(DE3) pLysS. As described above, pJPAP1 contains the coding region of PAP1 and 100 bp of untranslated trailer cloned into the T7 transcription/translation vector pJC10. Extracts were prepared from 2 l cultures. The extract was diluted to 50 ml to final concentrations of 100 mM KCl, 50 mM Tris-HCl pH 8.0, 0.5 mM DTT, 1 mM EDTA, 10 percent glycerol and loaded onto a 100 ml DEAE-Sepharose column equilibrated in the same buffer. The flowthrough which contained all of the activity was collected and the enzyme was purified further by chromatography on hydroxyapatite and Mono S essentially as described by Lingner et al. 266 J. Biol. Chem. 8741, 1991. Approximately 1.8 mg of purified protein was obtained with an overall recovery of 35 percent.

Upon purification (FIG. 5), a protein of the expected molecular weight comigrated with PAP activity through all steps. Chromatographic properties, electrophoretic mobility (FIG. 5B, compare lanes 5 and 10), and specific activity ($1.3 \times 10^6$ U/mg) of the recombinant enzyme were indistinguishable from authentic native PAP.

EXAMPLE 2

Bovine Poly(A) polymerase

Referring to FIG. 7, amino acid sequences were obtained from the N-terminus as well as from three tryptic peptides of purified native bovine poly(A) polymerase. DNA oligonucleotides to be used as primers for the polymerase chain reaction (PCR) were synthesized based on some of these amino acid sequences.

For N-terminal sequencing of purified poly(A) polymerase, about 30 µg of protein purified from calf thymus (as described by Wahle 266 J. Biol. Chem. 3131, 1991) were precipitated with 20% trichloroacetic acid, washed with ether, dissolved in 2% SDS and sequenced on an Applied Biosystems model 477A/120A sequencer according to the procedures of the manufacturer. For preparation of tryptic fragments, about 60 µg of purified protein were dialyzed against 10 mM Tris-HCl, pH 8.5, and concentrated to 50 µl in a SpeedVac. The protein was digested with trypsin and peptides were isolated on a PEP-S column (Pharmacia) as described by Schiltz et al., Eur. J. Biochem. 199:587, 1991. Four peptides were sequenced.

All PCR primers derived from amino acid sequences were fully degenerate. For some primers this required synthesis in two batches. If necessary the last nucleotide of the 3'-terminal codon was omitted so that ambiguities in the 3'-terminal nucleotide were avoided. All PCR primers carried nucleotide sequence including restriction sites at their 5'-terminal for ease of subcloning.

Total RNA was prepared from HeLa cells or calf thymus by the guanidinium isothiocyanate procedure (MacDonald et al., Methods Enzymol 152:219, 1987), poly(A)+ RNA was isolated from total RNA by a single run on oligo(dT)-cellulose (Sambrook et al., Molecular Cloning: A Laboratory Manual, Cold Spring Harbor Laboratory Press, Cold Spring Harbor, N.Y., 1989).

Reverse transcription of RNA was done with 75 U of reverse transcriptase 2 µg of calf thymus RNA and 1 µg of oligo(dT) or 0.2 µg of specific oligonucleotide primer in 50 µl of 50 mM Tris-HCl, pH 8.3, 100 mM KCl, 3 mM $MgCl_2$ 10 mM DTT and 0.2 mM of each dNTP. The mixture was heated for 5 min. at 80° C. before the addition of DTT and enzyme and subsequently incubated for 30 min. each at 37° C. and 43° C. The enzyme was inactivated by heating for 10 min. to 90° C.

For PCR, 5 µl of a reverse transcriptase reaction was used as template. The reactions were carried out in 30 µl of 10 mM Tris-HCl, pH 8.3. 50 mM KCl. 2.5 mM $MgCl_2$ 0.01% Triton X-100, 0.2 mM of each dNTP with 200–300 ng of each primer and 2.5 U of Taq polymerase. Typically, 30 cycles were carried out consisting of 0.5 min at 94° C m 1 min at 55°–59° C. and 2 min at 72° C. Products were analyzed on agarose gels and the desired products were purified by a GeneClean kit (obtained from Bio 101).

The templates used for PCR were obtained by reverse transcription of calf thymus RNA, primed either by oligo(dT) or by the same DNA oligonucleotide that was used as a PCR primer. A DNA fragment of 700 nucleotides was obtained, among others, in a PCR reaction using primers 1 and 4 (FIG. 7). After gel purification, this fragment could be reamplified with primers 2 and 4. Direct sequencing of the PCR product with primer 2 revealed a nucleotide sequence downstream of the primer that encoded six amino acids known from the sequencing of the purified protein (data not shown). Correct products, identified by similar procedures, were also obtained with other primer combinations (data not shown).

The 700 bp fragment obtained with primers 2 and 4 was used as a probe to screen two cDNA libraries, derived from HeLa cells and calf thymus respectively. The HeLa cDNA library in lambda gt11 was obtained from Peter Nielsen, Max Planck-Institute for Immunbiologie, Freiburg, FGR. An oligo(dT)-primed cDNA library from calf muzzle epithelium in lambda ZAPII (Stratagene) was obtained from Peter Koch and Werner W. Franke, Deutsches Krebsforschungszentrum, Heidelberg, FRG (Koch et al., Eur. J Cell Biol. 53:1, 1990). Libraries were screened according to standard procedures (Sambrook et al., supra).

Clones were only obtained from the HeLa library. Although these clones encoded the correct amino acid sequences, they had an open reading frame for a protein of only 43 kDa and lacked peptide 66 (see below). Therefore, a fragment from the coding region of these clones was used to screen an additional cDNA library from calf muzzle epithelium. The calf muzzle library was screened with a Psi-Kpni fragment derived from the short HeLa cDNA clone, labelled by random priming. This fragment corresponded to nucleotides 572–975 of the clone represented in FIG. 1. Subcloning from lambda ZAP was done in vivo according to the procedure suggested by Stratagene. Primers were synthesized to match internal sequences of the insert or standard primers were used in combination with deletions generated by exonuclease III according to a protocol supplied by Stratagene.

The largest cDNA clone obtained in this screen was 2.5 kb in length (FIG. 1). It contained an open reading frame coding for a protein of 739 amino acids with a molecular weight of 82.4 kDa. The N-terminus of the predicted amino acid sequence was identical with the N-terminus sequence obtained from purified poly(A) polymerase except for the absence of the initiating methionine in the protein. The predicted sequence also contained all internal peptide sequences derived from the purified protein.

Expression of bovine poly(A) polymerase in E. coli

A fragment containing the open reading frame of the bovine clone was inserted into a T7 expression vector such that the initiating ATG codon was that encoding the first amino acid of the authentic protein.

The coding sequence of the bovine poly(A) polymerase clone was inserted into two related expression vectors, pJC10 (Closet al., supra) and pT7-7 (constructed by Dr. Stanley Tabor, Harvard University, Cambridge, Mass.). Both vectors contain a promoter recognized by the bacteriophage T7 RNA polymerase. The host strain, BL21, carried the phage DE3 with the T7 RNA polymerase gene under the control of the lacZ promoter as well the pLysS plasmid (Studier, 219 J. Mol. Biol. 37, 1991).

The poly(A) polymerase coding sequence was PCR-amplified. The upstream primer covered the ATG initiation codon, converting it into an NdeI site, the other was the Bluescript SK sequencing primer. The amplification was carried out with 1 µg of plasmid DNA and 8 PCR cycles and the amplified fragment was cloned into the NdeI and BamHI sites of the two vectors. For each of the two vectors, two identical constructs were made with inserts from two independent PCR reactions. One representative of each of the four constructions and a control with the empty pJC10 vector were induced with IPTG, and lysates were tested for nonspecific poly(A) polymerase activity. All four constructs had 1.5 to 2-fold elevated levels of poly(A) polymerase activity.

Specifically, depending on the induction conditions, the synthesis of a polypeptide of the expected size could be barely or not at all detected by SDS-PAGE of total cell lysates. After induction overnight at 18° C., nonspecific poly(A) polymerase activity, measured by the incorporation of radiolabeled ATP into acid-precipitable material in the presence of a poly(A) primer and $Mn^{2+}$, was only 2-fold higher than in a control lysate, 12,800 versus 6,700 U/mg.

The most promising strain, pT7-PAP82, was induced at a larger scale together with the empty pJC10 vector as a control. Single colonies of each strain were inoculated into L8 medium with 100 µg/ml ampicillin and grown overnight at 37° C. These cultures were diluted 1:80 into 2 l of the same medium and grown at 37° C. to an $A_{600}$ of 0.15. They were further incubated at 18° C. and, at an $A_{600}$ of 0.5–0.6 IPTG was added to a final concentration of 1 mM to induce the synthesis of T7 RNA polymerase, 18 h after induction the cells were harvested by centrifugation and each strain was resuspended in 50 ml of 100 mM KCl, 50 mM Tris, pH 7.9, 5 mM EDTA. The suspensions were frozen in liquid nitrogen, thawed, and following additions were made: 10% glycerol, 0.5 mM DTT, 0.5 mM phenylmethylsulfluoride, 0.4 µg/ml leupeptin, 0.7 µg/ml pepstatin. The cells were sonicated until the viscosity was reduced to that of buffer and the lysate was centrifuged for 30 min at 48,000 g and 0° C.

Nonspecific poly(A) polymerase activity was measured in the presence of $Mn^{2+}$ as the primer-dependent incorporation of radiolabeled ATP into acid-precipitable material under the conditions described by Wahle, supra). The primer used was poly(A). Poly(A) polymerase units were as defined by Wahle, supra. Specific polyadenylation assays were carried out by complementation of poly(A) polymerase fractions with purified CPF as described by Wahle, Cell 66:759, 1991. AAUAAA-containing RNA substrates and their mutant derivatives were either chemically synthesized 18mers or transcripts of SP6 RNA, polymerase.

The supernatant of pT7-PAP82 contained 754 mg of protein and $9.7 \times 10^6$ U of poly(A) polymerase, whereas the lysate of pIC10 contained 708 mg of protein and $4.7 \times 10^6$ U of poly(A) polymerase. Both lysates were applied to DEAE-Sepharose FF columns (150 ml) equilibrated in the same buffer as above, including all additions, except that EDTA was reduced to 1 mM. The columns were washed with 100 ml of equilibration buffer and elouted with the same buffer containing 0.6M KCl. Fractions of 30 ml were collected. The combined flowthrough fractions of pT7-PAP82 contained 329 mg of protein and $5.2 \times 10^6$ U of poly(A) polymerase, the eluate contained 506 mg and 506 mg and $5.2 \times 10^6$ U. The flowthrough of pJC10 contained 252 mg and $0.6 \times 10^6$ U, the eluate contained 569 mg and $3.7 \times 10^6$ U.

Polyadenylation of RNA substrates dependent on the addition of the specificity factor CPF and the presence of the hexanucleotide sequence AAUAAA in the RNA distinguished the activity derived from the cDNA from a high background of endogenous activity. Whether the background is due to E. coli's own poly(A) polymerase or some other enzyme that incorporates ATP in the crude extract is not known. The background activity could be readily removed by DEAE chromatography.

Specifically, referring to FIG. 8, DEAE chromatography of the lysate divided this activity in two equal portions, one in the flowthrough and one in the eluate. The activity in the control lysate, in contrast, bound almost completely to the DEAE column under the same conditions. The presence of mammalian poly(A) polymerase in the E. coli lysate was clearly detected by the specific polyadenylation assay: upon complementation with purified specificity factor CPF, the lysate from the strain harboring the cloned gene, as well as the DEAE flowthrough fraction derived from this lysate, polyadenylated a radiolabeled precursor RNA containing the AAUAAA sequence (FIG. 8, lanes 4 and 5). In contrast, the control lysate was inactive in this assay, as were both DEAE fractions derived from it as well as the DEAE-bound fraction derived from the overproducing strain (FIG. 4, lanes 6–10). The polyadenylation activity present in the DEAE flowthrough of the overproducing strain was partially purified as described above. Activities measured by the specific and nonspecific polyadenylation assays as described above copurified and in the final MonoQ column a protein of the anticipated molecular weight was correlated with both activities (FIGS. 9, 10, and 11). At all stages tested, polyadenylation activity in the specific assay was dependent on the presence of both CPF and an intact AAUAAA sequence in the RNA (FIG. 11 and data not shown). These results thus confirm that the cDNA described above encodes functional poly(A) polymerase.

The DEAE flowthrough derived from pT7-PAP82 was applied to a 150 ml hydroxyapatite column in the same buffer as above except that EDTA was omitted. The column was washed with one volume of equilibration buffer and eluted with a 10 volume gradient from equilibration buffer to 0.3M potassium phosphate, pH 7.2, 10% glycerol, 0.5 mM DTT, 0.4 µg/ml leupeptin, 0.7 µg/ml pepstatin. The combined peak fractions, eluted at 100 mM phosphate, contained 30 mg of protein and $2.2 \times 10^6$ U of poly(A) polymerase.

Two attempts to absorb this material to a MonoS column under the conditions described by Wahle, supra, failed. A portion of the preparation ($0.8 \times 10^6$ U) was therefore dialyzed overnight against 25 mM Tris-HCl, pH 7.9, 10% glycerol, 1 mM EDTA, 0.5 mM DTT, 0.05% Nonidet P40 and applied to a 1 ml MonoQ FPLC column. After washing loading buffer, the column was eluted with a 40 ml gradient from 0 to 50 mM KCl in loading buffer. Fractions of 0.5 ml were collected. Binding of poly(A) polymerase was very weak again: 70% of the poly(A) polymerase activity applied was recovered in the flowthrough and 15% was eluted as a single peak at 15 mM KCl.

Northern blot analysis of HeLa and calf thymus poly(A) RNA under stringent conditions with a probe derived from the N-terminus half of the poly(A) polymerase coding revealed two strong bands of ~4.5 kb and 1.3 kb and a weak band of 2.4 kb (FIG. 12, lane 1).

For Northern analyses, RNA was separated in 1% agarose-formaldehyde gels and transferred to nitrocellulose by capillary blotting according to Sambrook et al., supra, except that the filters were not washed before baking. Markers were run in neighboring lanes and visualized by ethidium bromide staining. Blots were prehybridized for 2–3 h at 68° C. in 6×SSC, 5×Denhardt's solution, 0.5% SDS and 0.1 mg/ml herring sperm DNA. Hybridization was carried out overnight under the same conditions with double-stranded DNA probes, labeled by random priming (Sambrook et al., supra) and denatured by boiling, at $\sim 5 \times 10^6$ c.p.m./ml (Cerenkov counting). Blots were washed twice in 2×SSC, 0.5% SDS at room temperature (20–40 min. with agitation), once in 0.1×SSC, 0.5% SDS at room temperature, then under the same conditions at 68° C. and again at room temperature.

Specifically, referring to FIG. 12, the largest RNA appeared as a double band. A probe derived from the C-terminal half of the same clone reacted only with this large RNA (FIG. 12, lane 2). This suggests that the cDNA clone was derived from the 4.5 kb mRNA and thus lacks a substantial amount of untranslated sequence, and that the two other mRNAs are related to the 5'-half of the 4.5 kb species. As mentioned above, several independent human cDNA clones encoding a protein of 43 kDa were isolated. The first 371 of its 375 amino acids differed from the corresponding part of the long bovine clone by a single amino acid replacement. The sequence deviated from that of the bovine clone in the last four amino acids and the long 3'-untranslated region. The 5'-untranslated regions were also dissimilar with the exception of about 30 nucleotides immediately preceding the coding regions (data not shown).

Two arguments suggest that the major differences between the clones were not related to their difference in origin, bovine versus human. First, sequences very similar to those unique for the short human clone could be amplified from bovine cDNA by PCR using appropriate primers. Second, the length of the clones encoding the 43 kDa protein (2.1 kb, including 49 nucleotides of poly(A)) is quite similar to the length of the intermediate mRNA visible in the Northern blot of FIG. 12. The probe that detected this band consisted of sequence common to both classes of cDNA clones and the band was present in both human and bovine mRNA. The same band of mRNA was not detected by the probe unique for the long cDNA clone (see above). These data thus suggest that the short cDNA clone represents the 2.4 kb mRNA encoding a protein of 43 kDa that is identical or nearly identical to the first half of poly(A) polymerase. So far, no cDNA clones have been obtained that might represent the smallest class of mRNA visible in the Northern blot.

The open reading frame in the cDNA clone appears to be complete; it starts with an ATG codon, followed by amino acid sequence present at the N-terminus of the purified enzyme, and is preceded and followed by sequences containing multiple stop codons in all three frames. The predicted protein has a size of 82 kDa and a polypeptide of this size copurified with poly(A) polymerase activity after expression in *E. coli*. Expression and purification of the protein can be improved by standard procedures, e.g., provision of a stronger promoter or removal of inhibitory 5' or 3' sequence. The *E. coli*-made protein is substantially larger than the one purified from calf thymus, suggesting that the latter suffers proteolysis upon purification. Proteolysis is likely to be at least a partial explanation for the heterogeneity of poly(A) polymerase during purification that has been observed by numerous investigators. These data also suggest that a C-terminal domain of 20 kDa is dispensable for specific and nonspecific polyadenylation.

The two probes used in Northern blot analysis detected a mRNA of ~4.5 kb in HeLa and bovine mRNA. This suggests that long untranslated sequences are missing from the clone. The N-terminal probe also detected two additional mRNAs of 2.4 and 1.3 kb. The 2.4 kb message is probably represented by several human cDNA clones encoding a protein of 43 kDa that is almost identical to the N-terminal half of the protein predicted from the long bovine clone. The minute difference between the two proteins may be due to their different origins and the two mRNAs might be the product of alternative splicing.

EXAMPLE 3

Human Poly(A) polymerase

As discussed above human poly(A) polymerase-encoding DNA has been isolated. The nucleotide base sequence of one clone is shown in FIGS. 15 and 16, and a suitable expression vector, shown in FIG. 14, constructed in a manner equivalent to that discussed above. This vector causes production of a 43 Kd protein in *E. coli*, as discussed above (see Example 2 and FIG. 14).

Methods

In the presence of ATP, the above poly(A) polymerases add tracts of adenosine residues to the 3' end of RNA. Any RNA can be used as substrate (Lingnet et al., J. Biol. Chem. 266, 8741, 1991). In particular, ribozymes may be poly(A)-tailed to improve their stability in vivo.

EXAMPLE 4

Poly(A)-Tailing of Ribozymes 2.5 µm ribozyme (a 36mer, about 65,000 cpm/µl) in 250 mM NaCl, 10 mM MgCl$_2$, 2.5 mM MnCl$_2$, 50 mM Tris (pH 8), 4 mM ATP (1600× excess over Ribozyme), and 0.09 U/µl *E. coli* Poly(A) Polymerase (U.S. Biochemical Corporation, Cleveland, Ohio) in a total volume of 30 µl was incubated at 37° C. for 1 hour. Untailed ribozyme was removed by loading the sample on an 8 ml G-100 column and eluting in 75 mM Tris (pH 7.5), 0.1 mM EDTA, 100 mM NaCl (the NaCl is not required), collecting 0.5 ml fractions, and counting in a scintillation counter to collect tailed fractions (hot). These fractions were run on a 5% acrylamide, 8M urea gel and the length of tails quantitated. Fraction 6 showed 250–325 poly(A) tails and <5% (probably about 2%) untailed ribozyme.

In similar experiments the length of tails were as follows:

| Time | Tail length |
| --- | --- |
| 1 hr | 250–325 |
| 2 hr | 300–375 |
| 3 hr | 350–390 |
| 4 hr | 380–440 |

Poly(A) polymerase of this invention can label the 3' end of RNA useful for chemical and enzymatic sequencing of RNA, footprinting, etc., with a single hot adenosine residue, e.g., with [$^{32}$P]-cordycepintriphosphate. (Eucaryotic mRNAs are resistant to 5' labeling because of their cap structure.) 3' end labeling is currently done with RNA ligase and [$^{32}$P]pCp (England and Uhlenbeck, 275 Nature 560, 1978). This reaction requires long incubation times. Poly(A) polymerase can perform this reaction very efficiently, and within minutes. Also, recombinant yeast poly(A) polymerase purified from *E. coli* has no RNAse contamination detectable under conditions used for end-labelling.

cDNA synthesis from nonpolyadenylated RNAs as, for example, bacterial mRNA, viral RNA, or histone mRNA can be performed by polyadenylation of these RNAs prior to hybridization to oligo dT and reverse transcription.

Polyadenylated mRNA is translated more efficiently in reticulocyte lysate (Munroe and Jacobson, Gene 91:151–158, 1990). Long tracts of poly(A) can be added to selected or non-selected mRNA with poly(A) polymerase and cold ATP to improve such translation.

Labeled poly(A) can be easily synthesized with poly(A) polymerase, and is useful as a substrate for different enzymes, such as Ribonuclease H (Keller and Crouch, Proc. Natl. Acad. Sci. 69:3360–3364, 1972) or Poly(A)nuclease.

Polyadenylated RNA can be bound to oligo dT cellulose. It is possible to polyadenylate short RNAs that have a specific sequence with poly(A) polymerase. This makes it possible to affinity purify such RNAs.

PCR permits the generation of cDNA libraries from very small quantities of RNA. A major problem in the construction of representative libraries is the preferential amplification of small pieces of DNA and thus the loss of long cDNAs. A possible solution to this problem is a controlled alkaline hydrolysis of the initial RNA sample, followed by phosphatase treatment, poly(A) tailing with recombinant poly(A) polymerase and oligo(dT)-primed cDNA synthesis. In this way, a uniform length of cDNAs would be achieved.

In addition, the recombinant poly(A) polymerase may be used in place of purified native poly(A) polymerase, e.g., (a) in an assay for poly(A) tails where poly(A) polymerase in the presence of cordycepin triphosphate is used to add 1 or 2 radiolabelled ATP's to the 3' end of RNA molecules; these molecules are then bound to oligo(dT) and cleaved with RNAse H. TCA precipitable counts are porportional to poly(A) RNA in the sample; (b) it may also be used as described by Beltz and Ashton, Fed. Proc. 41:1450 Abstract 6896 (1982) for labelling the 3' end of large (e.g., 1000mers) RNA for sequencing; and (c) used for cloning viral RNA as described by Gething et al., Nature 287:301, 1980.

Recombinant poly(A) polymerase is more highly purified and has little contamination, including no contamination with RNAse. It also has higher specific activity. For all these reasons, better results are attained compared to prior methods.

Any RNA can be polyadenylated with ATP or blocked at the 3' end with 3' dATP and poly(A) polymerase. With such substrates different important biochemical and cell biological questions could be addressed. See, e.g., Wickens, 15 TIBS 320, 1990).

EXAMPLE 5

Reaction conditions for yeast poly(A) polymerase

All reactions that are done with yeast poly(A) polymerase contain 20 mM Tris-Cl pH 7.0, 60 mM KCl, 0.7 Mm MnCl$_2$, 0.2 mM EDTA, 0.5 mM dithiotreitol, 10% glycerol, 0.8% bovine serum albumine, RNA, poly(A) polymerase, and ATP (or dATP or cordycepine-5'triphosphate). The reaction is carried out at 30° C. The concentration of RNA, enzyme, and ATP (dATP, cordycepine) can be varied according to the aim of the particular experiment. Short or long poly(A) tails can be added to any RNA by varying incubation time and/or enzyme concentration and/or ATP concentration and/or RNA concentration.

Other embodiments are within the following claims.

We claim:

1. Purified nucleic acid encoding a yeast poly(A) polymerase having an amino acid sequence shown as Seq. I.D. No. 3, said nucleic acid comprising the nucleotide base sequences, encoding said amino acid sequences, shown as Seq. I.D. No. 2.

2. The purified nucleic acid of claim 1 said nucleic acid encoding enzymatically active said poly(A) polymerase.

3. A vector comprising the purified nucleic acid of claim 1.

4. The vector of claim 3, further comprising a promoter sequence located adjacent said purified nucleic acid and adapted to control expression of said nucleic acid, wherein expression of said nucleic acid from said promoter causes production of enzymatically active poly(A) polymerase.

5. A method for production of the purified poly(A) polymerase of claim 1, comprising the steps of:

providing said purified nucleic acid encoding yeast poly(A) polymerase, said nucleic acid having a promoter sequence upstream of the nucleic acid encoding said poly(A) polymerase, said nucleic acid being present in the genome of a living cell, or within an autonomous vector in said living cell, and causing expression of said poly(A) polymerase within said cell from said promoter.

6. The method of claim 5, wherein said poly(A) polymerase is expressed in *Eschericia coli*.

7. The method of claim 5, wherein said poly(A) polymerase is a vector selected from plasmid, cosmid, phage, and phasmid.

8. The method of claim 5, wherein said nucleic acid lacks a 5'-untranslated sequence naturally associated with nucleic acid encoding said poly(A) polymerase.

9. The method of claim 6, further comprising the step of purifying the poly(A) polymerase expressed from said nucleic acid by passing said poly(A) polymerase over diethylamimoethyl column, or its equivalent, to separate non-eucaryotic poly(A) polymerase from said yeast poly (A) polymerase.

10. The method of claim 9, wherein said yeast poly(A) polymerase is further purified by passage over a hydroxyapatite column.

11. The method of claim 9, wherein said yeast poly(A) polymerase is further purified by passage over a cationic exchange resin column having beads of hydrophilic resin having a particle size of 10 μM and charged groups of —$CH_2$—$SO_3$—.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2482 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 46..2262

( x i ) SEQUENCE DESCRIPTION: SEQ ID NO:1:

```
GCGGTTGCGG GGGGGAAGTG ACTGGGCGGT GCGGCGCAGG AGACG ATG CCG TTT          54
                                                  Met Pro Phe
                                                   1

CCA  GTT  ACA  ACA  CAG  GGA  TCA  CAG  CAA  ACA  CAG  CCG  CCA  CAG  AAG  CAC   102
Pro  Val  Thr  Thr  Gln  Gly  Ser  Gln  Gln  Thr  Gln  Pro  Pro  Gln  Lys  His
      5              10                       15

TAT  GGC  ATT  ACT  TCT  CCC  ATC  AGC  TTA  GCA  GCC  CCC  AAG  GAG  ACT  GAC   150
Tyr  Gly  Ile  Thr  Ser  Pro  Ile  Ser  Leu  Ala  Ala  Pro  Lys  Glu  Thr  Asp
 20                   25                   30                             35

TGC  CTG  CTC  ACA  CAG  AAG  CTG  GTG  GAG  ACT  CTG  AAG  CCC  TTC  GGG  GTT   198
Cys  Leu  Leu  Thr  Gln  Lys  Leu  Val  Glu  Thr  Leu  Lys  Pro  Phe  Gly  Val
               40                        45                        50

TTT  GAA  GAG  GAA  GAG  GAA  CTG  CAG  CGC  AGG  ATT  TTT  ATT  TTG  GGA  AAA   246
Phe  Glu  Glu  Glu  Glu  Glu  Leu  Gln  Arg  Arg  Ile  Phe  Ile  Leu  Gly  Lys
          55                        60                        65

TTA  AAT  AAC  CTG  GTA  AAA  GAG  TGG  ATA  CGA  GAA  ATC  AGT  GAA  AGC  AAG   294
Leu  Asn  Asn  Leu  Val  Lys  Glu  Trp  Ile  Arg  Glu  Ile  Ser  Glu  Ser  Lys
          70                        75                        80

AAT  CTT  CCA  CAA  TCT  GTA  ATT  GAA  AAT  GTT  GGT  GGG  AAA  ATT  TTT  ACA   342
Asn  Leu  Pro  Gln  Ser  Val  Ile  Glu  Asn  Val  Gly  Gly  Lys  Ile  Phe  Thr
     85                        90                        95

TTT  GGA  TCT  TAT  AGA  TTA  GGA  GTA  CAT  ACA  AAA  GGT  GCT  GAT  ATT  GAT   390
Phe  Gly  Ser  Tyr  Arg  Leu  Gly  Val  His  Thr  Lys  Gly  Ala  Asp  Ile  Asp
100                 105                      110                      115

GCA  TTG  TGT  GTT  GCA  CCA  AGA  CAT  GTT  GAT  CGA  AGT  GAT  TTT  TTC  ACC   438
Ala  Leu  Cys  Val  Ala  Pro  Arg  His  Val  Asp  Arg  Ser  Asp  Phe  Phe  Thr
                    120                      125                      130

TCA  TTC  TAT  GAT  AAG  TTG  AAA  TTA  CAG  GAA  GAA  GTA  AAA  GAT  TTA  AGA   486
Ser  Phe  Tyr  Asp  Lys  Leu  Lys  Leu  Gln  Glu  Glu  Val  Lys  Asp  Leu  Arg
               135                      140                      145

GCT  GTT  GAA  GAG  GCA  TTT  GTA  CCA  GTT  ATC  AAA  CTG  TGT  TTT  GAT  GGG   534
Ala  Val  Glu  Glu  Ala  Phe  Val  Pro  Val  Ile  Lys  Leu  Cys  Phe  Asp  Gly
          150                      155                      160

ATA  GAG  ATT  GAT  ATT  TTG  TTT  GCA  AGA  TTA  GCA  CTG  CAG  ACT  ATT  CCA   582
Ile  Glu  Ile  Asp  Ile  Leu  Phe  Ala  Arg  Leu  Ala  Leu  Gln  Thr  Ile  Pro
     165                      170                      175

GAA  GAC  TTG  GAC  TTA  AGA  GAT  GAC  AGT  CTG  CTT  AAA  AAT  TTA  GAT  ATA   630
Glu  Asp  Leu  Asp  Leu  Arg  Asp  Asp  Ser  Leu  Leu  Lys  Asn  Leu  Asp  Ile
180                 185                      190                      195

AGA  TGT  ATA  AGA  AGT  CTT  AAC  GGT  TGC  AGG  GTA  ACC  GAT  GAA  ATT  TTA   678
Arg  Cys  Ile  Arg  Ser  Leu  Asn  Gly  Cys  Arg  Val  Thr  Asp  Glu  Ile  Leu
                    200                      205                      210

CAT  CTA  GTA  CCA  AAC  ATT  GAC  AAC  TTC  AGG  TTA  ACC  CTG  AGA  GCT  ATC   726
His  Leu  Val  Pro  Asn  Ile  Asp  Asn  Phe  Arg  Leu  Thr  Leu  Arg  Ala  Ile
               215                      220                      225

AAA  CTG  TGG  GCC  AAA  CGC  CAC  AAC  ATC  TAT  TCC  AAT  ATA  TTA  GGT  TTC   774
Lys  Leu  Trp  Ala  Lys  Arg  His  Asn  Ile  Tyr  Ser  Asn  Ile  Leu  Gly  Phe
          230                      235                      240
```

| | | | | | | | | | | | | | | | | |
|---|---|---|---|---|---|---|---|---|---|---|---|---|---|---|---|---|
| CTC | GGT | GGT | GTT | TCC | TGG | GCT | ATG | CTA | GTA | GCA | AGA | ACT | TGC | CAG | CTT | 822 |
| Leu | Gly | Gly | Val | Ser | Trp | Ala | Met | Leu | Val | Ala | Arg | Thr | Cys | Gln | Leu | |
| | 245 | | | | 250 | | | | | 255 | | | | | | |
| TAT | CCA | AAT | GCA | ATA | GCA | TCA | ACT | CTT | GTA | CAT | AAA | TTT | TTC | TTG | GTA | 870 |
| Tyr | Pro | Asn | Ala | Ile | Ala | Ser | Thr | Leu | Val | His | Lys | Phe | Phe | Leu | Val | |
| 260 | | | | | 265 | | | | | 270 | | | | | 275 | |
| TTT | TCT | AAA | TGG | GAA | TGG | CCA | AAT | CCA | GTC | CTA | TTG | AAA | CAG | CCT | GAA | 918 |
| Phe | Ser | Lys | Trp | Glu | Trp | Pro | Asn | Pro | Val | Leu | Leu | Lys | Gln | Pro | Glu | |
| | | | | 280 | | | | | 285 | | | | | 290 | | |
| GAA | TGC | AAT | CTT | AAT | TTG | CCT | GTA | TGG | GAC | CCA | AGG | GTA | AAC | CCC | AGT | 966 |
| Glu | Cys | Asn | Leu | Asn | Leu | Pro | Val | Trp | Asp | Pro | Arg | Val | Asn | Pro | Ser | |
| | | | | 295 | | | | | 300 | | | | | 305 | | |
| GAT | AGG | TAC | CAT | CTT | ATG | CCT | ATA | ATT | ACA | CCA | GCA | TAC | CCA | CAA | CAG | 1014 |
| Asp | Arg | Tyr | His | Leu | Met | Pro | Ile | Ile | Thr | Pro | Ala | Tyr | Pro | Gln | Gln | |
| | | 310 | | | | | 315 | | | | | 320 | | | | |
| AAC | TCC | ACG | TAC | AAT | GTG | TCC | GTT | TCA | ACA | CGG | ATG | GTC | ATG | GTT | GAG | 1062 |
| Asn | Ser | Thr | Tyr | Asn | Val | Ser | Val | Ser | Thr | Arg | Met | Val | Met | Val | Glu | |
| | 325 | | | | | 330 | | | | | 335 | | | | | |
| GAG | TTT | AAA | CAA | GGT | CTT | GCT | ATC | ACA | GAT | GAA | ATT | TTG | CTG | AGT | AAG | 1110 |
| Glu | Phe | Lys | Gln | Gly | Leu | Ala | Ile | Thr | Asp | Glu | Ile | Leu | Leu | Ser | Lys | |
| 340 | | | | | 345 | | | | | 350 | | | | | 355 | |
| GCA | GAG | TGG | TCC | AAA | CTT | TTT | GAA | GCT | CCA | AAC | TTC | TTT | CAA | AAG | TAC | 1158 |
| Ala | Glu | Trp | Ser | Lys | Leu | Phe | Glu | Ala | Pro | Asn | Phe | Phe | Gln | Lys | Tyr | |
| | | | | 360 | | | | | 365 | | | | | 370 | | |
| CAG | CAT | GAT | ATT | GTA | CTT | CTA | GCA | AGT | GCA | CCA | ACT | GAA | AAA | CAA | CGC | 1206 |
| Gln | His | Asp | Ile | Val | Leu | Leu | Ala | Ser | Ala | Pro | Thr | Glu | Lys | Gln | Arg | |
| | | | 375 | | | | | 380 | | | | | 385 | | | |
| CTA | GAA | TGG | GTG | GGC | TTG | GTG | GAA | TCA | AAA | ATC | CGA | ATC | CTG | GTT | GGA | 1254 |
| Leu | Glu | Trp | Val | Gly | Leu | Val | Glu | Ser | Lys | Ile | Arg | Ile | Leu | Val | Gly | |
| | | 390 | | | | | 395 | | | | | 400 | | | | |
| AGT | TTG | GAG | AAG | AAT | GAG | TTT | ATG | ACA | CTG | GCT | CAT | GTG | AAT | CCC | CAG | 1302 |
| Ser | Leu | Glu | Lys | Asn | Glu | Phe | Met | Thr | Leu | Ala | His | Val | Asn | Pro | Gln | |
| | 405 | | | | | 410 | | | | | 415 | | | | | |
| TCA | TTT | CCA | GCA | CCC | AAA | GAA | AAT | CCC | GAC | AAG | GAA | GAA | TTT | CGC | ACT | 1350 |
| Ser | Phe | Pro | Ala | Pro | Lys | Glu | Asn | Pro | Asp | Lys | Glu | Glu | Phe | Arg | Thr | |
| 420 | | | | | 425 | | | | | 430 | | | | | 435 | |
| ATG | TGG | GTG | ATT | GGG | TTA | GTG | TTT | AAC | AAA | ACA | GAA | AAC | TCT | GAA | AAT | 1398 |
| Met | Trp | Val | Ile | Gly | Leu | Val | Phe | Asn | Lys | Thr | Glu | Asn | Ser | Glu | Asn | |
| | | | | 440 | | | | | 445 | | | | | 450 | | |
| CTC | AGT | GTT | GAT | CTC | ACC | TAT | GAT | ATT | CAG | TCT | TTC | ACA | GAT | ACA | GTT | 1446 |
| Leu | Ser | Val | Asp | Leu | Thr | Tyr | Asp | Ile | Gln | Ser | Phe | Thr | Asp | Thr | Val | |
| | | | 455 | | | | | 460 | | | | | 465 | | | |
| TAT | AGG | CAA | GCA | ATA | AAC | AGC | AAG | ATG | TTT | GAG | GTG | GAC | ATG | AAA | ATT | 1494 |
| Tyr | Arg | Gln | Ala | Ile | Asn | Ser | Lys | Met | Phe | Glu | Val | Asp | Met | Lys | Ile | |
| | | 470 | | | | | 475 | | | | | 480 | | | | |
| GCT | GCG | ATG | CAT | GTA | AAA | AGA | AAG | CAA | CTC | CAT | CAA | CTA | CTG | CCT | AGT | 1542 |
| Ala | Ala | Met | His | Val | Lys | Arg | Lys | Gln | Leu | His | Gln | Leu | Leu | Pro | Ser | |
| | 485 | | | | | 490 | | | | | 495 | | | | | |
| CAT | GTG | CTT | CAG | AAA | AAG | AAA | AAG | CAT | TCA | ACA | GAA | GGC | GTC | AAG | TTG | 1590 |
| His | Val | Leu | Gln | Lys | Lys | Lys | Lys | His | Ser | Thr | Glu | Gly | Val | Lys | Leu | |
| 500 | | | | | 505 | | | | | 510 | | | | | 515 | |
| ACA | CCT | CTG | AAT | GAT | AGC | AGC | CTC | GAC | TTG | TCT | ATG | GAC | AGT | GAC | AAC | 1638 |
| Thr | Pro | Leu | Asn | Asp | Ser | Ser | Leu | Asp | Leu | Ser | Met | Asp | Ser | Asp | Asn | |
| | | | | 520 | | | | | 525 | | | | | 530 | | |
| AGC | ATG | TCT | GTG | CCT | TCA | CCT | ACT | AGT | GCT | ATG | AAG | ACC | AGT | CCG | TTG | 1686 |
| Ser | Met | Ser | Val | Pro | Ser | Pro | Thr | Ser | Ala | Met | Lys | Thr | Ser | Pro | Leu | |
| | | | 535 | | | | | 540 | | | | | 545 | | | |
| AAC | AGT | TCT | GGC | AGC | TCT | CAG | GGC | AGA | AAC | AGT | CCT | GCT | CCA | GCT | GTA | 1734 |
| Asn | Ser | Ser | Gly | Ser | Ser | Gln | Gly | Arg | Asn | Ser | Pro | Ala | Pro | Ala | Val | |
| | | 550 | | | | | 555 | | | | | 560 | | | | |

| | | | | | | | | | | | | | | | | |
|---|---|---|---|---|---|---|---|---|---|---|---|---|---|---|---|---|
| ACA | GCA | GCA | TCT | GTG | ACC | AAC | ATA | CAG | GCT | ACT | GAA | GTT | TCT | CTG | CCA | 1782 |
| Thr | Ala | Ala | Ser | Val | Thr | Asn | Ile | Gln | Ala | Thr | Glu | Val | Ser | Leu | Pro | |
| | 565 | | | | 570 | | | | | 575 | | | | | | |
| CAA | ATA | AAT | TCC | AGT | GAA | AGC | TCA | GGG | GGT | ACA | TCG | AGT | GAA | AGC | ATT | 1830 |
| Gln | Ile | Asn | Ser | Ser | Glu | Ser | Ser | Gly | Gly | Thr | Ser | Ser | Glu | Ser | Ile | |
| 580 | | | | | 585 | | | | | 590 | | | | | 595 | |
| CCT | CAA | ACT | GCC | ACA | CAA | CCA | GCC | ATT | TCA | TCA | CCG | CCA | AAG | CCT | ACG | 1878 |
| Pro | Gln | Thr | Ala | Thr | Gln | Pro | Ala | Ile | Ser | Ser | Pro | Pro | Lys | Pro | Thr | |
| | | | | 600 | | | | | 605 | | | | | 610 | | |
| GTC | TCC | AGA | GTT | GTT | TCC | TCA | ACA | CGT | TTG | GTA | AAC | CCA | CCA | CCA | AGA | 1926 |
| Val | Ser | Arg | Val | Val | Ser | Ser | Thr | Arg | Leu | Val | Asn | Pro | Pro | Pro | Arg | |
| | | | 615 | | | | | 620 | | | | | 625 | | | |
| CCT | TCA | GGA | AAT | GCA | GCA | GCA | AAG | ATA | CCT | AAT | CCT | ATA | GTA | GGA | GTC | 1974 |
| Pro | Ser | Gly | Asn | Ala | Ala | Ala | Lys | Ile | Pro | Asn | Pro | Ile | Val | Gly | Val | |
| | | 630 | | | | | 635 | | | | | 640 | | | | |
| AAG | AGG | ACA | TCC | TCA | CCT | CAT | AAA | GAA | GAG | AGC | CCC | AAG | AAA | ACC | AAA | 2022 |
| Lys | Arg | Thr | Ser | Ser | Pro | His | Lys | Glu | Glu | Ser | Pro | Lys | Lys | Thr | Lys | |
| | 645 | | | | | 650 | | | | | 655 | | | | | |
| ACA | GAA | GAG | GAT | GAA | ACA | AGT | GAA | GAT | GCT | AAC | TGT | CTT | GCT | TTG | AGT | 2070 |
| Thr | Glu | Glu | Asp | Glu | Thr | Ser | Glu | Asp | Ala | Asn | Cys | Leu | Ala | Leu | Ser | |
| 660 | | | | | 665 | | | | | 670 | | | | | 675 | |
| GGA | CAT | GAT | AAA | ACA | GAA | ACA | AAG | GAA | CAA | CTT | GAT | ACA | GAG | ACA | AGT | 2118 |
| Gly | His | Asp | Lys | Thr | Glu | Thr | Lys | Glu | Gln | Leu | Asp | Thr | Glu | Thr | Ser | |
| | | | | 680 | | | | | 685 | | | | | 690 | | |
| ACA | ACT | CAA | TCA | GAA | ACC | ATT | CAG | ACA | GCG | ACT | TCT | CTG | TTG | GCC | TCT | 2166 |
| Thr | Thr | Gln | Ser | Glu | Thr | Ile | Gln | Thr | Ala | Thr | Ser | Leu | Leu | Ala | Ser | |
| | | | 695 | | | | | 700 | | | | | 705 | | | |
| CAG | AAA | ACA | TCC | AGT | ACA | GAC | CTT | TCT | GAT | ATC | CCT | GCT | CTC | CCT | GCA | 2214 |
| Gln | Lys | Thr | Ser | Ser | Thr | Asp | Leu | Ser | Asp | Ile | Pro | Ala | Leu | Pro | Ala | |
| | | 710 | | | | | 715 | | | | | 720 | | | | |
| AAC | CCT | ATT | CCT | GTT | ATC | AAG | AAT | TCA | ATA | AAA | CTG | AGA | TTG | AAT | CGG | 2262 |
| Asn | Pro | Ile | Pro | Val | Ile | Lys | Asn | Ser | Ile | Lys | Leu | Arg | Leu | Asn | Arg | |
| | 725 | | | | | 730 | | | | | 735 | | | | | |

| | | | | |
|---|---|---|---|---|
| TAAAACAAC | CTCAGGGTCC | AGAAACAGTG | TCTGCCAACT | CAACCTGTTG TCTTCAAATG | 2322 |
| CTAAAAAGG | AGAACGGAGG | GTGCAAGACT | AGACGTGACT | GAAAGTGGAT TGAGGGTTTT | 2382 |
| TTTGTGACCT | CCCTTACTGG | GCTAATCAGC | ACTTGATCGG | AAGTCCAGGT TAGTATGTGA | 2442 |
| AGCCAGGAGT | ACTATTATTA | TTGTGTTAGC | AACAGTTGCA | | 2482 |

(2) INFORMATION FOR SEQ ID NO:2:

(i) SEQUENCE CHARACTERISTICS:
        (A) LENGTH: 739 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Pro | Phe | Pro | Val | Thr | Thr | Gln | Gly | Ser | Gln | Gln | Thr | Gln | Pro | Pro |
| 1 | | | | 5 | | | | | 10 | | | | | 15 | |
| Gln | Lys | His | Tyr | Gly | Ile | Thr | Ser | Pro | Ile | Ser | Leu | Ala | Ala | Pro | Lys |
| | | | 20 | | | | | 25 | | | | | 30 | | |
| Glu | Thr | Asp | Cys | Leu | Leu | Thr | Gln | Lys | Leu | Val | Glu | Thr | Leu | Lys | Pro |
| | | 35 | | | | | 40 | | | | | 45 | | | |
| Phe | Gly | Val | Phe | Glu | Glu | Glu | Glu | Leu | Gln | Arg | Arg | Ile | Phe | Ile |
| | 50 | | | | 55 | | | | | 60 | | | | | |
| Leu | Gly | Lys | Leu | Asn | Asn | Leu | Val | Lys | Glu | Trp | Ile | Arg | Glu | Ile | Ser |
| 65 | | | | | 70 | | | | | 75 | | | | | 80 |
| Glu | Ser | Lys | Asn | Leu | Pro | Gln | Ser | Val | Ile | Glu | Asn | Val | Gly | Gly | Lys |

|   |     |     |     |     |     |     |     |     | 85  |     |     |     |     |     |     |     | 90  |     |     |     |     |     |     |     | 95  |     |     |
|---|---|---|---|---|---|---|---|---|---|---|---|---|---|---|---|---|---|---|---|---|---|---|---|---|---|---|---|

Ile Phe Thr Phe Gly Ser Tyr Arg Leu Gly Val His Thr Lys Gly Ala
            100                 105                 110

Asp Ile Asp Ala Leu Cys Val Ala Pro Arg His Val Asp Arg Ser Asp
            115                 120                 125

Phe Phe Thr Ser Phe Tyr Asp Lys Leu Lys Leu Gln Glu Glu Val Lys
            130                 135                 140

Asp Leu Arg Ala Val Glu Glu Ala Phe Val Pro Val Ile Lys Leu Cys
145                     150                 155                 160

Phe Asp Gly Ile Glu Ile Asp Ile Leu Phe Ala Arg Leu Ala Leu Gln
                165                 170                 175

Thr Ile Pro Glu Asp Leu Asp Leu Arg Asp Asp Ser Leu Leu Lys Asn
            180                 185                 190

Leu Asp Ile Arg Cys Ile Arg Ser Leu Asn Gly Cys Arg Val Thr Asp
            195                 200                 205

Glu Ile Leu His Leu Val Pro Asn Ile Asp Asn Phe Arg Leu Thr Leu
    210                 215                 220

Arg Ala Ile Lys Leu Trp Ala Lys Arg His Asn Ile Tyr Ser Asn Ile
225                 230                 235                 240

Leu Gly Phe Leu Gly Gly Val Ser Trp Ala Met Leu Val Ala Arg Thr
            245                 250                 255

Cys Gln Leu Tyr Pro Asn Ala Ile Ala Ser Thr Leu Val His Lys Phe
            260                 265                 270

Phe Leu Val Phe Ser Lys Trp Glu Trp Pro Asn Pro Val Leu Leu Lys
            275                 280                 285

Gln Pro Glu Glu Cys Asn Leu Asn Leu Pro Val Trp Asp Pro Arg Val
    290                 295                 300

Asn Pro Ser Asp Arg Tyr His Leu Met Pro Ile Ile Thr Pro Ala Tyr
305                 310                 315                 320

Pro Gln Gln Asn Ser Thr Tyr Asn Val Ser Val Ser Thr Arg Met Val
            325                 330                 335

Met Val Glu Glu Phe Lys Gln Gly Leu Ala Ile Thr Asp Glu Ile Leu
            340                 345                 350

Leu Ser Lys Ala Glu Trp Ser Lys Leu Phe Glu Ala Pro Asn Phe Phe
            355                 360                 365

Gln Lys Tyr Gln His Asp Ile Val Leu Leu Ala Ser Ala Pro Thr Glu
    370                 375                 380

Lys Gln Arg Leu Glu Trp Val Gly Leu Val Glu Ser Lys Ile Arg Ile
385                 390                 395                 400

Leu Val Gly Ser Leu Glu Lys Asn Glu Phe Met Thr Leu Ala His Val
            405                 410                 415

Asn Pro Gln Ser Phe Pro Ala Pro Lys Glu Asn Pro Asp Lys Glu Glu
            420                 425                 430

Phe Arg Thr Met Trp Val Ile Gly Leu Val Phe Asn Lys Thr Glu Asn
            435                 440                 445

Ser Glu Asn Leu Ser Val Asp Leu Thr Tyr Asp Ile Gln Ser Phe Thr
    450                 455                 460

Asp Thr Val Tyr Arg Gln Ala Ile Asn Ser Lys Met Phe Glu Val Asp
465                 470                 475                 480

Met Lys Ile Ala Ala Met His Val Lys Arg Lys Gln Leu His Gln Leu
            485                 490                 495

Leu Pro Ser His Val Leu Gln Lys Lys Lys His Ser Thr Glu Gly
            500                 505                 510

| | | | | | | | | | | | | | | | |
|---|---|---|---|---|---|---|---|---|---|---|---|---|---|---|---|
| Val | Lys | Leu<br>515 | Thr | Pro | Leu | Asn | Asp<br>520 | Ser | Ser | Leu | Asp<br>525 | Ser | Met | Asp | |
| Ser | Asp<br>530 | Asn | Ser | Met | Ser | Val<br>535 | Pro | Ser | Pro | Thr | Ser<br>540 | Ala | Met | Lys | Thr |
| Ser<br>545 | Pro | Leu | Asn | Ser | Ser<br>550 | Gly | Ser | Ser | Gln | Gly<br>555 | Arg | Asn | Ser | Pro | Ala<br>560 |
| Pro | Ala | Val | Thr | Ala<br>565 | Ala | Ser | Val | Thr | Asn<br>570 | Ile | Gln | Ala | Thr | Glu<br>575 | Val |
| Ser | Leu | Pro | Gln<br>580 | Ile | Asn | Ser | Ser | Glu<br>585 | Ser | Ser | Gly | Gly<br>590 | Thr | Ser | Ser |
| Glu | Ser | Ile<br>595 | Pro | Gln | Thr | Ala | Thr<br>600 | Gln | Pro | Ala | Ile | Ser<br>605 | Ser | Pro | Pro |
| Lys | Pro<br>610 | Thr | Val | Ser | Arg | Val<br>615 | Val | Ser | Ser | Thr | Arg<br>620 | Leu | Val | Asn | Pro |
| Pro<br>625 | Pro | Arg | Pro | Ser | Gly<br>630 | Asn | Ala | Ala | Ala | Lys<br>635 | Ile | Pro | Asn | Pro | Ile<br>640 |
| Val | Gly | Val | Lys | Arg<br>645 | Thr | Ser | Ser | Pro | His<br>650 | Lys | Glu | Glu | Ser | Pro<br>655 | Lys |
| Lys | Thr | Lys | Thr<br>660 | Glu | Glu | Asp | Glu | Thr<br>665 | Ser | Glu | Asp | Ala | Asn<br>670 | Cys | Leu |
| Ala | Leu | Ser<br>675 | Gly | His | Asp | Lys | Thr<br>680 | Glu | Thr | Lys | Glu | Gln<br>685 | Leu | Asp | Thr |
| Glu | Thr<br>690 | Ser | Thr | Thr | Gln | Ser<br>695 | Glu | Thr | Ile | Gln | Thr<br>700 | Ala | Thr | Ser | Leu |
| Leu<br>705 | Ala | Ser | Gln | Lys | Thr<br>710 | Ser | Ser | Thr | Asp | Leu<br>715 | Ser | Asp | Ile | Pro | Ala<br>720 |
| Leu | Pro | Ala | Asn | Pro<br>725 | Ile | Pro | Val | Ile | Lys<br>730 | Asn | Ser | Ile | Lys | Leu<br>735 | Arg |
| Leu | Asn | Arg | | | | | | | | | | | | | |

(2) INFORMATION FOR SEQ ID NO:3:

(i) SEQUENCE CHARACTERISTICS:
    (A) LENGTH: 1821 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

```
CATATGAGCT CTCAAAAGGT TTTTGGTATT ACTGGACCTG TTTCCACCGT GGGCGCCACA      60
GCAGCAGAAA ATAAATTAAA TGATAGTTTA ATCCAAGAAC TGAAAAAGGA AGGATCGTTC     120
GAAACAGAGC AAGAAACTGC CAATAGGGTA CAAGTGTTGA AATATTGCA  GGAATTGGCA     180
CAAAGATTTG TTTATGAAGT ATCGAAGAAG AAAAATATGT CAGACGGGAT GGCAAGGGAT     240
GCTGGTGGGA AGATTTTTAC GTATGGGTCT TATAGACTAG GAGTCCATGG GCCTGGTAGT     300
GATATCGATA CTTTGGTAGT TGTTCCAAAA CATGTAACTC GGGAAGATTT TTTTACGGTA     360
TTTGATTCAC TACTGAGAGA GAGGAAGGAA CTGGATGAAA TCGCACCTGT ACCTGATGCG     420
TTTGTCCCGA TTATCAAGAT AAAGTTCAGT GGTATTTCTA TCGATTTAAT CTGTGCACGT     480
CTAGACCAAC CTCAAGTGCC TTTATCCTTG ACTTTATCAG ATAAAAATCT ACTGCGAAAT     540
CTAGACGAGA AGGACTTGAG AGCTTTGAAT GGTACCAGGG TAACAGATGA GATATTAGAA     600
CTGGTACCAA AGCCGAATGT TTTCAGAATC GCTTTAAGAG CTATTAAGCT ATGGGCCCAA     660
AGAAGGGCTG TTTATGCTAA TATTTTTGGT TTTCCTGGTG GTGTGGCTTG GGCCATGCTA     720
```

```
GTGGCTAGAA  TTTGTCAACT  ATACCCTAAC  GCCTGTAGCG  CAGTTATATT  GAACAGATTT      780
TTCATCATTT  TGTCGGAATG  GAATTGGCCA  CAACCTGTTA  TCTTGAAACC  AATTGAGGAT      840
GGCCCGTTAC  AAGTTCGTGT  ATGGAATCCA  AAGATATATG  CCCAAGACAG  GTCTCACAGA      900
ATGCCCGTCA  TTACACCAGC  TTACCCATCA  ATGTGTGCTA  CCCATAACAT  CACGGAATCT      960
ACTAAAAAAG  TCATTTTACA  GGAATTCGTA  AGAGGCGTTC  AAATTACGAA  TGATATTTTT     1020
TCCAATAAGA  AGTCCTGGGC  CAATTTATTC  GAAAAAAACG  ATTTTTTCTT  TCGATACAAG     1080
TTCTATTTAG  AAATTACTGC  ATATACAAGG  GGCAGTGACG  AGCAGCATTT  AAAATGGAGT     1140
GGTCTTGTTG  AAAGTAAGGT  AAGGCTTCTA  GTTATGAAAC  TGGAGGTGTT  AGCTGGAATA     1200
AAAATTGCAC  ATCCTTTCAC  CAAACCCTTT  GAAAGTAGTT  ATTGTTGTCC  AACCGAGGAT     1260
GACTATGAAA  TGATTCAAGA  CAAATACGGT  AGTCATAAAA  CTGAGACAGC  ACTGAACGCC     1320
CTTAAACTGG  TAACAGATGA  AAATAAAGAG  GAAGAAAGTA  TTAAAGATGC  ACCAAAGGCA     1380
TATTTAAGCA  CCATGTACAT  AGGCCTTGAC  TTTAATATTG  AAAACAAAAA  GGAAAAAGTT     1440
GACATTCACA  TTCCCTGCAC  TGAATTTGTG  AATTTATGTC  GAAGTTTCAA  TGAGGATTAT     1500
GGTGACCACA  AAGTATTCAA  TCTAGCCCTC  CGCTTCGTAA  AGGGTTACGA  TTTGCCAGAT     1560
GAAGTTTTCG  ATGAAAATGA  AAAGAGACCA  TCAAAGAAGA  GTAAAAGGAA  GAATTTAGAT     1620
GCTAGACATG  AAACCGTGAA  GAGATCTAAA  TCAGATGCTG  CTTCAGGTGA  CAACATCAAT     1680
GGCACAACCG  CAGCTGTTGA  CGTAAACTAA  GACATTCCTA  TTTATAGTTG  AATAGTTTAT     1740
TAATATAGGT  TAATCAGTCA  TAAACAAACT  TGTACCCTTT  TTTTGAATC   AAAGTACCTT     1800
TTTTACGGCC  CGGGGGATCT  C                                                 1821
```

( 2 ) INFORMATION FOR SEQ ID NO:4:

( i ) SEQUENCE CHARACTERISTICS:
        ( A ) LENGTH: 568 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ser  Ser  Gln  Lys  Val  Phe  Gly  Ile  Thr  Gly  Pro  Val  Ser  Thr  Val
 1                 5                      10                      15

Gly  Ala  Thr  Ala  Ala  Glu  Asn  Lys  Leu  Asn  Asp  Ser  Leu  Ile  Gln  Glu
                20                      25                      30

Leu  Lys  Lys  Glu  Gly  Ser  Phe  Glu  Thr  Gln  Glu  Thr  Ala  Asn  Arg
           35                      40                      45

Val  Gln  Val  Leu  Lys  Ile  Leu  Gln  Glu  Leu  Ala  Gln  Arg  Phe  Val  Tyr
      50                      55                      60

Glu  Val  Ser  Lys  Lys  Lys  Asn  Met  Ser  Asp  Gly  Met  Ala  Arg  Asp  Ala
 65                     70                      75                      80

Gly  Gly  Lys  Ile  Phe  Thr  Tyr  Gly  Ser  Tyr  Arg  Leu  Gly  Val  His  Gly
                     85                      90                      95

Pro  Gly  Ser  Asp  Ile  Asp  Thr  Leu  Val  Val  Pro  Lys  His  Val  Thr
               100                     105                     110

Arg  Glu  Asp  Phe  Phe  Thr  Val  Phe  Asp  Ser  Leu  Leu  Arg  Glu  Arg  Lys
          115                     120                     125

Glu  Leu  Asp  Glu  Ile  Ala  Pro  Val  Pro  Asp  Ala  Phe  Val  Pro  Ile  Ile
      130                     135                     140

Lys  Ile  Lys  Phe  Ser  Gly  Ile  Ser  Ile  Asp  Leu  Ile  Cys  Ala  Arg  Leu
145                     150                     155                     160
```

```
Asp Gln Pro Gln Val Pro Leu Ser Leu Thr Leu Ser Asp Lys Asn Leu
                165                 170                 175
Leu Arg Asn Leu Asp Glu Lys Asp Leu Arg Ala Leu Asn Gly Thr Arg
            180                 185                 190
Val Thr Asp Glu Ile Leu Glu Leu Val Pro Lys Pro Asn Val Phe Arg
        195                 200                 205
Ile Ala Leu Arg Ala Ile Lys Leu Trp Ala Gln Arg Arg Ala Val Tyr
210                     215                 220
Ala Asn Ile Phe Gly Phe Pro Gly Gly Val Ala Trp Ala Met Leu Val
225                 230                 235                 240
Ala Arg Ile Cys Gln Leu Tyr Pro Asn Ala Cys Ser Ala Val Ile Leu
                245                 250                 255
Asn Arg Phe Phe Ile Ile Leu Ser Glu Trp Asn Trp Pro Gln Pro Val
            260                 265                 270
Ile Leu Lys Pro Ile Glu Asp Gly Pro Leu Gln Val Arg Val Trp Asn
        275                 280                 285
Pro Lys Ile Tyr Ala Gln Asp Arg Ser His Arg Met Pro Val Ile Thr
    290                 295                 300
Pro Ala Tyr Pro Ser Met Cys Ala Thr His Asn Ile Thr Glu Ser Thr
305                 310                 315                 320
Lys Lys Val Ile Leu Gln Glu Phe Val Arg Gly Val Gln Ile Thr Asn
                325                 330                 335
Asp Ile Phe Ser Asn Lys Lys Ser Trp Ala Asn Leu Phe Glu Lys Asn
            340                 345                 350
Asp Phe Phe Phe Arg Tyr Lys Phe Tyr Leu Glu Ile Thr Ala Tyr Thr
            355                 360                 365
Arg Gly Ser Asp Glu Gln His Leu Lys Trp Ser Gly Leu Val Glu Ser
    370                 375                 380
Lys Val Arg Leu Leu Val Met Lys Leu Glu Val Leu Ala Gly Ile Lys
385                 390                 395                 400
Ile Ala His Pro Phe Thr Lys Pro Phe Glu Ser Ser Tyr Cys Cys Pro
                405                 410                 415
Thr Glu Asp Asp Tyr Glu Met Ile Gln Asp Lys Tyr Gly Ser His Lys
            420                 425                 430
Thr Glu Thr Ala Leu Asn Ala Leu Lys Leu Val Thr Asp Glu Asn Lys
        435                 440                 445
Glu Glu Glu Ser Ile Lys Asp Ala Pro Lys Ala Tyr Leu Ser Thr Met
    450                 455                 460
Tyr Ile Gly Leu Asp Phe Asn Ile Glu Asn Lys Lys Glu Lys Val Asp
465                 470                 475                 480
Ile His Ile Pro Cys Thr Glu Phe Val Asn Leu Cys Arg Ser Phe Asn
                485                 490                 495
Glu Asp Tyr Gly Asp His Lys Val Phe Asn Leu Ala Leu Arg Phe Val
            500                 505                 510
Lys Gly Tyr Asp Leu Pro Asp Glu Val Phe Asp Glu Asn Glu Lys Arg
        515                 520                 525
Pro Ser Lys Lys Ser Lys Arg Lys Asn Leu Asp Ala Arg His Glu Thr
    530                 535                 540
Val Lys Arg Ser Lys Ser Asp Ala Ala Ser Gly Asp Asn Ile Asn Gly
545                 550                 555                 560
Thr Thr Ala Ala Val Asp Val Asn
                565
```

( 2 ) INFORMATION FOR SEQ ID NO:5:

( i ) SEQUENCE CHARACTERISTICS:
       ( A ) LENGTH: 87 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| GTGTTTGGGA | TAACACGGTG | GGGGCGACGC | CGAATTCGTG | TTTGGGATAA | CTGGACCTGT | 60 |
| TTCCACGGTG | GGGGCGACGG | TCGACGG | | | | 87 |

( 2 ) INFORMATION FOR SEQ ID NO:6:

( i ) SEQUENCE CHARACTERISTICS:
       ( A ) LENGTH: 2114 base pairs
       ( B ) TYPE: nucleic acid
       ( C ) STRANDEDNESS: single
       ( D ) TOPOLOGY: linear ( i i ) MOLECULE TYPE: DNA (genomic)

( i x ) FEATURE:
       ( A ) NAME/KEY: CDS
       ( B ) LOCATION: 109..1233

( x i ) SEQUENCE DESCRIPTION: SEQ ID NO:6:

```
TGGATTCCGT CCACTGAGGC GGGAGGGAGG GGGGGGCCTG CCTCAGCCCT GGGCGGCACG       60

GCGGCGGTTG CGGGGGGGAA GTGACTGGGC GGTGCGGCGC GGAGACG ATG CCG TTT        117
                                                     Met Pro Phe
                                                      1

CCA GTT ACA ACA CAG GGA TCA CAA CAA ACA CAA CCG CCA CAG AAG CAC       165
Pro Val Thr Thr Gln Gly Ser Gln Gln Thr Gln Pro Pro Gln Lys His
      5               10                  15

TAT GGC ATT ACT TCT CCT ATC AGC TTA GCA GCC CCC AAG GAG ACT GAC       213
Tyr Gly Ile Thr Ser Pro Ile Ser Leu Ala Ala Pro Lys Glu Thr Asp
 20              25                  30                  35

TGC GTA CTT ACA CAG AAA CTA ATT GAG ACA TTG AAA CCC TTT GGG GTT       261
Cys Val Leu Thr Gln Lys Leu Ile Glu Thr Leu Lys Pro Phe Gly Val
              40                  45                  50

TTT GAA GAG GAA GAG GAA CTG CAG CGC AGG ATT TTT ATT TTG GGA AAA       309
Phe Glu Glu Glu Glu Glu Leu Gln Arg Arg Ile Phe Ile Leu Gly Lys
                  55                  60                  65

CTA AAT AAC CTG GTA AAA GAG TGG ATA CGA GAA ATC AGT GAA AGC AAG       357
Leu Asn Asn Leu Val Lys Glu Trp Ile Arg Glu Ile Ser Glu Ser Lys
              70                  75                  80

AAT CTT CCA CAA TCT GTA ATT GAA AAT GTT GGA GGA AAA ATT TTT ACA       405
Asn Leu Pro Gln Ser Val Ile Glu Asn Val Gly Gly Lys Ile Phe Thr
          85                  90                  95

TTT GGA TCT TAC AGA TTA GGA GTG CAT ACA AAA GGT GCT GAT ATT GAT       453
Phe Gly Ser Tyr Arg Leu Gly Val His Thr Lys Gly Ala Asp Ile Asp
100                 105                 110                 115

GCG TTG TGT GTT GCA CCA ACA CAT GTT GAT CGA AGT GAC TTT TTC ACC       501
Ala Leu Cys Val Ala Pro Thr His Val Asp Arg Ser Asp Phe Phe Thr
                    120                 125                 130

TCA TTC TAT GAT AAG TTG AAA TTA CAG GAA GAA GTA AAA GAT TTA AGA       549
Ser Phe Tyr Asp Lys Leu Lys Leu Gln Glu Glu Val Lys Asp Leu Arg
                135                 140                 145

GCT GTT GAA GAG GCA TTC GTA CCA GTT ATT AAA CTC TGT TTT GAT GGG       597
Ala Val Glu Glu Ala Phe Val Pro Val Ile Lys Leu Cys Phe Asp Gly
            150                 155                 160

ATA GAG ATT GAT ATT TTG TTT GCA AGA TTA GCA CTG CAG ACA ATT CCT       645
```

```
Ile Glu Ile Asp Ile Leu Phe Ala Arg Leu Ala Leu Gln Thr Ile Pro
    165                 170                 175

GAA GAT TTG GAT CTA CGA GAT GAC AGT CTG CTA AAA AAT TTA GAT ATA      693
Glu Asp Leu Asp Leu Arg Asp Asp Ser Leu Leu Lys Asn Leu Asp Ile
180                 185                 190                 195

AGA TGT ATA AGA AGT CTT AAC GGT TGC AGG GTA ACC GAT GAA ATT TTA      741
Arg Cys Ile Arg Ser Leu Asn Gly Cys Arg Val Thr Asp Glu Ile Leu
                200                 205                 210

CAT CTA GTA CCA AAC ATT GAC AAC TTC AGG TTA ACT CTG AGA GCT ATC      789
His Leu Val Pro Asn Ile Asp Asn Phe Arg Leu Thr Leu Arg Ala Ile
            215                 220                 225

AAA CTA TGG GCC AAA CGC CAC AAC ATC TAT TCC AAT ATA TTA GGT TTC      837
Lys Leu Trp Ala Lys Arg His Asn Ile Tyr Ser Asn Ile Leu Gly Phe
        230                 235                 240

CTC GGT GGT GTT TCC TGG GCT ATG CTA GTA GCA AGA ACT TGC CAG CTT      885
Leu Gly Gly Val Ser Trp Ala Met Leu Val Ala Arg Thr Cys Gln Leu
    245                 250                 255

TAT CCA AAT GCA ATA GCA TCA ACT CTT GTA CAT AAA TTT TTC TTG GTA      933
Tyr Pro Asn Ala Ile Ala Ser Thr Leu Val His Lys Phe Phe Leu Val
260                 265                 270                 275

TTT TCT AAA TGG GAA TGG CCA AAT CCA GTG CTA TTG AAA CAG CCT GAA      981
Phe Ser Lys Trp Glu Trp Pro Asn Pro Val Leu Leu Lys Gln Pro Glu
                280                 285                 290

GAA TGC AAT CTT AAT TTG CCT GTA TGG GAC CCA AGG GTA AAC CCC AGT     1029
Glu Cys Asn Leu Asn Leu Pro Val Trp Asp Pro Arg Val Asn Pro Ser
            295                 300                 305

GAT AGG TAC CAT CTT ATG CCT ATA ATT ACA CCA GCA TAC CCA CAA CAG     1077
Asp Arg Tyr His Leu Met Pro Ile Ile Thr Pro Ala Tyr Pro Gln Gln
        310                 315                 320

AAC TCC ACG TAC AAT GTG TCC GTT TCA ACA CGG ATG GTC ATG GTT GAG     1125
Asn Ser Thr Tyr Asn Val Ser Val Ser Thr Arg Met Val Met Val Glu
    325                 330                 335

GAG TTT AAA CAA GGT CTT GCT ATC ACA GAT GAA ATT TTG CTG AGT AAG     1173
Glu Phe Lys Gln Gly Leu Ala Ile Thr Asp Glu Ile Leu Leu Ser Lys
340                 345                 350                 355

GCA GAG TGG TCC AAA CTT TTT GAA GCT CCA AAC TTC TTT CAA AAG TAC     1221
Ala Glu Trp Ser Lys Leu Phe Glu Ala Pro Asn Phe Phe Gln Lys Tyr
                360                 365                 370

AAG TAT GTA TTT TAAGGCATGT CGGACATGTT GCTCTCTTAA GTAATGGTTT        1273
Lys Tyr Val Phe
            375

AATGGTAGCA CATCATGACA TTTCTTCTTG CTGGACTAAT GTTATTGGAA GAATTTTCTT  1333

TCCTGTCACA AGGACATACT GTTTTAGTGA ACTCCTTAGT TTTTTTGGT TGAGGTAATG   1393

AATGTGAACC CCCTTTGATT TTTCTGCCCG ATCTAACTGA ACTCCTGCTA CATTTGTAGC  1453

AACATAAGTT CTGTAGGCAT ACATCAGTCA TGACAAAAAC AGTACATCTG TATACAGTGG  1513

CAAGTGGATG CACCCTGAAA AATCTGTAGT TAATAATTCT CTGCTAAGAA ACAGTATTTT  1573

TATCTAATTC TGGAAACTCA TTAATTGCTA GGAATCTTTA AACAAAGAC AAAGCTAATA   1633

AAATGTCAAT ATATAGCCAA TTAAATGTTT TCAATAGTTA CAGCACATTA TTGGCCTGCC  1693

ATTTTCCCCC AATGTTATAG CCCCTTCAAA TATTTCTACA GCTAGCTTTC ATGAATCTAA  1753

GTGGGTGTTA ATCATGTTAA TTCATGGTTT AAATATAATG GTTAATACC TTAGTACAGG   1813

TTAAAAGCTT CATTAATTGT GTTAGTTTTG ATGAAAAATG TAAGTTATAA TCTTATTTAA  1873

AAAACAGACA AACCACAGAC TTGCACTTTT ATTTGCCCTG GGCTGAAAAT GTGCCAAAGT  1933

CCCACTTAAA ATTTTTTGTT AATGCTTGAA GCTTTCTGA CCATTTGATC TTGTGTTGGA   1993

TTGTGTTTTG TAATAATCTA AGCAAGATTG CTTTATGCTC TTCCCCAATT AAAAACAAGA  2053
```

```
ATTATGACCT TCAAAAAAAA AAAAAAAAAA AAAAAAAAAA AAAAAAAAAA AAAAAAAAAA    2113
A                                                                    2114
```

( 2 ) INFORMATION FOR SEQ ID NO:7:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Pro Phe Pro Val Thr Thr Gln Gly Ser Gln Gln Thr Gln Pro Pro
 1               5                  10                  15

Gln Lys His Tyr Gly Ile Thr Ser Pro Ile Ser Leu Ala Ala Pro Lys
            20                  25                  30

Glu Thr Asp Cys Val Leu Thr Gln Lys Leu Ile Glu Thr Leu Lys Pro
        35                  40                  45

Phe Gly Val Phe Glu Glu Glu Glu Leu Gln Arg Arg Ile Phe Ile
    50                  55                  60

Leu Gly Lys Leu Asn Asn Leu Val Lys Glu Trp Ile Arg Glu Ile Ser
65                  70                  75                  80

Glu Ser Lys Asn Leu Pro Gln Ser Val Ile Glu Asn Val Gly Gly Lys
                85                  90                  95

Ile Phe Thr Phe Gly Ser Tyr Arg Leu Gly Val His Thr Lys Gly Ala
            100                 105                 110

Asp Ile Asp Ala Leu Cys Val Ala Pro Thr His Val Asp Arg Ser Asp
        115                 120                 125

Phe Phe Thr Ser Phe Tyr Asp Lys Leu Lys Leu Gln Glu Glu Val Lys
    130                 135                 140

Asp Leu Arg Ala Val Glu Glu Ala Phe Val Pro Val Ile Lys Leu Cys
145                 150                 155                 160

Phe Asp Gly Ile Glu Ile Asp Ile Leu Phe Ala Arg Leu Ala Leu Gln
                165                 170                 175

Thr Ile Pro Glu Asp Leu Asp Leu Arg Asp Asp Ser Leu Leu Lys Asn
            180                 185                 190

Leu Asp Ile Arg Cys Ile Arg Ser Leu Asn Gly Cys Arg Val Thr Asp
        195                 200                 205

Glu Ile Leu His Leu Val Pro Asn Ile Asp Asn Phe Arg Leu Thr Leu
    210                 215                 220

Arg Ala Ile Lys Leu Trp Ala Lys Arg His Asn Ile Tyr Ser Asn Ile
225                 230                 235                 240

Leu Gly Phe Leu Gly Gly Val Ser Trp Ala Met Leu Val Ala Arg Thr
                245                 250                 255

Cys Gln Leu Tyr Pro Asn Ala Ile Ala Ser Thr Leu Val His Lys Phe
            260                 265                 270

Phe Leu Val Phe Ser Lys Trp Glu Trp Pro Asn Pro Val Leu Leu Lys
        275                 280                 285

Gln Pro Glu Glu Cys Asn Leu Asn Leu Pro Val Trp Asp Pro Arg Val
    290                 295                 300

Asn Pro Ser Asp Arg Tyr His Leu Met Pro Ile Ile Thr Pro Ala Tyr
305                 310                 315                 320

Pro Gln Gln Asn Ser Thr Tyr Asn Val Ser Val Ser Thr Arg Met Val
                325                 330                 335
```

| | | | | | | | | | | | | | | | |
|---|---|---|---|---|---|---|---|---|---|---|---|---|---|---|---|
| Met | Val | Glu | Glu | Phe | Lys | Gln | Gly | Leu | Ala | Ile | Thr | Asp | Glu | Ile | Leu |
| | | | 340 | | | | 345 | | | | | 350 | | | |
| Leu | Ser | Lys | Ala | Glu | Trp | Ser | Lys | Leu | Phe | Glu | Ala | Pro | Asn | Phe | Phe |
| | | 355 | | | | 360 | | | | | 365 | | | | |
| Gln | Lys | Tyr | Lys | Tyr | Val | Phe | | | | | | | | | |
| | 370 | | | | | 375 | | | | | | | | | |

( 2 ) INFORMATION FOR SEQ ID NO:8:

( i ) SEQUENCE CHARACTERISTICS:
        ( A ) LENGTH: 1398 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1126

( x i ) SEQUENCE DESCRIPTION: SEQ ID NO:8:

| | | | | | | | | | | | | | | | | |
|---|---|---|---|---|---|---|---|---|---|---|---|---|---|---|---|---|
| ATG | CCG | TTT | CCA | GTT | ACA | ACA | CAG | GGA | TCA | CAA | CAA | ACA | CAA | CCG | CCA | 48 |
| Met | Pro | Phe | Pro | Val | Thr | Thr | Gln | Gly | Ser | Gln | Gln | Thr | Gln | Pro | Pro | |
| 1 | | | | 5 | | | | | 10 | | | | | 15 | | |
| CAG | AAG | CAC | TAT | GGC | ATT | ACT | TCT | CCT | ATC | AGC | TTA | GCA | GCC | CCC | AAG | 96 |
| Gln | Lys | His | Tyr | Gly | Ile | Thr | Ser | Pro | Ile | Ser | Leu | Ala | Ala | Pro | Lys | |
| | | | | 20 | | | | | 25 | | | | | 30 | | |
| GAG | ACT | GAC | TGC | GTA | CTT | ACA | CAG | AAA | CTA | ATT | GAG | ACA | TTG | AAA | CCC | 144 |
| Glu | Thr | Asp | Cys | Val | Leu | Thr | Gln | Lys | Leu | Ile | Glu | Thr | Leu | Lys | Pro | |
| | | | 35 | | | | | 40 | | | | | 45 | | | |
| TTT | GGG | GTT | TTT | GAA | GAG | GAA | GAG | GAA | CTG | CAG | CGC | AGG | ATT | TTT | ATT | 192 |
| Phe | Gly | Val | Phe | Glu | Glu | Glu | Glu | Glu | Leu | Gln | Arg | Arg | Ile | Phe | Ile | |
| | | 50 | | | | | 55 | | | | | 60 | | | | |
| TTG | GGA | AAA | CTA | AAT | AAC | CTG | GTA | AAA | GAG | TGG | ATA | CGA | GAA | ATC | AGT | 240 |
| Leu | Gly | Lys | Leu | Asn | Asn | Leu | Val | Lys | Glu | Trp | Ile | Arg | Glu | Ile | Ser | |
| 65 | | | | | 70 | | | | | 75 | | | | | 80 | |
| GAA | AGC | AAG | AAT | CTT | CCA | CAA | TCT | GTA | ATT | GAA | AAT | GTT | GGA | GGA | AAA | 288 |
| Glu | Ser | Lys | Asn | Leu | Pro | Gln | Ser | Val | Ile | Glu | Asn | Val | Gly | Gly | Lys | |
| | | | | 85 | | | | | 90 | | | | | 95 | | |
| ATT | TTT | ACA | TTT | GGA | TCT | TAC | AGA | TTA | GGA | GTG | CAT | ACA | AAA | GGT | GCT | 336 |
| Ile | Phe | Thr | Phe | Gly | Ser | Tyr | Arg | Leu | Gly | Val | His | Thr | Lys | Gly | Ala | |
| | | | 100 | | | | | 105 | | | | | 110 | | | |
| GAT | ATT | GAT | GCG | TTG | TGT | GTT | GCA | CCA | ACA | CAT | GTT | GAT | CGA | AGT | GAC | 384 |
| Asp | Ile | Asp | Ala | Leu | Cys | Val | Ala | Pro | Thr | His | Val | Asp | Arg | Ser | Asp | |
| | | | 115 | | | | | 120 | | | | | 125 | | | |
| TTT | TTC | ACC | TCA | TTC | TAT | GAT | AAG | TTG | AAA | TTA | CAG | GAA | GAA | GTA | AAA | 432 |
| Phe | Phe | Thr | Ser | Phe | Tyr | Asp | Lys | Leu | Lys | Leu | Gln | Glu | Glu | Val | Lys | |
| | | | 130 | | | | | 135 | | | | | 140 | | | |
| GAT | TTA | AGA | GCT | GTT | GAA | GAG | GCA | TTC | GTA | CCA | GTT | ATT | AAA | CTC | TGT | 480 |
| Asp | Leu | Arg | Ala | Val | Glu | Glu | Ala | Phe | Val | Pro | Val | Ile | Lys | Leu | Cys | |
| 145 | | | | | 150 | | | | | 155 | | | | | 160 | |
| TTT | GAT | GGG | ATA | GAG | ATT | GAT | ATT | TTG | TTT | GCA | AGA | TTA | GCA | CTG | CAG | 528 |
| Phe | Asp | Gly | Ile | Glu | Ile | Asp | Ile | Leu | Phe | Ala | Arg | Leu | Ala | Leu | Gln | |
| | | | | 165 | | | | | 170 | | | | | 175 | | |
| ACA | ATT | CCT | GAA | GAT | TTG | GAT | CTA | CGA | GAT | GAC | AGT | CTG | CTA | AAA | AAT | 576 |
| Thr | Ile | Pro | Glu | Asp | Leu | Asp | Leu | Arg | Asp | Asp | Ser | Leu | Leu | Lys | Asn | |
| | | | 180 | | | | | 185 | | | | | 190 | | | |
| TTA | GAT | ATA | AGA | TGT | ATA | AGA | AGT | CTT | AAC | GGT | TGC | AGG | GTA | ACC | GAT | 624 |
| Leu | Asp | Ile | Arg | Cys | Ile | Arg | Ser | Leu | Asn | Gly | Cys | Arg | Val | Thr | Asp | |
| | | 195 | | | | | 200 | | | | | 205 | | | | |
| GAA | ATT | TTA | CAT | CTA | GTA | CCA | AAC | ATT | GAC | AAC | TTC | AGG | TTA | ACT | CTG | 672 |
| Glu | Ile | Leu | His | Leu | Val | Pro | Asn | Ile | Asp | Asn | Phe | Arg | Leu | Thr | Leu | |

| | | | | | | | | | | | | | | | | |
|---|---|---|---|---|---|---|---|---|---|---|---|---|---|---|---|---|
| | | 210 | | | | | 215 | | | | | 220 | | | | |
| AGA | GCT | ATC | AAA | CTA | TGG | GCC | AAA | CGC | CAC | AAC | ATC | TAT | TCC | AAT | ATA | 720 |
| Arg | Ala | Ile | Lys | Leu | Trp | Ala | Lys | Arg | His | Asn | Ile | Tyr | Ser | Asn | Ile | |
| 225 | | | | 230 | | | | | 235 | | | | | | 240 | |
| TTA | GGT | TTC | CTC | GGT | GGT | GTT | TCC | TGG | GCT | ATG | CTA | GTA | GCA | AGA | ACT | 768 |
| Leu | Gly | Phe | Leu | Gly | Gly | Val | Ser | Trp | Ala | Met | Leu | Val | Ala | Arg | Thr | |
| | | | | 245 | | | | | 250 | | | | | 255 | | |
| TGC | CAG | CTT | TAT | CCA | AAT | GCA | ATA | GCA | TCA | ACT | CTT | GTA | CAT | AAA | TTT | 816 |
| Cys | Gln | Leu | Tyr | Pro | Asn | Ala | Ile | Ala | Ser | Thr | Leu | Val | His | Lys | Phe | |
| | | | 260 | | | | | 265 | | | | | 270 | | | |
| TTC | TTG | GTA | TTT | TCT | AAA | TGG | GAA | TGG | CCA | AAT | CCA | GTG | CTA | TTG | AAA | 864 |
| Phe | Leu | Val | Phe | Ser | Lys | Trp | Glu | Trp | Pro | Asn | Pro | Val | Leu | Leu | Lys | |
| | | 275 | | | | | 280 | | | | | 285 | | | | |
| CAG | CCT | GAA | GAA | TGC | AAT | CTT | AAT | TTG | CCT | GTA | TGG | GAC | CCA | AGG | GTA | 912 |
| Gln | Pro | Glu | Glu | Cys | Asn | Leu | Asn | Leu | Pro | Val | Trp | Asp | Pro | Arg | Val | |
| | 290 | | | | | 295 | | | | | 300 | | | | | |
| AAC | CCC | AGT | GAT | AGG | TAC | CAT | CTT | ATG | CCT | ATA | ATT | ACA | CCA | GCA | TAC | 960 |
| Asn | Pro | Ser | Asp | Arg | Tyr | His | Leu | Met | Pro | Ile | Ile | Thr | Pro | Ala | Tyr | |
| 305 | | | | | 310 | | | | | 315 | | | | | 320 | |
| CCA | CAA | CAG | AAC | TCC | ACG | TAC | AAT | GTG | TCC | GTT | TCA | ACA | CGG | ATG | GTC | 1008 |
| Pro | Gln | Gln | Asn | Ser | Thr | Tyr | Asn | Val | Ser | Val | Ser | Thr | Arg | Met | Val | |
| | | | | 325 | | | | | 330 | | | | | 335 | | |
| ATG | GTT | GAG | GAG | TTT | AAA | CAA | GGT | CTT | GCT | ATC | ACA | GAT | GAA | ATT | TTG | 1056 |
| Met | Val | Glu | Glu | Phe | Lys | Gln | Gly | Leu | Ala | Ile | Thr | Asp | Glu | Ile | Leu | |
| | | | 340 | | | | | 345 | | | | | 350 | | | |
| CTG | AGT | AAG | GCA | GAG | TGG | TCC | AAA | CTT | TTT | GAA | GCT | CCA | AAC | TTC | TTT | 1104 |
| Leu | Ser | Lys | Ala | Glu | Trp | Ser | Lys | Leu | Phe | Glu | Ala | Pro | Asn | Phe | Phe | |
| | | 355 | | | | | 360 | | | | | 365 | | | | |
| CAA | AAG | TAC | AAG | TAT | GTA | TTT | T | AAGGCATGTC | GGACATGTTG | CTCTCTTAAG | | | | | | 1156 |
| Gln | Lys | Tyr | Lys | Tyr | Val | Phe | | | | | | | | | | |
| | 370 | | | | | 375 | | | | | | | | | | |

| | | | |
|---|---|---|---|
| TAATGGTTTA | ATGGTAGCAC | ATCATGACAT | TTCTTCTTGC TGGACTAATG TTATTGGAAG | 1216 |
| AATTTTCTTT | CCTGTCACAA | GGACATACTG | TTTTAGTGAA CTCCTTAGTT TTTTTGGTT | 1276 |
| GAGGTAATGA | ATGTGAACCC | CCTTTGATTT | TTCTGCCCGA TCTAACTGAA CTCCTGCTAC | 1336 |
| ATTTGTAGCA | ACATAAGTTC | TGTAGGCATA | CATCAGTCAT GACAAAAACA GTACATCTGT | 1396 |
| AT | | | | 1398 |

( 2 ) INFORMATION FOR SEQ ID NO:9:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Pro | Phe | Pro | Val | Thr | Thr | Gln | Gly | Ser | Gln | Gln | Thr | Gln | Pro | Pro |
| 1 | | | | 5 | | | | | 10 | | | | | 15 | |
| Gln | Lys | His | Tyr | Gly | Ile | Thr | Ser | Pro | Ile | Ser | Leu | Ala | Ala | Pro | Lys |
| | | | 20 | | | | | 25 | | | | | 30 | | |
| Glu | Thr | Asp | Cys | Val | Leu | Thr | Gln | Lys | Leu | Ile | Glu | Thr | Leu | Lys | Pro |
| | | | 35 | | | | | 40 | | | | | 45 | | |
| Phe | Gly | Val | Phe | Glu | Glu | Glu | Glu | Leu | Gln | Arg | Arg | Ile | Phe | Ile | |
| | | 50 | | | | | 55 | | | | | 60 | | | |
| Leu | Gly | Lys | Leu | Asn | Asn | Leu | Val | Lys | Glu | Trp | Ile | Arg | Glu | Ile | Ser |
| 65 | | | | | 70 | | | | | 75 | | | | | 80 |
| Glu | Ser | Lys | Asn | Leu | Pro | Gln | Ser | Val | Ile | Glu | Asn | Val | Gly | Gly | Lys |

|  |  |  |  | 85 |  |  |  |  | 90 |  |  |  | 95 |  |  |
|---|---|---|---|---|---|---|---|---|---|---|---|---|---|---|---|
| Ile | Phe | Thr | Phe 100 | Gly | Ser | Tyr | Arg | Leu 105 | Gly | Val | His | Thr | Lys 110 | Gly | Ala |
| Asp | Ile | Asp 115 | Ala | Leu | Cys | Val | Ala 120 | Pro | Thr | His | Val | Asp 125 | Arg | Ser | Asp |
| Phe | Phe 130 | Thr | Ser | Phe | Tyr | Asp 135 | Lys | Leu | Lys | Leu | Gln 140 | Glu | Glu | Val | Lys |
| Asp 145 | Leu | Arg | Ala | Val | Glu 150 | Glu | Ala | Phe | Val | Pro 155 | Val | Ile | Lys | Leu | Cys 160 |
| Phe | Asp | Gly | Ile | Glu 165 | Ile | Asp | Ile | Leu | Phe 170 | Ala | Arg | Leu | Ala | Leu 175 | Gln |
| Thr | Ile | Pro | Glu 180 | Asp | Leu | Asp | Leu | Arg 185 | Asp | Asp | Ser | Leu | Leu 190 | Lys | Asn |
| Leu | Asp | Ile 195 | Arg | Cys | Ile | Arg | Ser 200 | Leu | Asn | Gly | Cys | Arg 205 | Val | Thr | Asp |
| Glu | Ile 210 | Leu | His | Leu | Val | Pro 215 | Asn | Ile | Asp | Asn | Phe 220 | Arg | Leu | Thr | Leu |
| Arg 225 | Ala | Ile | Lys | Leu | Trp 230 | Ala | Lys | Arg | His | Asn 235 | Ile | Tyr | Ser | Asn | Ile 240 |
| Leu | Gly | Phe | Leu | Gly 245 | Gly | Val | Ser | Trp | Ala 250 | Met | Leu | Val | Ala | Arg 255 | Thr |
| Cys | Gln | Leu | Tyr 260 | Pro | Asn | Ala | Ile | Ala 265 | Ser | Thr | Leu | Val | His 270 | Lys | Phe |
| Phe | Leu | Val 275 | Phe | Ser | Lys | Trp | Glu 280 | Trp | Pro | Asn | Pro | Val 285 | Leu | Leu | Lys |
| Gln | Pro 290 | Glu | Glu | Cys | Asn | Leu 295 | Asn | Leu | Pro | Val | Trp 300 | Asp | Pro | Arg | Val |
| Asn 305 | Pro | Ser | Asp | Arg | Tyr 310 | His | Leu | Met | Pro | Ile 315 | Ile | Thr | Pro | Ala | Tyr 320 |
| Pro | Gln | Gln | Asn | Ser 325 | Thr | Tyr | Asn | Val | Ser 330 | Val | Ser | Thr | Arg | Met 335 | Val |
| Met | Val | Glu | Glu 340 | Phe | Lys | Gln | Gly | Leu 345 | Ala | Ile | Thr | Asp | Glu 350 | Ile | Leu |
| Leu | Ser | Lys 355 | Ala | Glu | Trp | Ser | Lys 360 | Leu | Phe | Glu | Ala | Pro 365 | Asn | Phe | Phe |
| Gln | Lys 370 | Tyr | Lys | Tyr | Val | Phe 375 |  |  |  |  |  |  |  |  |  |